United States Patent
Lapraz

(10) Patent No.: US 9,953,139 B2
(45) Date of Patent: Apr. 24, 2018

(54) ENDOBIOGENIC-BASED PROCESSING OF BIOLOGICAL DATA

(71) Applicant: Jumplion, Inc., Pocatello, ID (US)

(72) Inventor: Jean-Claude Lapraz, Paris (FR)

(73) Assignee: JUMPLION, INC., Pocatello, ID (US)

( * ) Notice: Subject to any disclaimer, the term of this patent is extended or adjusted under 35 U.S.C. 154(b) by 0 days.

(21) Appl. No.: 14/754,193

(22) Filed: Jun. 29, 2015

(65) Prior Publication Data

US 2016/0132655 A1    May 12, 2016

Related U.S. Application Data

(63) Continuation of application No. 13/704,515, filed as application No. PCT/US2011/040853 on Jun. 17, 2011, now abandoned.
(Continued)

(51) Int. Cl.
G06F 19/00 (2018.01)
G06F 19/12 (2011.01)
G06F 19/24 (2011.01)

(52) U.S. Cl.
CPC .......... *G06F 19/3437* (2013.01); *G06F 19/12* (2013.01); *G06F 19/24* (2013.01);
(Continued)

(58) Field of Classification Search
CPC ......................................... G06C 50/22–50/24
(Continued)

(56) References Cited

U.S. PATENT DOCUMENTS

| | | | |
|---|---|---|---|
| 2005/0171817 A1* | 8/2005 | Sachdev | G06F 19/322 705/3 |
| 2005/0182568 A1* | 8/2005 | Duraffourd | C12Q 1/32 702/19 |
| 2006/0147899 A1* | 7/2006 | Famili | G06F 19/12 435/4 |

FOREIGN PATENT DOCUMENTS

EA            001194 B1    12/2000

OTHER PUBLICATIONS

Lado-Abeal et al., "Glucose Relays Information Regarding Nutritional Status to the Neural Circuits That Control the Somatotropic, Corticotropic, and Gonadotropic Axes Adult Male Rhesus Macaques", Endocrinology, vol. 143, No. 2, pp. 403-410.*
(Continued)

*Primary Examiner* — Michael Tomaszewski
(74) *Attorney, Agent, or Firm* — Womble Bond Dickinson (US) LLP

(57) ABSTRACT

A method is provided that includes processing biological data using a biological simulation model, including calculating a set of measurements called indexes that measure interrelationships between hormones and/or blood test data; and analyzing from the indexes, the endocrine system by axis and in sequence along an adaptation process. The method includes running a selection algorithm from the indexes to identify biological dysfunctions across the endocrine system and the autonomous nervous system, and recommending corrective actions based on the identified biological dysfunctions. The method includes validating potential organism dysfunctions of the patient through the identified biological dysfunctions, consolidating diagnostic actions including the recommended corrective actions into a single diagnostic, and receiving selection of diagnostic actions therefrom. And the method includes assisting in selection of a therapeutic strategy applicable to each selected
(Continued)

diagnostic action, and producing a final ready-to-use prescription with quantified dosage based thereon.

7 Claims, 34 Drawing Sheets

Related U.S. Application Data

(60) Provisional application No. 61/355,959, filed on Jun. 17, 2010.

(52) U.S. Cl.
CPC ............ *G06F 19/34* (2013.01); *G06F 19/345* (2013.01); *G01N 2800/60* (2013.01); *G06F 19/3431* (2013.01); *G06F 19/3487* (2013.01)

(58) Field of Classification Search
USPC .......................................................... 705/2–3
See application file for complete search history.

(56) References Cited

OTHER PUBLICATIONS

Chinese Office Action dated Jan. 19, 2016 for Application No. 201180039953.3.
Jean-Claude Lapraz, Md et al., "Endobiogeny: A Global Approach to Systems Biology (Part 1 of 2)", Global Advances in Health and Medicine, vol. 2, No. 1, Jan. 2013, pp. 64-78, XP008171570.
Jean-Claude Lapraz, Md et al., "Endobiogeny: A Global Approach to Sys_ems Biology (Part 2 of 2)", Global Advances in Health and Medicine, Voi. 2, No. 2, Mar. 2013, pp. 32-44, XP0081.71589.
European Communication and Extended Search Report for Application No. 11796494.0 dated Sep. 4, 2014.
Russian Office Action dated Aug. 5, 2015 for Application No. 2012154239.
Joaquin Lado-Abeal et al., "Glucose Relays Information Regarding Nutritional Status to the neutral Circuits That Control the Somatotropic. Corticotropic. And Gonadotropic Axes in Adult Male Rhesus Macaques", Endocrinology. vol. 143, No. 2, pp. 403-410.

* cited by examiner

Endobiogenics Medical Assistant 2.0

Endobiogenics Medical Assistant 2.0

WELCOME to the Endobiogenics Medical Assistant 2.0 (EMA™)

1 - A new concept of terrain: Endobiogeny
The Endobiogenic theory of terrain proposes a new dynamic description of biological mechanisms running in the human body, based on a fundamental principle: the endocrine system manages the physiological systems which ensure the living of an individual. Terrain refers to the potential and actual capacities of the body, in basal structure, in adaptation to stressors, or in its attempt to return continuously to the prior state of homeostasis. Successfully evaluating in each patient's terrain the tru disturbances participating in the installation, development or regression of pathology, is essential to correctly assessing and treating any and all disorders.

2 - Endocrine system components and relationships
The body requires a dynamic system capable of simultaneously checking, balancing, and managing the organism, while managing itself. The endocrine system is the only system that owns these qualities. It ensures the control and management of all systems (endocrine, neurologic, immunologic, musculo-skeletal, vascular, lymphatic, emunctories, and biochemical factors), while maintaining the integrated and inter-related relationships at various levels of functionality: cellular, tissue, and organ as well as the organism as a whole. The endobiogenic approach is focused around the vertical, horizontal and radial activities of the four endocrine axes of regulation: hypothalamus-pituitary-adrenal, hypothalamus-pituitary-gonadal, hypothalamus-pituitary-thyroid, and hypothalamus-pituitary-somatotropic (pancreas). The autonomic nervous system acts as the initiator of homeostasis as well as of the adaptation response of the organism, interfacing with the anabolic and catabolic activity of the endocrine system. Thus, any disorder or disease in the body, structural, functional, or pathological can be analyzed and treated, based on the correct assessment of the endocrine system and its effects upon all other systems and functions.

3 - Biological modeling and EMA™ (Endobiogenic Medical Assistant)
EMA™ is a biological modeling system that quantifies the structural and functional abilities of the organism, before and after the effects of adaption to stressors. The algorithms that permit the calculation of these indices are based on the physiological relations that exist between the direct or indirect products of hormonal and organs activity, yielding over 100 indices. The whole set of indices gives an evolutionary assessment of an individual body's functionality, system by system, organ by organ, participating in the maintenance of homeostasis as well as in the installation and development of pathological states, of any kind. In addition, the EMA™ helps the practitioner to better understand the root causes of pathologies and establish a more precise diagnostic. It also helps in the selection of therapeutic solutions, preferably or in complement to classical solutions, suggesting natural extract medications better suited to the physiology of the organism, with medicinal plants being usually the best choice. The presentation of these medications has been designed for an easy implementation, with selected plants and prepack aged symptom oriented solutions, without requiring an extensive knowledge of botany or phyto-pharmacology.

Home
About Us
Contact Us
Legal Info
Privacy Info
Login

Endobiogenics Medical Assistant 2.0

Consultation Wizard
○ Review ▶ •••
TestJones, TestJohn

Consultation Information

*Doctor: [Endo. Dr TEST ∨]
*Facility: [Test Facility]
*Date of Consultation: [MM/DD/YYYY]  8/25/2010
*Has Cancer: [No ∨]
Notes: [           ]

[⇩ Start Over]   [Next ⇧]   [Cancel]

Home
Glossary
Help
Logout

FIG. 16

Patient Review

Last Name: First Name: Patient Code:
TEST     Jack       TESTJAC
DOB:     Age:  Sex:
7/8/1951 60   Male
Phone:   Cell: Email:

Address:
370 Any Street
Anytown, New York

[Edit Patient Information]

Patient Antecedents
Patient Antecedent Summary:
Man with important business responsibilites (Large Trading Company)
Life environment subject to cardio-vascular risks: jet-lag, business meals too rich, heavy smoking, lack of sleep, limited sport activities

Personal Environment
Overall Personal Environment Notes:
*Profile
- Man aged 50 at time of 1st consultation (Oct 3, 2001)
- Tall and slim (1.90m and 82kg); never sick until his first heart attack in Feb 01
- Married; large stress created by inability to have children (both husband and wife), partly compensated by growing up the 3 children of his deceased sister
- Manages a Large Trading Company (600 employees)
- Deeply affected by Sept 11 terrorist attacks (lost 30 employees in the terrorist attack)

From Conception to Childbirth
Overall from Conception to Childbirth Notes:
- Normal process + breast feed

Medical Antecedents
Overall Medical Antecedents Notes:
- Type of pathology
- Myocardial anterior infarction in Feb 01, with coronary dissection: installation of 3 stents-treated by Zestril, Plavix and Lipodor
- Repetitive stenosis, requiring double by-pass on the anterior intraverticular, with installation of additional stents in June and September 2001
- Elevated PSA in August 01 (14.5); prostatectomy decision deferred - after appropriate treatment, the PSA will return to 3 and stay at this level
- Sept. 01: control coronography in New York
  → no new stenosis in the coronary artery
  → sinus bradycardia at 55, PR at 0.17, AQRS at 67°
  → right bundle branch block

**Previous Medical antecedents: no issue, excellent overall health state
High level of stress due to his business and his inability to have children

Traumatologic & Surgical Antecedents
Overall Traumatologic & Surgical Antecedents Notes:
- Appendix ablation at age 10
- Amyodafectomy and vegetations

Family Antecedents

FIG. 17

Past Treatments

Overall Past Treatments Notes:

Apply

Add New Patient Antecedent Items

Medical Antecedents

- From Conception to Childbirth
- Medical Antecedents
- Risk Factors and Lifestyle Habits
- List of Vaccinations ▲ Digestive
▲ Endocrine
▲ Genital
  Hematological
  Neurological
  Ophthalmologic
  Parasitosis
  Psychic
  Respiratory and ENT
  Rhumatological Items:

Back to Top

Default Date Occurred: [MM/DD/YYYY]

Select All Highlighted Items

Patient Antecedents

Add New Antecedents
Patient Antecedent Summary:

Personal Environment
Overall Personal Environment Notes:

From Conception to Childbirth

| Occurred | Name | Further Information | Notes |
|---|---|---|---|
| 08/25/2010 | Mother Treatments | | ⊗ |

Overall from Conception to Childbirth Notes:

Medical Antecedents

| Occurred | Name | Further Information | Notes |
|---|---|---|---|
| 08/25/2010 | Coordination Disorders | | ⊗ |
| 08/25/2010 | Dementia | | ⊗ |
| 08/25/2010 | Mumps | | ⊗ |
| 08/25/2010 | Paludism | | ⊗ |
| 08/25/2010 | Atopic Dermatitis | | ⊗ |

Overall Medical Antecedents Notes:

FIG. 20

Objective Signs (Clinical Review Outcome)
Overall Objective Signs (Clinical Review Outcome) Notes:
- clinical exam shows very painful zones, when palpating thorax
- congestive and painful liver
- prostate increased in volume but no sign of hardness
- no Chovstek signs

Newly Diagnosed Medical Antecedents
Overall Newly Diagnosed Medical Antecedents Notes:
- none

[Apply]

Add New Patient Examination Items

Subjective Signs (Patients Complaints) ▼
- Subjective Signs (Patients Complaints)
- Measurements
- Objective Signs (Clinical Review Outcome)
- Newly Diagnosed Medical Antecedents

- Endocrinological Signs
- General Signs
- ▸Genital Signs
- Hematological Signs
- Neurological Signs
- Opthalmologic Signs
- Psychic Signs
- Respiratory Signs and ENT
- ▸Rheumatological Signs
- Urological Signs \* Items:

\* Default Date Occurred: (MM/DD/YYYY) 10/3/2001
[Select All Highlighted Items]

Back to Top

Doctor's Summary (for Patient Report)
- Organism is in a situation of shock
- Immediate patient attention required to reduce his activities
- No business trips for next 30 days
- Next Lab test and Consultation within 30 days

[◁ Previous] [Next ▷] [Cancel]

Endobiogenics Medical Assistant 2.0

Add Lab Test

Basic Information

*Patient: Jane_Test
*Blood Index Norm Category: Children (Female)
*Date of Test: [MM/DD/YYYY] 8/26/2010
*Is Pregnant: No
*Is Cancer: No
Date of Last Menstruation: [MM/DD/YYYY]
Date of Last Chemotherapy: [MM/DD/YYYY]
Name of Last Chemotherapy:
Testing Entity Name:

Notes:

[Next] [Cancel] [Import Lab Results]

Home
Glossary
Help
Logout

FIG. 24

Lab Test/Bloodwork Index Results

| Bloodwork Index Norm | Min Value | Max Value | UOM |
|---|---|---|---|
| LDH | | | IU/l |
| CPK | | | IU/l |
| Osteocalcin | | | ng/ml |
| Total Alkaline phosphatases | | | IU/l |

| Bloodwork Index | Result Value | Calculated Result Value | UOM |
|---|---|---|---|
| Lab Results - General | | | |
| Red cells (in thousands) | | | 1,000/m (e.g. 4500) |
| Leukocytes (White Cells) | | | quantity/mm3 (e.g. 6500) |
|     Neutrophils % | | | % (percentage) |
|     Eosinophils % | | | % (percentage) |
|     Basophils % | | | % (percentage) |
|     Lymphocytes % | | | % (percentage) |
|     Monocytes % | | | % (percentage) |
| Total: | 0 % | | |
| Hemoglobin | | | g/dl (e.g. 13.2) |
| Platelets (in units) | | | quantity/mm3 |
| LDH | | | IU/l |
| CPK | | | IU/l |
| TSH (Ultra sensitive) | | | uU/ml |
| Osteocalcin | | | ng/ml |
| Total alkaline phosphatases | | | IU/l |
|     Isoenzymes Hepatic H1 % | | | % |
|     Isoenzymes Hepatic H2 % | | | % |
|     Isoenzymes bone O1 % | | | % |
|     Intestinal Isoenzymes I1 % | | | % |
|     Intestinal Isoenzymes I2 % | | | % |
|     Intestinal Isoenzymes I3 % | | | % |
| Total: | 0 % | | |
| Potassium | | | mEq/l or mmol/l |
| Calcium | | | mEq/l or mmol/l |
| E.S.R. 1 hour | | | mm |
| E.S.R. 2 hours | | | mm |

FIG. 25

Endobiogenics Medical Assistant 2.0

Consultation Wizard

○Review ▷ ○Exam ▷ ○Type ▷ ○Biology ▷ ○Axis ▷ ○Summary ▷ ○Action ▷ ○Treatment ▷ ○Prescribe ▷ ○Report
○ Corticotrope ▷ ○ Gonadotrope ▷ ○ Thyrestrope ▷ ○ Somatotrope ▷ ○ Cancer Example Jane, Test

Biology of Function Report

Class: General
Report: Complete [Run Report]
Results Display: Split Values

| Index | Type | 8/26/2010 | 8/26/2010 | Norms |
|---|---|---|---|---|
| Corticotrope | | | | |
| Beta MSH/alpha MSH | s | 4.46 ● – ● 4.46 | | 6-8 |
| | f | 4.46● – ● 4.46 | | |
| ACTH | s | 0.01 ● – ● 0.01 | | 0.71-3 |
| | f | 0.01● – ● 0.01 | | |
| Adaptation | s | 0.20 ● – ● 0.20 | | 0.25-0.5 |
| | f | 0.20● – ● 0.20 | | |
| Cata-ana ratio | s | 2.62 O – O 2.62 | | 1.8-3 |
| | f | 2.70O – O 2.70 | | |
| Cortisol | s | 13.10 ● – ● 13.10 | | 3-7 |
| | f | 13.48● – ● 13.48 | | |
| Peripheral serotonin | s | 75.21 ● – ● 75.21 | | 1.5-7.5 |
| | f | 77.39● – ● 77.39 | | |
| Starter | s | 1.03 O – O 1.03 | | 0.85-1.15 |
| | f | 1.03O – O 1.03 | | |
| Leucocytes mobilization | s | 0.98 O – O 0.98 | | 0.85-1.15 |
| | f | 0.98O – O 0.98 | | |
| Platelets mobilization | s | 0.95 O – O 0.95 | | 0.85-1.15 |
| | f | 0.95O – O 0.95 | | |
| Adaptogen | s | 0.41 ● – ● 0.41 | | 0.75-0.9 |
| | f | 0.41● – ● 0.41 | | |
| Adaptation-permissivity | s | 9.10 ● – ● 9.10 | | 1-3 |
| | f | 9.26● – ● 9.26 | | |

FIG. 26 from Fig. 31-1

Recommended Actions:
- ☒ Inhibit Alpha Sympathetic
- ☒ Stimulate Central Serotonin
- ☐ Inhibit Aromatization
- ☒ Reduce Matamine
- ☒ Fluidity Blood
- ☒ Reduce Inflammation
- ☒ Reduce Stress
- ☒ Inhibit Thyroid
- ☐ Stimulate Bone Reconstruction
- ☒ Inhibit Insulin
- ☒ Support Exocrine Pancreas
- ☐ Facilitate Insulinic Resistance
- ☐ Stimulate Protactin
- ☒ Reduce Oxidation

[Apply]

Biology Notes

Alpha sympathetic very active
Excess of peripheral serotonin
Excess of pituitary homones (ACTH/FSM)
Excess of thyroid activity Doctor's Summary (for Patient Report)

- Organism is in a situation of shock
- Immediate patient attention required to reduce his activities
- No business trips for next 30 days
- Next Lab test and Consultation within 30 days

[⇐ Previous] [Next ⇒] [Cancel] [Print]

FIG. 31-2

Endobiogenics Medical Assistant 2.0

Consultation Wizard

○ Review ▷ ○ Exam ▷ ○ Biology ▷ ○ Axis ▷ ○ Summary ▷ ○ Action ▷ ○ Treatment ▷ ○ Prescribe ▷ ○ Report
  ○ Genotrope ▷ ○ Gonadotrope ▷ ○ Thyreotrope ▷ ○ Somadotrope ▷ ○ Cancer Example TEST, Jack     10/3/2001

◁ Previous | Next ▷ | Cancel | Print

Action Summary

Please review the actions that you wish to treat (both recommended and others). Click Next when all actions you wish to treat have been selected.

Recommended Actions:
- ☒ Inhibit Alpha Sympathetic
- ☒ Stimulate Central Serotonin
- ☐ Inhibit Aromatization
- ☒ Reduce Histamine
- ☒ Fluidity Blood
- ☒ Reduce Inflammation
- ☒ Reduce Stress
- ☒ Inhibit Thyroid
- ☐ Stimulate Bone Reconstruction
- ☒ Inhibit Insulin
- ☒ Support Exocrine Pancreas
- ☐ Facilitate Insulinic Resistance
- ☐ Stimulate Prolactin
- ☒ Reduce Oxidation

[Apply]

Axial:
- ☐ Improve Arteries Trophicity
- ☐ Inhibit Adrenal Androgens
- ☐ Inhibit Aldosterone
- ☐ Inhibit Androgens
- ☐ Inhibit Beta Sympathetic
- ☐ Inhibit FSH
- ☐ Inhibit FSH/LH/TSH
- ☐ Inhibit GH
- ☐ Inhibit Gonadotrope Axis
- ☐ Inhibit LH
- ☐ Inhibit Para Sympathetic
- ☐ Inhibit Peripheral Estrogens
- ☐ Inhibit Prolactin
- ☐ Inhibit PTH
- ☐ Inhibit HRH
- ☐ Inhibit TSH
- ☐ Reduce Ischemia

Symptomatic:
- ☐ Adaptogene
- ☐ Anti allergies
- ☐ Anti bloating
- ☐ Anti coughing
- ☐ Anti depression
- ☐ Anti Diarrhea
- ☐ Anti gastroesophageal reflux
- ☐ Anti Gout / Hyperuricemia
- ☐ Anti headaches
- ☐ Anti Infectious - urinary
- ☐ Anti Infectious - ENT/Pulmonary
- ☐ Anti Infectious - general
- ☐ Anti Inflammatory - joint pains
- ☐ Anti Inflammatory - general
- ☐ Anti metabolic overload (Elevated cholesterol)
- ☐ Anti myalgias
- ☐ Anti mycosic Home | Glossary | Help | Logout

ENDOBIOGENIC-BASED PROCESSING OF BIOLOGICAL DATA

FIELD

The present invention generally relates to evaluating a physiological condition of a patient, and more particularly, relates to processing biological data using a biological simulation model for evaluating the physiological condition of the patient.

CONTENT

The content of the present application as provided below is broken down in the following sections.
1. Summary
2. Background
3. Brief Description of the Drawings
4. Detailed Description
4-1. The Integrative Biological Simulation Model
4-2. Testing the Biological Simulation Model on Pathologies
4-3. Testing the Biological Simulation Model on the Endocrine System
4-4. The Endobiogenic Medical Assistant (EMA™)
4-5. Conclusions
5. Evaluation Guidelines
6. Claims
7. Abstract

1. SUMMARY

Various example embodiments of the present invention may be summarized as follows:

A. A methodology is provided, which is based on an integrative approach of physiological mechanisms which support the functioning of the human body. It utilizes a Biological Simulation Model for evaluating the physiological links existing between specific biological elements measured in blood and their hormonal managers.

It permits to one establish the real state of an organism and to highlight the physiological regular phenomena and their dysfunctions, which participate in the genesis, installation and evolution of the pathology.

An amount of 35 measurements (called indexes) is shown as an illustration, with their rationale and their testing on various pathologies. Also shown is the functioning of the endocrine system through the Biological Simulation Model.

B. A data system, based on the above methodology, referred to herein without loss of generality as the Endobiogenic Medical Assistant (EMA™), is provided to assist the practitioner both on clinical and physiological evaluation, with an automated physiological diagnostic assistant (illustrated in this document) highlighting both the main dysfunctions and their required correcting actions. The therapeutic is also assisted with a menu of recommended treatments on clinical symptomatic findings and physiological actions. A "Walkthrough a Consultation" example is included in the document to illustrate how the system may operate.

The system also serves as a tracking tool to follow up progress on the patient state and verify the validity of the diagnostic and the efficiency of the selected therapy.

2. BACKGROUND

Exemplary embodiments of the present invention provide a Biological Simulation Model and associated apparatus, method and computer-readable storage medium for evaluating a patient ("exemplary" as used herein referring to "serving as an example, instance or illustration").

Exemplary embodiments of the present invention consider the organism as a whole, made of elements in permanent interaction and working together as a network. It quantifies the physiological relationships at organ and organism-level that drive the functioning of the body, and it helps identify the underlying dysfunctions linked with a disease and their evolution with or without treatment. It goes beyond the symptomatic approach of the disease and takes into account the state of the patient in its overall functioning, the so called "terrain" of the patient, which plays a key role in the ability of an individual to face a disease. For example, exemplary embodiments of the present invention facilitate an understanding of why an individual faced with a very cold weather will contract pneumonia, while similar cold weather had no effect on the individual a year earlier. Similarly, for example, exemplary embodiments of the present invention facilitate an understanding of why out of ten people faced with very cold weather under similar conditions, one will contract sinusitis, two will contract pneumonias, one will contract shingles, the rheumatoid arthritis of one will flare-up, while the other five will not contract anything.

The disease may be viewed not only as caused by a factor X, but may also and primarily be caused by one or more dysfunctions of the organism. In fact, the disease, as may be seen through the symptoms, may be considered the end of an internal process where the body has unsuccessfully attempted to contain the exposure. The symptom may be considered the signal that the body has failed in its attempt, and it will need to mobilize many more resources, unless it gets outside help. The Biological Simulation Model of exemplary embodiments of the present invention facilitates an understanding of what happened and identify the root causes that drove the failure of the organism.

Exemplary embodiments propose an explanation of the basic functioning of the organism, under control of the endocrine system, as the manager of the physiological phenomena that permits the life maintenance within the body, through a sequence of catabolic and anabolic metabolic activities.

Regulation of the internal environment requires a single and autonomous system manager that has the ability to interact permanently with all organs and body systems in order to direct and control all input/output transfers. This system manager also needs the ability to act for its own safeguard in order to remain efficient and manage the organism.

The endocrine system can fulfill the mission of managing the overall organism. The endocrine system is connected to all systems, and may act anywhere in the body and react to all kinds of solicitations: sensorial, metabolic or physiological. The endocrine system is able to reset the basal state (homeostasis) and to participate in its evolution; and it participates in growth, ensures cells nutrition and prioritizes the distribution of energetic resources. The endocrine system manages all factors involved in the defense system of the organism, and manages two fundamental attributes of the organism: short term and long term adaptation, which are hormone-dependent. It also has enough autonomy to correct its own deficiencies.

As an example, in the 1930s, Hans Selye described the role of the endocrine system in the body response to specific aggressions such as third-degree burns, spread-out infections, hemorrhages and the like, which were associated with identical reactions from the organism, which he referred to as the General Adaptation Syndrome (GAS).

Exemplary embodiments propose not only a global view on how the endocrine system organizes the body response to any kind of aggression (external or internal, physical, chemical, viral, emotional, etc.), but also how it manages the maintenance of the basic structure of the organism.

3. BRIEF DESCRIPTION OF THE DRAWINGS

Having thus described the invention in general terms, reference will now be made to the accompanying drawings, which are not necessarily drawn to scale, and wherein:

FIGS. 11-35, 35-1 and 35-2 illustrate portions of various example displays that may be presented during operation of the system of exemplary embodiments of the present invention.

4. DETAILED DESCRIPTION

Figure 1:
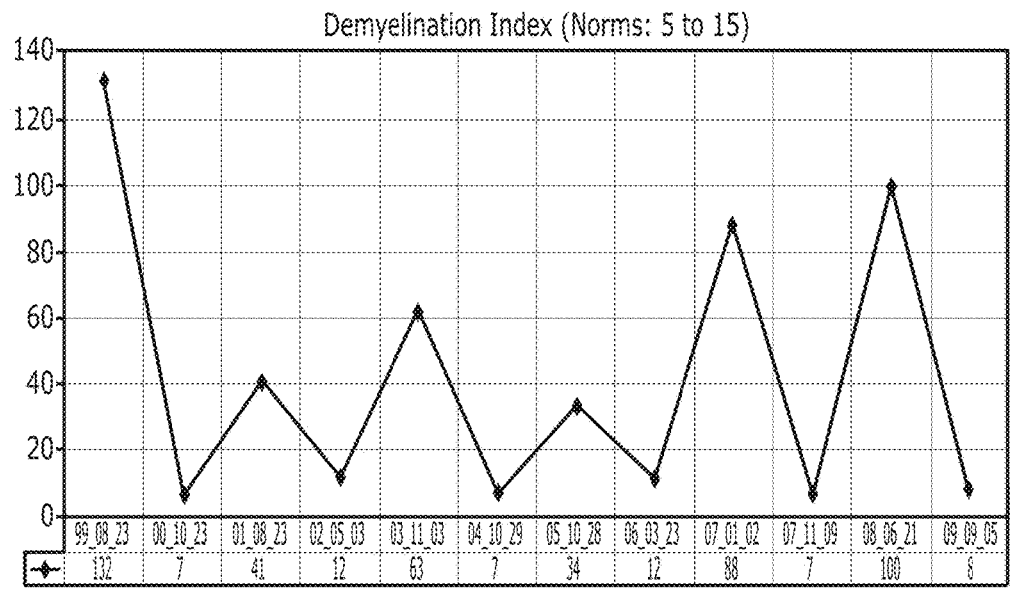
FIGS. 1-6 are graphs illustrating various data produced according to examples testing a model according to exemplary embodiments of the present invention.

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

4-1. THE INTEGRATIVE BIOLOGICAL SIMULATION MODEL

The Biological Simulation Model of exemplary embodiments of the present invention enables measurement of the overall functioning of the organism in its various aspects: endocrine, metabolic and tissue aspects, and enables such measurement at cell, organ and global level, through a series of measurements, called indexes. Through these indexes, the Biological Simulation Model may facilitate a better understanding of the physiological functioning of the organism, identifying its pathological tendencies, and/or determining of the imbalances that may be the root causes of a pathology. The Biological Simulation Model also facilitates tracking the evolution of the organism and the risks for relapses, following the efficiency of treatment, and/or identifying the side effects of a medication.

The indexes are calculated from data obtained from a single, inexpensive blood draw, and many of the indexes are based on only two to three variables, along physiological relationships identified in published research work. The simplicity of the selection is an essential factor to ensure reliability of the norms and reproducibility across patients, under similar terrain conditions, whether they are pathologic or not. The consistency with a global view of the endocrine system is achieved by defining indexes, which are mostly relative indexes, i.e., indexes which are functions of other indexes, which represent over 80% of all indexes.

An index is designed by first defining what is to be evaluated, such as a level of activity (usually relative), a yield, or a circulating rate. Relevant parameters affecting the index are then identified and selected, which parameters will be used as variables in the formulaic representation of the index. These parameters are data obtained from the blood draw, other indexes or some combination of both. Various indexes are in the form of a ratio, and in such instances, the parameters may appear in the numerator (the index "varies like") or denominator (the index "varies like the reverse") of the ratio, like in the basic formulas of physical science.

If it is desirable to differentiate the weight of two or more parameters on the same level (numerator or denominator), a mathematical differentiator may be introduced, such as a square or cubed function. Additionally, a digit number may be added, such as to maintain the index in the same band than other similar indexes. One of the objectives in the design of the indexes is to capture the relevant parameters and to select a set of formulas fully consistent with each other.

It should be noted that the indexes are designed bottom-up, born from proved physiological relationships and tested through clinical evaluation. For this reason, as well as the complexity of the human organism, there is no global index, because it would not satisfy the criteria of reliability and reproducibility.

Exemplary embodiments of the present invention also provide an apparatus and computer-readable storage medium that may assist a user in their diagnostic evaluation of a patient and in the selection of an appropriate therapy. Although exemplary embodiments of the present invention contemplate a large number of indexes, the following present examples of a number of indexes (both direct and indirect).

Blood draw (sample) data (19 data, of which 16 are used by the system):

red cells, leukocytes and their distribution (neutrophils through monocytes)

hemoglobin and platelets count

LDH (Lactate dehydrogenase), CPK (creatine phosphokinase) and TSH (thyroid stimulating hormone)

osteocalcin, alkaline phosphatases and their isoenzymes (hepatic, bone, intestine)

potassium and calcium

Examples of Indexes

1. The genital ratio measures the relative tissue activity of androgens versus estrogens, and is defined as follows: Genital Ratio=Red cells/(Leukocytes×$10^3$).

Red cells synthesis is primarily caused by androgens, which are stimulated by the luteinizing hormone (LH) from the anterior pituitary. Leukocytes, on the other hand, are under the influence of estrogens, which are stimulated by the follicle-stimulating hormone (FSH). Thus, the ratio of red cell to white cell counts (Red cells/White cells) is referred to as the genital ratio and is equal to the ratio of LH/FSH. The $10^3$ factor is required to adjust both the numerator and the denominator to the same units, such as when the red cells are expressed in millions units/$mm^3$, and white cells are expressed in thousands units/$mm^3$.

PUBLICATIONS a. Androgens—Red cells:

M. Alen, *Androgenic Steroid Effects on Liver and Red Cells*, BJ Sports Medicine, vol. 19(1), pp 15-20, March 1985.

N Hara et al., *Decline of the Red Blood Cells Count in Patients Receiving Androgen Deprivation Therapy for Localized Prostate Cancer*, Division of Urology, Dept of Regenerative and Transplant Medicine, Niigata University, Niigata, Japan, Urology, vol. 75, issue 6, pp. 1441-45, June 2010.

b. Estrogens—Leukocytes:

R. C. Crafts M.D., *Effects of Estrogens on the Bone Marrow of Adult Female Dogs*, Dept of Anatomy, Boston University School of Medicine, Boston, Mass., USA, American Society of Hematology, Blood 1948 vol. 3, pp 276-285.

Y Zheng et al., *Immuno-Histochemical Characterization of the Estrogens-Stimulated Leukocytes Influx in the Immature Rat Uterus*, Dept of Obstetrics and Gynecology, Division of Reproductive Biology, The University of Pennsylvania Medical School, Philadelphia, USA Journal of Leucocyte Biology, vol. 44, pp 27-32 (1988).

2. The genito-thyroid (GT) index measures the thyroid response to the estrogenic demand, and is defined as follows: Genito-Thyroid Ratio Index=Neutrophils/Lymphocytes, both variables of which may be expressed in percentages. The granulocytes secretion (neutrophils represent 90% of granulocytes which include neutrophils, eosinophils and basophils) is typically under the influence of estrogens, while the lymphocytes are under TSH influence. Thus, the ratio of neutrophils to lymphocytes represents the thyroid response to the estrogenic demand, and not the reverse.

The paradox here comes from the TSH which is the upper level stimulation of the thyroid and usually varies like the reverse of the thyroid activity. If TSH is medium to low, the thyroid is usually strong, and vice versa; if the TSH is medium to high, the thyroid response to the estrogenic demand is usually low.

PUBLICATIONS a. Estrogens—Neutrophils (Granulocytes):

R. C. Crafts M.D., *Effects of Estrogens on Number of Neutrophils in Bone Marrow of Adult Female Dogs*, Dept of Anatomy, Boston university School of Medicine, Boston, Mass. U.S.A., American Society of Hematology Blood vol. 3 No 3, pp 276-285 (1948).

S. A. Robertson et al., *Ovarian Steroid Hormones Regulate Granulocyte Macrophage Colony*, Dept of Obstetrics and Gynecology, University of Adelaide, South Australia, PubMed PUBMI 8838016.

Notably the R.C. Crafts publication is the same as indicated above as Neutrophils are part of the Leukocytes (or White Cells). The summary of the publication in fact reads as follows: "Large doses of estrogens have a profound effect on the bone marrow of adult dogs. The initial reaction is a great increase in the number of Neutrophilic elements in the bone marrow. These neutrophils are released into the blood stream, causing a marked rise in the total white cells count."

b. Lymphocytes—TSH:

T. Mukuta et al., *Activation of T Lymphocyte Subsets by Synthetic TSH Receptor*, Dept of Medicine, Wellesley Hospital, University of Toronto, Ontario, Canada, Journal Clinical Endocrinol. Metab. 80 (4), pp. 1264-72 (April 1995).

3. The adaptation ratio measures the relative activity of the ACTH hormone in its adaptative function relative to FSH, and is defined as Adaptation Ratio=Eosinophils//Monocytes=ACTH//FSH.

Under stimulation of ACTH, glucocorticoids (cortisol) reduce the circulating rate of eosinophils through sequestration in the spleen and the lungs (Thorn test). Conversely, an increase of eosinophils, a characteristic of a congestion phase, will indicate a shortage of glucocorticoids, hence an elevation of the upper level stimulating hormone, the ACTH. The eosinophils will vary like ACTH.

The monocytes are depending on the estrogenic response to a FSH stimulation, and are inhibited by estrogens, hence the lower are estrogens the higher are monocytes and FSH, and the monocytes will vary like FSH.

The initial physiological link of the General Adaptation Syndrome is thus characterized by the link between ACTH and FSH.

By definition, the ratio eosinophils//monocytes will be called Adaptation Ratio and it will be equal to ACTH//FSH, representing the response of FSH to ACTH. Adaptation Ratio represents both the level of the aggression and the response of the organism to the aggression: the lower is the adaptation index, the higher is the aggression and usually the higher is the glucocorticoid response (cortisol) generating a sharp reduction of eosinophils, consistent with a low adaptation ratio.

PUBLICATIONS

N. Sabag et al., *Cortisol-Induced Migration of Eosinophils to Lymphoid Organs*, Laboratory of Experimental Endocrinology, Department of Experimental Morphology, University of Chile Medical School, Santiago Norte, Casilla 21104, Correo 21, Santiago, Chile, Cellular and Molecular Life Sciences, vol. 34, no. 5, pp. 666-67, May 1978.

R. R. de Mowbray et al., *ACTH in Diagnosis of Adrenal Insufficiency (THORN Test)*, Guy's hospital and Chelsea Hospital for Women, U.K., British Medical Journal, vol. 1 (4800) pp 17-21 (January 1953).

H. Selye, *The General Adaptation and the Diseases of Adaptation*, Journal of Clinical Endocrinology & Metabolism, vol. 6, no. 2, pp. 117-230 (1946).

M. A. Giembycz et al., *Pharmacology of the Eosinophils*, Imperial College School of Medicine at the National Heart and Lung Institute, London, U.K., Pharmacological Reviews, vol. 51, no. 2, pp 213-340.

J. E. Cox & F. H. A. Mohamed, *Studies of Pituitary-Adrenal-Testis Interaction in Sheep. II. The Effects of Repeated Injections Of Adrenocorticotrophic Hormone Outside The Breeding Season*, Division of Equine Studies and Farm Animal Surgery Department of Veterinary Clinical Science University of Liverpool Veterinary Field Station Leahurst, Neston, South Wirral, L64 7TE, U.K., Therionology (1988) April; 29(4): pp. 867-72.

4. The starter index measures the relative activity of glucagon versus adrenaline and is defined as follows: Starter index=Leukocytes mobilization/Platelets mobilization.

Notably, the normal reaction to a stress situation is an adrenaline discharge via the beta sympathetic. It is the General Adaptation Syndrome which blocks the cell access to energy except in sensitive areas such as brain and heart, which need extra energy. It is the so-called immediate mobilization which distributes energy where it is most needed. At the end of the aggression, an insulin discharge will drive back to the original state (homeostasis).

When the organism is faced with a lasting or chronic aggression, it will choose the glucagon route via the alpha sympathetic along the stimulation path alpha→CRF-→TRH→ pancreas→glucagon, with glucose discharge which will increase glycaemia, generating an increase in metabolism. It is so called mediate mobilization, which is an anticipation over the General Adaptation Syndrome. In a situation of pathologic aggression, the organism will always choose the glucagon route to increase its energy reserves.

The mobilization of the leukocytes out of the splanchnic reserve will be triggered via the alpha sympathetic→glucagon route, while the platelets mobilization out the splanchnic reserve will be triggered via the beta sympathetic→adrenaline route, hence the starter definition to measure the relative activity of glucagon versus adrenaline.

5. The Cata-Ana index measures the relative part of the catabolic activity versus the anabolic activity of the organism, and represents the mobilization of factors participating in the set-up of the immediate defense system, within the general adaptation syndrome. The Cata-Ana index is defined as Cata-Ana Index=Genito-thyroid Ratio/Genital Ratio× Starter index.

The genito-thyroid index represents the catabolic response of the thyroid to the anabolic estrogenic demand during the general adaptation syndrome. The Cata-Ana index varies like the Genito-thyroid ratio.

The Genital ratio tends to decrease in case of an aggression, by the mobilization of leukocytes and acts as an amplifying factor, while the Starter, depending whether the response is an adrenaline driven defense (immediate mobilization) or a glucagon driven defense (mediate aggression) will be an amplification factor or a moderating factor. In case of a pathologic aggression, a higher starter will tend to reduce the cata-ana in relative terms since the glucagon route may assist the glucocorticoid response. The Cata-Ana index will vary like the reverse of the Genital ratio and the Starter index.

The product Genital Ratio×Starter index, is also defined as the Adjusted Genital ratio and it measures the Genital ratio, when excluding the effect of adaptation.

6. The cortisol index measures the cortisol activity of the adrenal gland and its excretion during the adaptation syndrome, and is defined as follows: Cortisol Index=Cata-Ana Index/Adaptation Ratio.

As indicated above, the Cata-Ana index measures the relative catabolic versus anabolic activity and represents the initial response to an aggression. The cortisol activity will vary like the Cata-Ana index.

As also indicated above, the adaptation ratio equals the ACTH/FSH ratio. ACTH is the stimulating hormone of the cortisol, and hence, ACTH varies like the reverse of cortisol. That is, the lower the ACTH, the lower the adaptation ratio and the higher the cortisol activity. The Cortisol index will vary like the reverse of the adaptation ratio Consequently the cortisol index varies like the Cata-Ana index and like the reverse of the adaptation ratio.

7. The adrenal gland index measures the activity of the adrenal gland, which has two types of activities, namely, an adaptive activity to respond to the aggression, and a permissive activity to support the aromatization of adrenal androgens into estrogens.

The adrenal gland index is defined as:

Adrenal Gland Index=Cata-Ana Index/Genital Ratio.

In this regard, below are 2 different points to explain how the index was built:

The Cata-Ana index measures the mobilization of factors participating in the set up of the immediate defense system within the general adaptation syndrome, and hence, adrenal gland activity varies like the Cata-Ana index.

The lower the genital ratio, the stronger the estrogenic activity and the higher the permissive demand for additional aromatization from the adrenal gland activity, and hence, the adrenal gland index varies like the reverse of the genital ratio.

8. The histamine index measures the activity of histamine, an amino substance available in most tissues (particularly in lungs and liver), which triggers capillary dilatation and increases secretory activity. The histamine index is defined as follows: Histamine Index=(Eosinophils×Platelets×Genital Ratio)/Cortisol Index.

In the representation of the histamine index, the cortisol index and eosinophils vary in reverse to one another and tend to amplify histamine when cortisol decreases (hence eosinophils increase), and reduce histamine when cortisol increases (hence eosinophils decrease).

Platelets amplify the capillary dilatation (as histamine does) by their role on blood coagulation, and hence, histamine varies like platelets. And an increase in the genital ratio reflects a higher solicitation of androgens, which may increase histamine, and hence, histamine varies like the genital ratio.

PUBLICATIONS

R. W. Schayer et al., *Binding of Histamine in Vitro and its Inhibition by Cortisone*, Rheumatic Fever Research Institute, Northwestern University, Medical School, Chicago, Ill., USA, Am J Physiology (September 1956) vol. 187, no. 1, pp. 63-65.

A. P. Lima et al., *Effects of Castration and Testosterone Replacement on Peritoneal Histamine Concentration and Lung Histamine Concentration in Pubertal Male Rats*, Depts of Physiology and Morphology, Faculties of Medicine and Odontology of Ribeirao Preto, University of Sao Paulo, Ribeirao Preto, Sao Paulo, Brazil, Journal of Endocrinology (2000), vol. 167, no. 1, pp. 71-75.

9. The adaptogen index measures the type of adaptation used by the organism, and is defined by the ratio of potassium to calcium, i.e., Adaptogen Index=K/Ca.

In situations of acute stress, using the general adaptation syndrome, there is a slight increase of Calcium and a limited change in Potassium, in terms of blood content: the adaptogen index will experience a slight reduction, which will not last.

In situations of repetitive stress, on the other hand, the aldosterone will be solicited and it will trigger a reduction of Potassium, hence a decrease in the adaptogen index (K//Ca ratio).

The adaptation short cut, using beta-endorphins, will not use aldosterone, and will maintain or eventually increase the blood content of Potassium, while the Calcium blood rate will be reduced by glucocorticoids: as a consequence, the adaptogen index (K//Ca ratio) will increase.

10. The βMSH/αMSH ratio index is defined as follows: βMSH/αMSH Index=Thyroid Metabolic Index/Adaptogen Index.

Beta-MSH (βMSH) and alpha-MSH (αMSH) are melanocyte-stimulating hormones produced in the intermediate lobe of the pituitary gland and are used for reactivating the adrenal gland by increasing the number of ACTH receptors and triggering their sensitivity. They are two complementary ways to stimulate ACTH:

a. The regular cortisol regulation is done through the ACTH-cortisol route, hence βMSH and an adrenaline discharge triggered by the beta sympathetic.

b. While the required surplus in cortisol is obtained through the αMSH route, e.g., if cortisol activity is insufficient, the αMSH route will be used in greater proportion to increase the cortisol activity, triggered by the alpha sympathetic.

The βMSH/αMSH index measures the relative level of adaptation response between the normal route (acute stress using βMSH) and the short cut using αMSH, hence the use of the adaptogen index in the formula.

The formula of this index (thyroid index//adaptogen index) is a way to assess the relative strength of the beta sympathetic versus the alpha sympathetic:

1. The thyreotrope axis of the endocrine system is stimulated by the beta sympathetic, hence the βMSH/αMSH index varies like the metabolic activity of the thyroid (thyroid metabolic index).
2. βMSH/αMSH index increases in regular stress (with an increase of aldosterone and decrease of potassium, i.e., a decrease in the adaptogen index), while it decreases in the adaption short cut, as indicated above (with an increase of potassium and decrease of calcium, i.e., an increase of the adaptogen index), hence the βMSH/αMSH index varies like the reverse of the adaptogen index.

11. The metabolic estrogens index measures the metabolic activity of estrogens, and is defined as follows: Metabolic Estrogens Index=TSH/Osteocalcin.

TSH stimulates estrogens metabolic activity, and hence, the metabolic estrogens index varies like TSH.

Osteocalcin participates in the osseous anabolism under the stimulation of estrogens. The measured osteocalcin is a blood content, and therefore, the lower the osteocalcin in blood, the higher its participation in the osseous anabolism, and vice versa, hence the metabolic estrogens index varies like the reverse of osteocalcin.

By extension, the ratio TSH//osteocalcin measures the metabolic activity of estrogen.

PUBLICATIONS a. TSH—Estrogens:
A. De Lean et al., *Sensitizing Effect of Treatment with Estrogens on TSH Response to TRH*, Medical Research Group in Molecular Endocrinology, Laval University Hospital Center, Quebec, Canada, AJP: Endocrinology and Metabolism, vol. 233, Issue 3, E235-E239, 1977.
I. M. Spitz et al., *The Thyrotropin (TSH) Profile in Isolated Gonadotropin Deficiency: A Model to Evaluate the Effect of Sex Steroids on TSH Secretion*, Population Council, New York, N.Y., USA, Dept of Endocrinology & Metabolism, Shaare Zedek Medical Center and Hebrew University, Hadassah Medical School, Jerusalem, Israel, Journal of Clinical endocrinology & Metabolism, vol. 57, No 2, 415-420.
E. Marquese et al., *The effect of Droloxifene and Estrogen on Thyroid Function in Postmenopausal Women*, Department of Medicine, Brigham and Women's Hospital, Harvard Institute of Medicine, Boston, Mass., USA, Journal of Clinical endocrinology & Metabolism, vol. 85, No 11 4407-4410.
D. D. Abech et al., *Effects of Estrogen Replacement Therapy on Pituitary Size, Prolactin and TSH concentrations in Menopausal Women*, Faculdad de Medicina, Universidad de Culaba and Porto Alegre, Brazil, Gynecology Endocrinology, vol. 4, 223-226 (2005).

b. Estrogens—Serum osteocalcin and Osteoblast proliferation:
D. C. Williams et al., *Effects of Estrogen and Tamoxifen on Serum Osteocalcin Levels in Ovariectomized Rats*, Bone Biology Research Group, Lilly Research Laboratories, Indianapolis, Ind. 46285, USA, Bone Miner: 1991 Sep. 14 (3) pp 205-220.
M. Nasu et al., *Estrogen Modulates Osteoblast Proliferation and Function Regulated by Parathyroid Hormone in Osteoblastic SaOS-2 Cells: Role of Insulin-Like Growth Factors (IGF)-I and IGF-Binding Protein-5*, Third Division, Department of Medicine, Kobe University School of Medicine, 7-5-1 Kusonoki-cho, Chuo-ku, Kobe 650, Japan, Journal of Endocrinology (2000) 167, pp 305-313.

12. The metabolic androgens index measures the metabolic activity of androgens, and is defined as follows: Metabolic Androgens Index=Metabolic Estrogens Index× Adjusted Genital Ratio, as per the above definition of the Adjusted Genital ratio, excluding the impact of adaptation. This covers the total metabolic activity of androgens at structure level, i.e., prior to the adaptation impact.

13. The growth index measures the activity of the Growth Hormone (GH) and is defined as follows: Growth index=AP Bone Isoenzymes//Osteocalcin.

Alkaline phosphatases bone isoenzymes represent the anabolism growth, as stimulated by estrogens, which target for 80% the osseous growth and for 20% the muscular growth. By extension, it may be assumed that growth-hormone GH activity varies like the bone isoenzymes.

Osteocalcin participates in the osseous anabolism, under the stimulation of estrogens. As previously noted, the measured osteocalcin is a blood content, and accordingly, the lower is the osteocalcin in blood, the higher is its participation in the osseous anabolism, and vice versa. GH activity varies like the reverse of osteocalcin

PUBLICATIONS

Anna G. Nilsson, *Effects of Growth Hormone Replacement Therapy on Bone Markers and Bone Mineral Density in Growth Hormone-deficient Adults*, Department of Medical Sciences, University Hospital, Uppsala, Sweden, Horm Res 2000 (54) pp 52-57.
H. Tobiume et al., *Serum Bone Alkaline Phosphatase Isoenzyme Levels in Normal Children and Children with GH Deficiency: A Potential Marker for Bone Formation and Response to GH Therapy*, Department of Pediatrics, Oyakama University Medical School, Okayama 700, and Diagnostic Development SRL Inc, Tokyo 163-08, Japan, The Journal of Clinical Endocrinology & Metabolism, vol. 82, N) 7 pp 2056-2061 (1997).
A. R. Baker et al., *Osteoblast-Specific Expression of Growth Hormone Stimulates Bone Growth in Transgenic Mice*, Department of Endocrine Research, Genentech Inc., South San Francisco, Calif. 94080, USA, Mol Cell Biol. 1992 December; 12(12) pp 5541-5547.

14. The bone remodeling index measures the level of bone remodeling and the degree of alteration of bone and bone cartilage, and it is defined as follows: Bone Remodeling Index=TSH×Growth Index.

Bone remodeling varies like the growth index as the growth index expresses the metabolic activity of the growth hormone.

Similarly, bone remodeling varies like TSH as the TSH stimulates estrogens in their contribution of growth activity, primarily towards osseous growth.

PUBLICATIONS

C. Ohisson et al., *Growth Hormone and Bone*, Research Centre for Endocrinology and Metabolism, Sahlgrenska University Hospital, Goteborg, Sweden, Endocrine Reviews 1998 Feb. 1, vol. 19(1), pp. 55-79.

K. Brixen et al., *Growth Hormone (GH) and Adult Bone Remodeling: The Potential use of GH in Treatment of Osteroporosis*, Department of Endocrinology and Metabolism, Aarhus University Hospital, Denmark, J Pediatry Endocrinology 1993 January-March; 6(1) pp 65-71.

15. The thyroid metabolic index measures the level of metabolic activity of the thyroid gland in its ability to provide the organism with the required energetic elements, and this index is defined as follows: Thyroid Metabolic Index=LDH/CPK.

LDH (Lactate dehydrogenase) and CPK (Creatine phosphokinase) are two enzymes that block insulin access to cells by increasing insulin resistance. Both enzymes reside in muscles and hence reduce their blood content, but they react differently:

a. CPK is typically more impacted than LDH in reaction to an increase of metabolic activity because it is immediately mobilized, and hence, its blood content will be reduced.

b. On the other hand, LDH is typically slower to move and may require an extended adaptation effort to reduce its blood content.

This differentiation in the impact of the thyroid hormones on both enzymes gives an opportunity to quantify the extent of thyroid metabolic activity by the ratio LDH II CPK: the higher the thyroid activity, the lower the CPK blood content and the higher the thyroid metabolic index.

PUBLICATION

Alice Muller et al., *Effects of Thyroid Hormone on Growth and Differentiation of L6 Muscle Cells*, Laboratory for physiology, Institute for cardiovascular research, Free University Amsterdam, The Netherlands. BAM 3 (1): 59-68, 1993.

16. The thyroid yield measures the ratio of the thyroid metabolic activity versus the pituitary level of solicitation (TSH), and it is defined as follows: Thyroid Yield=Thyroid Metabolic Index/TSH. By definition, the ratio of the thyroid metabolic index to TSH expresses the yield of the thyroid in terms of metabolic activity. A low TSH may be associated with a strong thyroid yield, and conversely, a high TSH may be associated with a low thyroid yield.

17. The parathormone (PTH) index measures the level of activity of the parathormone, a hormone produced by the parathyroid glands and secreted when the blood content of calcium is abnormally low. The parathormone primarily serves two tasks:

a. At bone level, it mobilizes the bone calcium by favoring osteolysis of the bone tissue to liberate calcium and phosphatases and increasing osteocalcin blood content.

b. At kidney level, it favors phosphatases elimination by the kidney.

The PTH index is defined as: PTH Index=Ca×Osteocalcin/Thyroid Yield Index. The PTH index varies like Ca (calcium) and Osteocalcin since their blood content increases with parathormone.

The thyroid has an osteolytic effect similar to the parathormone: if the thyroid yield is high, the parathormone does not need to act and conversely. PTH will vary like the reverse of the Thyroid yield.

18. The osteoclasic index measures the relative part of the osteoclasic activity of the thyroid, and it is defined as: Osteoclasic Index=LDH/AP Bone Isoenzymes.

The osteoclasic activity is a catabolic activity (bone destruction).

The index expresses the ratio of LDH, a catabolic action, over the alkaline phosphatases bone isoenzymes, an anabolic indication, of the bone remodeling activity.

Thus, the lower the AP bone isoenzymes, the higher the osteoclasic activity.

The osteoclasic index varies like LDH and like the reverse of the AP bone Isoenzymes.

PUBLICATIONS

C. Gudmundson et al., *Isoenzymes of Lactic Dehydrogenase and Esterases in Regenerating Bone*, Department of Orthopaedic Surgey, Malmô General Hospital, University of Lund, Malmö, Sweden, Acta Orthopaedica, 1971, vol. 42, No 4, pp 297-304.

C. Gudmundson et al., *Enzyme Studies of Fractures with Normal and Delayed Union*, Department of Orthopaedic Surgery, Malmö General Hospital, University of Lund, Malmo, Sweden, Acta Orthopaedica, 1971, vol. 42, No. 1, pp 18-27.

Arthur R. Henderson, M. B., Ph.D. et al., *Increased Synthesis of Lactate Dehydrogenase "H" Subunit by a Malignant Tumor*, Clin. Chem. 20/11 (1974), pp 1466-1469.

19. The osteoblastic index measures the relative part of the osteoblastic activity of the thyroid, and it is defined as: Osteoblastic Index=CPK/Osteocalcin.

The osteoblastic activity is an anabolic activity (bone remodeling).

This index expresses the ratio of CPK, an anabolic activity (stimulates the creation of adenosine triphosphate ATP, a source of immediate energy for muscles) over osteocalcin blood content, which will reduce when the osteoblastic activity is high, and vice versa.

The osteoblastic index varies like CPK and like the reverse of Osteocalcin.

PUBLICATIONS

B. Fournier et al., *Stimulation of Creatine Kinase Specific Activity in Human Osteoblast and Endometrial Cells by Estrogens and Anti-Estrogens and its Modulation by Calciotropic Hormones*, Ciba-Geigy Ltd, Basel, Switzerland, Journal of Endocrinology, 1996, August; 150(2), pp 275-285.

T. Yoshikawa et al., *In Vitro Bone Formation Induced by Immunosuppressive Agent Tacrolimus Hydrate (FK506)*, Department of Orthopedic Surgery, Nara Medical University, Kashihara, Japan, Tissue Eng. March/April 2005, 11(3-4), pp 609-617.

20. The turnover index measures the length of the cell renewal cycle in terms of the time it takes to get a cell renewal. The higher the turnover index, the slower the renewal, and the lower the turnover index, the faster the renewal.

The turnover index is defined as: Turnover Index=TSH×AP Bone Isoenzymes.

TSH indirectly expresses the catabolic activity, necessary for any cell renewal activity. The lower the TSH, the stronger the thyroid, the faster the renewal and the lower the turnover index, hence the turnover varies like TSH.

Relative to the Alkaline phosphatases bone isoenzymes, cell renewal is a catabolic activity and the slower the renewal, the higher the turnover, the higher the anabolism, hence the turnover index varies like the alkaline phosphatases bone isoenzymes, which represents the anabolic activity, particularly in the osseous area (alkaline phosphatases bone isoenzymes hydrolysis organic phosphatases to produce indissoluble mineral phosphatases, hence their notable role in the calcification, at joints level, and in the mineralization of the skeleton).

In summary the Turnover varies like the product TSH×AP Bone Isoenzymes.

21. The intra-cellular growth index measures the level of intra-cellular activity of growth factors, and is defined as follows: Intra-cellular Growth Index=Growth Index/Turnover Index.

The intra-cellular growth index varies like the growth index, adjusted by the speed of cell renewal (turnover index). Thus, when turnover is low (hence fast renewal), the intra-cellular growth activity is high; and conversely, when the turnover is high (hence slow renewal), the intra-cellular growth activity is low.

22. The anti-growth index measures the level of activity of the anti-growth factors, and is defined as: Anti-growth Index=1/Intra-cellular Growth Index. As reflected in the formula, the anti-growth index varies like the reverse of the intra-cellular growth index. That is, the higher the intra-cellular growth index, the lower the anti-growth activity (and anti-growth index), and vice versa.

23. The somatostatin index measures the level of activity of the somatostatin and provides a way to assess the overall activity of the exocrine pancreas. The somatostatin index is defined as: Somatostatin Index=Anti-growth Index/Cortisol Index.

The somatostatin hormone is a strong inhibitor of the growth hormone, as per the research studies referred below. It is one of the main anti-growth factors and it varies like the anti-growth index.

Cortisol increases growth hormone receptors activity, as per research studies referred below, while somatostatin has a reverse effect on the same receptors, and consequently, the somatostatin index varies like the reverse of the cortisol index.

PUBLICATIONS

F. R. Ward et al., *The Inhibitory Effect of Somatostatin on Growth Hormone, Insulin, and Glucagon secretion in Diabetes Mellitus*, Depts of Reproductive Medicine and Medicine, School of Medicine, University of California, San Diego, La Jolla, Calif., USA, Journal of Clinical Endocrinology & Metabolism (1975), vol. 41, No 3, pp 527-532.

P. Brazeau et al., *Inhibition of GH Secretion in the Rat by Synthetic Somatostatin*, The Salk Institute for Biological Studies, La Jolla, Calif., U.S.A., Journal of Endocrinology (1974), vol. 94, No 1, pp 184-187.

D. Swolin-Eide et al., *Cortisol Increases Growth Hormone Receptor Expression in Human Osteoblast-Like Cells*, Research Center for Endocrinology and Metabolism, Dept of Internal Medicine, and Dept of Hand Surgery, Sahlgrenska University Hospital, Goteborg, Sweden, Journal of Endocrinology (1998), vol. 156, Issue 1, pp 99-105.

A. Schonbrunn, *Glucocorticoids Down-Regulate Somatostatin receptors on Pituitary cells in Culture*, Department of Physiology, Harward school of Public Health, Boston, Mass., USA, Journal of Endocrinology (1982), vol. 110, No 4, pp 1147-1154.

A. P. Silva et al., *Regulation of CRH-Induced Secretion of ACTH and Corticosterone by SOM230 (Somatostatin Analogue) in Rats*, Novartis Institute for BioMedical Research, Basel, Switzerland, European Journal of Endocrinology (2005), vol. 153, Issue 3, pp 7-10.

24. The prolactin index measures the functional activity of the prolactin. This hormone plays a notable role in the reactivation of the adaptation process, influencing catabolism and anabolism, growth and anti-growth factors, at cell and tissue levels.

The prolactin index is defined as: Prolactin Index=Somatostatin Index×TSH/Growth Index.

The prolactin index varies like the somatostatin index in that prolactin is part of the somatotropic axis and plays a role in balancing growth and anti-growth. It inhibits Growth hormone, hence it varies like the reverse of Growth index.

Prolactin is stimulated by TRH, hence it varies like TSH, also stimulated by TRH.

25. The insulin index measures the functional activity of insulin and is defined as: Insulin Index=100×Cata-Ana Index/TSH×Turnover Index.

The insulin, in its role of bringing immediate energy through the initial adaptation syndrome, varies like the Cata-Ana index, which represents the mobilization of factors participating in the set-up of the immediate defense system.

Insulin acts also along the thyroid in its role of mobilizing energetic reserves, and hence, it varies like the reverse of TSH (a strong TSH, hence a weak thyroid, inhibits insulin; and conversely, a weak TSH, hence a strong thyroid, increases insulin).

A third role of insulin is to increase cell nutrition to support cell renewal and growth, and hence, it varies like the reverse of the turnover index: a low turnover is a sign of fast cell renewal hence an increase of cell nutrition and an increase of insulin, conversely, an increase of turnover decreases insulin activity.

The factor 100 has been added to maintain the index in a band-with similar to other related indexes.

Consequently, the insulin index varies like the Cata-Ana index and like the reverse of TSH and Turnover, with an adjustment factor of 100.

PUBLICATIONS

V. Lafargia et al., *The Effects of Insulin on TSH Secretion and the Morphology and Physiology of the Thyroid in the Lizard Podarcis Sicula*, Department of Comparative Biology, Universita degli Studi di Napoli, Naples, Italy, Amphibia-Reptillia (1996), vol. 17, no. 1, pp. 39-45.

R. P. Lamberton et al., *Insulin Hypoglycemia Suppresses TSH Secretion in Man*, Tufts New England Medical Center Hospital, Boston, Mass., USA, Hormone and Metabolic Research, vol. 18, no. 1, pp. 76-77 (1986).

26. The insulin resistance index measures the inhibition level of the insulin activity at the membrane level, independent of its temporary activity linked with the general adaptation syndrome. It is defined as: Insulin Resistance Index=Somatostatin Index/Insulin Index.

As insulin resistance is a growth hormone inhibitor at the cell level, the insulin resistance index varies like somatostatin.

Conversely, the Insulin resistance index varies like the reverse of insulin, outside of adaptation (the insulin resistance index decreases when insulin is high in order to facilitate the glucose access to cells, and it increases when insulin is low).

In instances of stress, Insulin resistance may selectively prevent glucose access to cells in non-priority organs in order to secure the energy distribution to priority organs (heart, brain, muscles).

27. The demyelination index measures the adaptative activity of insulin in its timing relationship to the adaptative activity of the growth hormone, and it is defined as: Demyelination Index=Insulin Index/(Growth Index×Intra-cell Growth Index).

The demyelination index expresses the chronology insulin-growth factors, i.e., the demyelination increases when insulin anticipates on growth factors, under the influence of glucagon.

Also present in the demyelination index, the growth index and the intra-cell growth index: both express the same thing in terms of growth hormone activity or in terms of cell growth. They amplify the demyelination risk (the lower the growth hormone or the intra-cell growth, relative to insulin, the higher the demyelination risk).

28. The next number of example indexes describes the cell activity between the nucleus and the membrane, as well as the various types of cellular death. These indexes include a nuclear/membrane index, membrane expansion rate, structural expansion rate, membrane fracture rate, apoptosis rate, necrosis rate and fibrosis rate.

28-1. The nuclear/membrane index measures the level of metabolic activity of the nucleus relative to the membrane activity, and is defined as: Nuclear/Membrane Index=Metabolic Estrogens Index/Growth Index.

The focus target of estrogens metabolic activity is the nucleus, while the focus target of the growth hormone metabolic activity is the membrane.

By definition the nuclear/membrane index is the ratio of the estrogens metabolic activity index over the growth hormone activity index, which has a respective impact on cell Nucleus and membrane.

28-2. The membrane expansion rate measures the metabolic activity of the membrane, and is defined as: Membrane Expansion Rate=Catabolism Rate×Intra-cell Growth Index.

In this index, the catabolism rate is the starting point of any cell membrane expansion, and the intra-cell growth index represents the intra-cell activity of growth factors.

Both indexes have an amplification impact on the Membrane expansion.

A strong membrane expansion rate represents a strong dominance of growth factors over structural factors: the higher it is and the higher is the risk of membrane fracture leading to necrosis (see below).

Notably, the catabolism rate is yet another index, which is defined as the ratio of the thyroid metabolic index to the adrenal gland index (Catabolism Rate=Thyroid Metabolic Index/Adrenal Gland index).

In this regard, catabolism depends almost in large part upon the thyroid metabolic activity, and logically it varies like the thyroid metabolic index.

Also, adrenal hormones favor both anabolism through adaptation and catabolism through permissivity over the thyroid. The adrenal gland index functions as a moderating factor in the catabolism rate index since a strong glucocorticoid response usually generates an hypo-catabolism, hence the catabolism rate varies like the reverse of adrenal gland activity.

28-3. The structural expansion rate measures the metabolic activity of the nucleus. The structural expansion rate index is defined as follows: Structural Expansion Rate=Anabolism Rate Index×Nuclear/Membrane Index.

For this index, the anabolism rate, which represents the anabolism metabolic activity driven by estrogens over the nucleus, is defined by Catabolism rate/Cata-Ana Index. The nuclear/membrane index represents the level of metabolic activity of the nucleus relative to the membrane activity. And similar to the membrane expansion rate, both above indexes have an amplification impact on the structural expansion rate.

28-4. The membrane fracture rate measures the degree of fragility of the membranes and hence their risk of fracture. It is defined as: Membrane Fracture Rate=Metabolic Yield Index/(TSH×Turnover Index).

Overall metabolic activity is required to support a membrane expansion, and as such, the membrane fracture rate varies like the overall metabolic yield which is the sum of both catabolic and anabolic activities.

Membrane fracture also requires strong thyroid activity, the higher the thyroid throughput, the lower the TSH—and hence, the membrane fracture rate varies like the reverse of the TSH.

Finally, membrane fracture is the consequence of a fast cell renewal (the faster the cell renewal, the lower the turnover). And consequently the membrane fracture rate varies like the reverse of the Turnover index.

28-5. The apoptosis rate measures the level of apoptosic activity for the whole organism. It is an indication of nucleus overactivity and acceleration of cell growth process. The apoptosis rate increases when the cell growth is normal, and decreases when the cell growth is abnormal or when the organism is in a deceleration of growth. The apoptosis rate is defined as: Apoptosis Rate=Structural Expansion Rate/Membrane Expansion Rate.

The structural expansion rate represents the metabolic activity of the nucleus (the higher the structural expansion rate, the higher the likelihood the cell is in a programmed death, for a limited number of divisions. Apoptosis, which measures the cell programmed death activity, varies like the structural expansion rate.

Apoptosis varies like the reverse of the membrane expansion rate. The higher the membrane expansion rate, the lower the apoptosis and the higher the risk of membrane fracture (with cell implosion leading to necrosis instead of apoptosis), and vice versa.

28-6. The necrosis rate measures the level of cellular implosion by necrosis relative to apoptosis. It is the other type of cellular death, with waste, generally associated with local inflammation. The necrosis rate is defined as: Necrosis Rate=Membrane Fracture Rate/Apoptosis Rate. As necrosis is a consequence of membrane fracture, the necrosis rate varies like the membrane fracture rate. And as the definition of the necrosis rate is relative to apoptosis, the necrosis rate varies like the reverse of the apoptosis rate.

28-7. The fibrosis rate measures the fibrosis activity of the organism, from a simple isolation of a tissue to a degenerative sclerosis of a set of tissues or an organ. Fibrosis is part of the growth process: it participates in organ growth in order to prevent excessive growth. The fibrosis rate is defined as: Fibrosis Rate Index=$(TSH)^2 \times (Osteocalcin)^3/100$. In this formula, the power used for both TSH and osteocalcin differentiates the relative weight of both components in the measurement of the fibrosis activity. The 100 denominator keeps the index in a normal bandwidth relative to other indexes.

The fibrosis rate varies like the TSH. In this regard, as fibrosis is an anti-growth factor, it is typically favored by a weak thyroid, and hence, a strong TSH.

Similarly, fibrosis rate varies like the reverse of bone osteocalcin. A strong fibrosis is linked with an imbalance of the calcium metabolism associated with a decrease of the osteocalcin in the fibrosed area, hence an increase of the osteocalcin blood content. Fibrosis will vary like the osteocalcin blood content.

Having introduced a number of example indexes of the Biological Simulation Model, the following discussion presents a number of example cases in which one or more indexes have been tested in relation to one or more pathologies, some of which also illustrate the effects of classical treatments on the indexes.

4-2. TESTING THE BIOLOGICAL SIMULATION MODEL ON PATHOLOGIES

As described herein, testing the Biological Simulation Model on pathologies may be sub-divided as follows:
4-2-1. Testing One Index and One Pathology:
Example Case 1: Histamine index and Eczema,
Example Case 2: Histamine index and Rhinitis,
Example Case 3: Demyelination index and Multiple Sclerosis,
Example Case 4: Insulin index and Cystic fibrosis,
Example Case 5: Insulin resistance index and Down syndrome,
Example Case 6: Bone remodeling index and Bone metastases, and
Example Case 7: Bone remodeling index and Osteoporosis.
4-2-2. Evaluation of Classical Treatments:
Example Case 8: LH RH analogues over FSH/LH and androgens,
Example Case 9: Chemotherapy over Histamine, and
Example Case 10: Cortisone on Chronic allergy (asthma).
4-2-3. Multiple Patients with One Pathology: Example Case 11: Fibromyalgia (20 sick versus 20 healthy).
4-2-4. Major Relevant Indexes for a Given Pathology:
Example Case 12: Metastasized Colon cancer, and
Example Case 13: Metastasized Prostate cancer.
4-2-1: Testing One Index and One Pathology
In the following seven example cases, one index has been tested in relation to one pathology.

Example Case 1: Histamine Index and Eczema

In this first example, consider the case of a six-year-old female suffering from generalized eczema at the time of her first consultation on Apr. 30, 2003. The patient's father is cutaneous allergic, and the patient has been previously diagnosed with asthma (treated by Becotide and Ventoline) and chronic rhinopharyngitis. The patient was first diagnosed with generalized eczema at age eighteen months, and had previously been treated (without success) with local corticoids.

Following her first consultation, the patient was given a terrain treatment and experienced a complete healing in two months. Her healing was confirmed by blood analysis at a second consultation on Sep. 27, 2003, at which time her histamine index levels also dropped to within designated normal levels for a female, as reflected in the below table.

| | Date | | Female Norms | |
|---|---|---|---|---|
| | 2003 Apr. 30 | 2003 Sep. 27 | Mini W | Maxi W |
| Histamine Index | 387 | 55 | 20 | 60 |

PUBLICATION

J. Ring, *Plasma Histamine Concentrations in Atopic Eczema*, Dermatology Department, Ludwig Maximilians University Munich, West Germany, Clin Allergy, 1983 November, 13(6): pp 545-52.

Example Case 2: Histamine Index and Allergic Rhinitis

In a second example, consider the case of a forty-two-year-old female at the time of her first consultation in January 2003. Since puberty, the patient has suffered from a chronic rhinitis with seasonal allergic symptoms. The patient has received various treatments (corticoids, antiallergic drugs, beta-stimulants) with limited success. But chronicity has increased through time, with symptoms becoming permanent, such as full nasal obstruction, postnasal drips and very frequent sneezing.

Analysis of the patient's blood work shows a very high histamine index at 1085 versus designated norm levels for a female from 20 to 60. An appropriate treatment reduced the index by eighty-five percent over a year period: the signs of rhinopharyngitis have fully disappeared and the patient feels a complete healing. No relapse during a six-year period following the patient's first consultation. The data below illustrate the patient's histamine index at her first consultation, and at second and third subsequent consultations—the second and third consultations occurring approximately four months and one year, respectively, after the first consultation.

| | Date | | | Female Norms | |
|---|---|---|---|---|---|
| | 2003 Jan. 13 | 2003 May 12 | 2004 Jan. 5 | Mini W | Maxi W |
| Histamine Index | 1085 | 889 | 157 | 20 | 60 |

PUBLICATION

A. Weyer et al., *Seasonal Increase of Spontaneous Histamine Release in Washed Leukocytes from Rhinitis Patients Sensitive to Grass Pollen*, Unité d'Immuno-Allergie, Institut Pasteur, Paris, France, Clin Exp Immunol, 1990 March, 79(3): 385-391.

Example Case 3: Demyelination Index and Multiple Sclerosis

In a third example, consider the case of a twenty-eight-year-old male who since 1993 has suffered from chronic sensitivity disorders at the level of limbs and thorax, a type of multiple sclerosis (MS). The patient has experienced chronic relapses of symptoms requiring corticoid treatment over short period of time. In July 1995, the patient suffered retrobulbar optic nevritis on his left eye, which was treated by high-dose corticosteroid embolization. And beginning in 1998, the patient has been treated with Interferon Beta since 1998, one injection per week.

As can be seen in the graph of FIG. 1, the demyelination index for this patient is strictly correlated with the time of activation of the pathology, i.e., August 99, August 01, November 03, October 05, January 07 and June 08.

PUBLICATION

*Cortical Demyelination and Diffuse White Matter Injury In Multiple Sclerosis*, Kutzelnigg A, Lucchinetti C F, Stadelmann C, Brück W, Rauschka H, Bergmann M, Schmidbauer M, Parisi J E, Lassmann H., Center for Brain Research, Medical University of Vienna, Vienna, Austria, Brain, 2005 November; 128(Pt 11): 2705-12. Epub 2005 October 17.

Example Case 4: Insulin Index and Cystic Fibrosis

In a fourth example, consider the cases of two patients previously diagnosed with cystic fibrosis, and a third patient experiencing similar insulin index levels.

The first case is of a five-year-old male diagnosed with cystic fibrosis at the age of two. As shown in the table below, the trend of the insulin index over a five and one-half year period shows a stable picture at a very low level. More particularly, the trend shows that the insulin index averages 10% of the designated normal levels (1.5 to 5.0), with nearly identical levels at beginning of the period (0.15 in November 2003) and end of the period (0.12 in May 2009).

| | (Mini/Maxi Norms: 1.5 to 5.0) | | | | | |
|---|---|---|---|---|---|---|
| Case 1 | November 2003 | November 2004 | October 2005 | May 2006 | May 2007 | May 2009 |
| Insulin index | 0.15 | 0.08 | 0.25 | 0.32 | 0.12 | 0.12 |

The second case is of a four-and-one-half-year-old female diagnosed with cystic fibrosis at the age of one. As shown in the table below, the insulin index is below the designated normal levels (1.5 to 6.0) at the time of her first consultation and tends to decrease gradually through time over a four-year period.

| | (Mini/Maxi Norms: 1.5 to 5.0) | | | | | |
|---|---|---|---|---|---|---|
| Case 2 | July 2005 | July 2006 | June 2007 | May 2008 | June 2009 | November 2009 |
| Insulin index | 1.05 | 0.34 | 0.28 | 0.20 | 0.45 | 0.30 |

And the third case is of a seventeen-year-old female not previously diagnosed with cystic fibrosis. As shown in the table below, the insulin index for this patient is also significantly below the designated normal levels (1.5 to 6.0), confirming the two previous cases of cystic fibrosis with low insulin activity, and being confirmed by Research studies, as stated below

| | Date | Male/Female Norms | |
|---|---|---|---|
| | January 1999 | Mini | Maxi |
| Insulin index | 0.45 | 1.5 | 5 |

PUBLICATION

E. M. Laursen et al., *Diminished Concentrations of Insulin-Like Growth Factor I in Cystic Fibrosis*, Dept of Growth and Reproduction GR, State University Hospital, Copenhagen, Denmark, Arch Dis Child 1995; 72:494-497 doi: 10.1136/adc.72.6.494.

Example Case 5: Insulin Resistance and Down Syndrome

In a fifth example, consider the case of a male with Down syndrome. As shown in the table below, the patient has an insulin resistance index that consistently trends at very high levels relative to the designated normal levels, at least in the in the early phase of childhood, confirmed by Research studies as stated below.

| | Date | | | | Male Norms | |
|---|---|---|---|---|---|---|
| | January 2007 | May 2008 | January 2009 | September 2009 | Min | Max |
| Age (years) | 2 | 3$^{5}/_{12}$ | 4¼ | 4$^{5}/_{6}$ | | |
| Insulin Resistance | 13212 | 307 | 1163 | 1050 | 0.75 | 1.25 |

PUBLICATIONS

E. J., Hoorn et al., *Insulin Resistance in an 18-Year-Old Patient with Down Syndrome Presenting with Hyperglycaemic Coma, Hypernatraemia and Rhabdomyolysis* (*Case Report*), Erasmus Medical Center, Rotterdam, The Netherlands, Journal of internal medicine, 2005, vol. 258, no 3, pp. 285-288 [4 page(s) (article)] (19 ref.).

C. T. Fonseca et al., *Insulin Resistance in Adolescents with Down Syndrome: A Cross Sectional Study*, Medicina School, HUCFF, Federal University of Rio de Janeiro, Brazil, Genetics dept, IPPMG, Ilha de Fundao, Rio de Janeiro, Brazil, Pediatrics Dept, HUCGG, Ilha de Fundao, Rio de Janeiro, Brazil, Endocrinology Dept, HUCFF, Ilha de Fundao, Tio de Janeiro, Brazil, *BMC Endocrine Disorders* 2005, vol. 5 PubMed doi:10.1186/1472-6823-5-6.

Example Case 6: Bone Remodeling and Osseous Metastases

In a sixth example, consider the cases of two patients. The first patient was, at the time of his first consultation in July 2000, a fifty-nine-year-old male diagnosed seven years prior with prostate cancer undergoing hormonotherapy treatment. In July 2000, the patient was suffering from paraplegia of the lower extremities, with destruction of D9 vertebra and compressive external pachymeningitis. Generalized osseous metastases is discovered and treated with radiotherapy. The patient died in November 2000, approximately four months following his first consultation.

As shown in the table below, the patient's bone remodeling index surged from the patient's first consultation through two subsequent consultations, thereby giving an indication of the speed of the cancer osseous expansion.

| | Date | | Male Norms | |
|---|---|---|---|---|
| | July 2000 | August 2000 | October 2000 | Mini | Maxi |
| Bone Remodel Index | 43 | 33 | 115 | 2.5 | 8.5 |

At the time of his first consultation in January 2007, the second patient was a sixty-four-year-old male. Eight years earlier, in October 1998, a PSA control yielded a level of 85 ng/ml (norm<5.0), indicating a poorly-differentiated prostate adenocarcinoma, with extension to the right seminal vesicle. The patient was treated with radiotherapy of forty-five grays over the prostate and twenty-five grays over the pelvis area. In December 1998, a lymphadenectomy revealed a contaminated ilio-obturator lymph node, for which the patient was treated with a single injection of LH RH analogue for three months, and then Casodex (three capsules per day) for several years. Then, in July 2006, the patient's PSA level showed a gradual increase, leading to additional radiotherapy on the pelvic area (eight sessions).

At the time of the second patient's first consultation in January 2007, the patent was suffering from multiple metastases concerning ureters with bilateral pulmonary metastases. Approximately eleven months thereafter, in December 2007, the patient died following a renal blocking secondary to the bilateral ureteral metastatic obstruction. The table below shows the bone remodeling index for the second patient for a portion of the final year of the patient's life. As shown, the bone remodeling index trend shows some temporary improvement during 2007, until the organism started escaping from the treatment in October 2007.

| (Male Norms: 2.5 to 8.5) | | | | | | |
|---|---|---|---|---|---|---|
| Date | January 2007 | March 2007 | May 2007 | August 2007 | September 2007 | December 2007 |
| Bone Remodel Index | 62 | 36 | 25 | 16 | 17 | 80 |

Example Case 7: Bone Remodeling and Osteoporosis

In a seventh example, consider the case of a fifty-five-year-old female at the time of her first consultation in May 2009. For approximately four years prior, beginning in 2005, the patient had undergone hormone replacement therapy for menopause, and undergone Utrogestan, Estrogel, vitamin D and calcium treatment for spinal osteoporosis, although her initial bone remodeling was normal. In August 2009, the patient suffered a crush fracture of her T6 vertebra with low bone mineral density diffused through the entire vertebral body.

Figure 2:
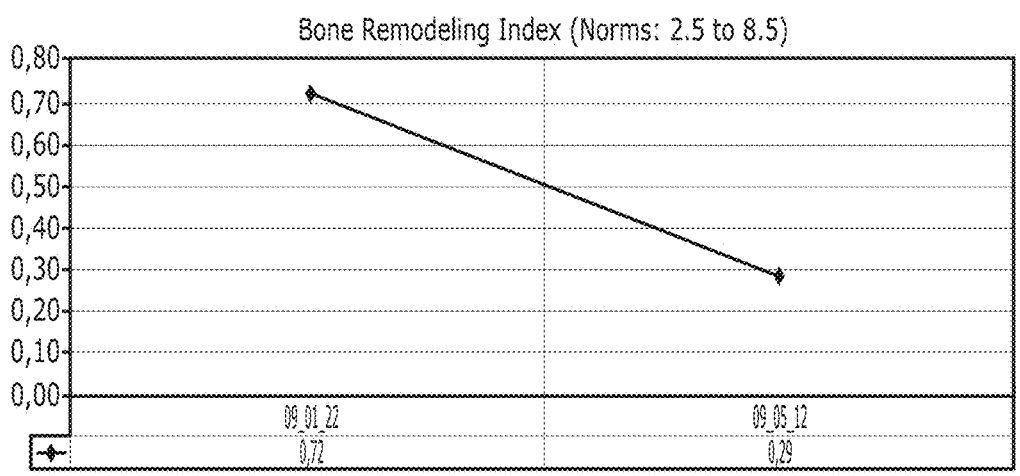

As shown in the graph of FIG. 2, for a period of approximately four months before the patient suffered the crush fracture, the patient's bone remodeling index decreased from an already low level of 0.72 in January 2009 to 0.29 in May 2009 (from norm levels between 2.5 and 8.5)—explaining the crush fracture that the patient would suffer approximately three months later.

The table below illustrates the results of an osteodensitometry procedure performed on the patient approximately four months after she suffered the crush fracture. The procedure confirmed the magnitude of bone loss. The patient's Bone Mineral Density (BMD) tested at 0.651 g/cm2, which is 25% lower than the average woman of the patient's same age (−2.0 Standard Deviations SD).

| Osteodensitometry (Dec. 4, 2009) | cv (%) | BMD (g/cm2) | T Score (SD) | Z Score (SD) | Percentile (%) |
|---|---|---|---|---|---|
| Thigh Bone | | | | | |
| total zone | 0.8 | 0.874 | −1.3 | −0.5 | 31 |
| cervical zone | 1.7 | 0.66 | −1.9 | −0.6 | 27 |
| ward zone | 2.6 | 0.515 | −2.3 | −0.5 | 31 |
| Forearm | | | | | |
| ultra distal zone | 1 | 0.36 | −0.5 | 0 | 50 |
| proximal zone | 1.5 | 0.658 | 0.2 | 0.9 | 82 |
| Front rachis exam | 0.9 | 0.651 | −3.4 | −2 | 2 |
| BMD observed | | 0.651 | | | |

PUBLICATIONS

*Bone Remodeling in Osteoporosis,*
M. C. de Vernejoul,
INSERM U18, Hôpital Lariboisière, 6 rue Guy Patin, 75010 Paris, France,
Clinical Rheumatology, vol. 8, Supplement 2/June 1989.
*Bone Marrow, Cytokines, and Bone Remodeling—Emerging Insights into The Pathophysiology Of Osteoporosis,*
S C Manolagas, M.D., Ph.D., and R L Jilka, Ph.D., Dept of Internal Medicine, University of Arkansas for Ledical Sciences, Little Rock, USA, The new England Journal of Medicine, vol. 332:305-311, No 5, Feb. 2, 1995.
4-2-2: Evaluation of Classical Treatments The following next three example cases illustrate the effects of classical treatments on the indexes.

Example Case 8: Effects of LH RH Analogs (Decapeptyl/Triptorelin/Leuprolide) Treatment Over FSH, LH and Androgens In this eighth example, consider the case of a sixty-two-year-old male at the time of his first consultation in December 2008. In April 2004, the patient underwent a radical prostatectomy with lymph nodes dissection. The patient had also twice undergone chemotherapy treatment, first using Taxotere® for a three-month period from August to November 2006, and then using Zometa® for a three-month period from May to August 2007. In December 2007, approximately a year before his first consultation, the patient was also diagnosed with multiple osseous metastases, which had been treated with Sutent® (37.5 mg/day).

Figure 3:
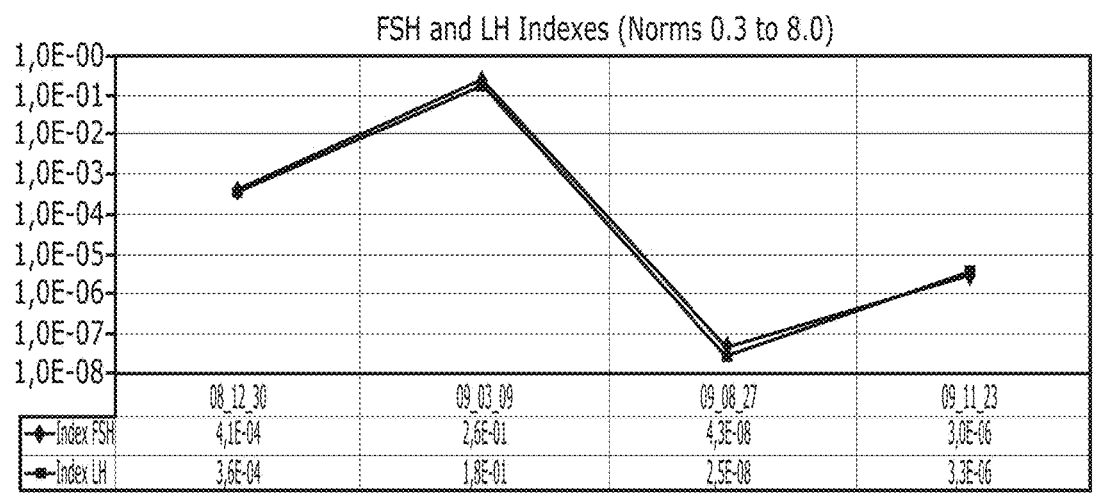
Figure 4:
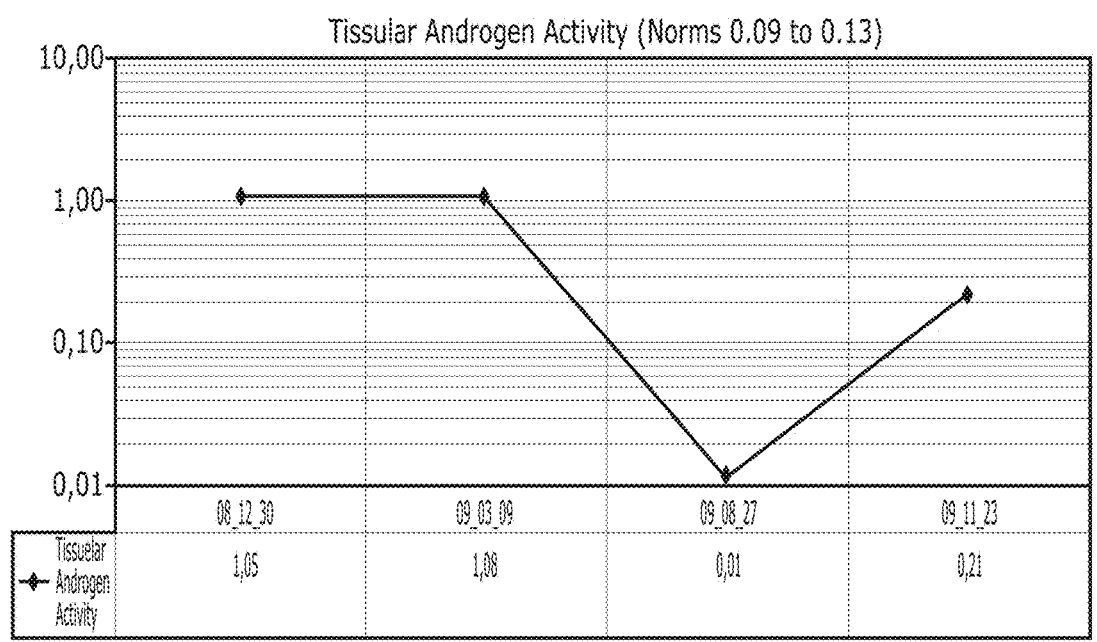
Figure 5:
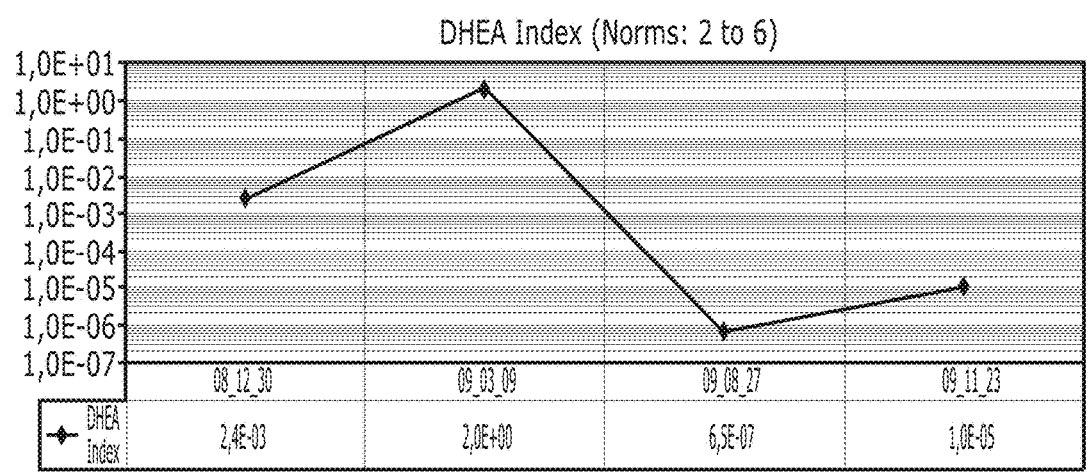

The graphs of FIGS. 3, 4 and 5 show the blocking effects of an injection of Decapeptyl (Triptorelin) given Jun. 1, 2009 (about six months after the patient's first consultation), over FSH, LH, tissue androgenic and DHEA activities.

FIG. 3 illustrates FSH and LH indexes (norms 0.3 to 8.0). Both curves show the effect of the Triptoreline injection on June 1st reducing by a factor E7 between March and August, with a rebound in November, when the injection is 6 months old.

FIG. 4 illustrates tissue androgen activity (norms 0.09 to 0.13), and shows a similar kind of drop from 1.08 to 0.01 between March and August, with a rebound in November when the injection is 6 months old.

FIG. 5 illustrates the DHEA activity index (norms 2 to 6), and shows a similar kind of drop from 2.0 to 6.5 E-7 between March and August, with a rebound in November, when the injection is 6 months old.

PUBLICATIONS

*Comparative Efficacy of Triptorelin Pamoate and Leuprolide Acetate in Men with Advanced Prostate Cancer,*
South African Triptorelin Study Group: C F Heyns, M L Samonin, P Grosgurin, R Schall. C H Porchet,
Dept of Urology University of Stellenbosch, Tygerberg Hospital, Western Cape, South Africa,
Debiopharm S A, Lausanne, Switzerland,
Quintiles ClinData, Bloemfontein, South Africa,
BJU international, 2003, vol. 92, n°3, pp. 226-231.
*Leuprolide Acetate: A Drug of Diverse Clinical Applications,*
A C Wilson, S Vadakkadath Meethal, R Bowen, C S Atwood,
Dept of Medicine and Geriatric Research, University of Wisconsin, Madison Wis., USA,
Dept of Pathology and Laboratory Medicine, Madison Wis., USA,
ORB Research, Charleston S.C., USA,
Case Western University, Cleveland Ohio, USA,
Expert Opinion on Investigational Drugs, vol. 16, no. 11, November 2007, pp. 1851-1863(13).
*Comparative Efficacy of Triptorelin Pamoate and Leuprolide Acetate in Men with Advanced Prostate Cancer,*
South African Triptorelin Study Group: C F Heyns, M L Samonin, P Grosgurin, R Schall. C H Porchet,
Dept of Urology University of Stellenbosch, Tygerberg Hospital, Western Cape, South Africa,
Debiopharm S A, Lausanne, Switzerland,
Quintiles ClinData, Bloemfontein, South Africa,
BJU international, 2003, vol. 92, n°3, pp. 226-231.
*Leuprolide Acetate: A Drug of Diverse Clinical Applications,*
A C Wilson, S Vadakkadath Meethal, R Bowen, C S Atwood,
Dept of Medicine and Geriatric Research, University of Wisconsin, Madison Wis., USA,
Dept of Pathology and Laboratory Medicine, Madison Wis., USA,
ORB Research, Charleston S.C., USA,
Case Western University, Cleveland Ohio, USA,
Expert Opinion on Investigational Drugs, vol. 16, no. 11, November 2007, pp. 1851-1863(13).

Example Case 9: Chemotherapy and Histamine Induction in a Cancer Patient

In a ninth example, consider the case of a female who in June 2002, at the age of forty seven, underwent a full right breast mastectomy, with axillary curage of four metastatic lymph nodes with capsule tear, among six identified lymph nodes (4N+/4R+/6). As to the patient's histology: she had an infiltrating ductal carcinoma SBR (Scarff-Bloom-Richardson) grade 1, 4 cm long, concerning the area behind the nipple and external quadrants, and infiltrating the nipple, with colonization of the epidermis on surface. The patient also had a noticeable a small infiltrating carcinoma 8 mm long at a distance of the external quadrants junction. The limits of ablation were healthy tissue.

An immune-histochemical analysis showed that the infiltrating carcinoma was Estrogen Receptor negative and slightly Progesterone Receptor positive.

In addition, between August and November 2002, the patient underwent adjuvant chemotherapy treatment made of six cycles, based on Adriamycin (86.5 mg), Ifosfamide (1165 mg) and Taxotere® (130 mg) within a BCIRG005 protocol. The patient did not take any other medication or undergo any other treatment, including cortisone, antiemetic or stimulating of bone marrow.

Figure 6:
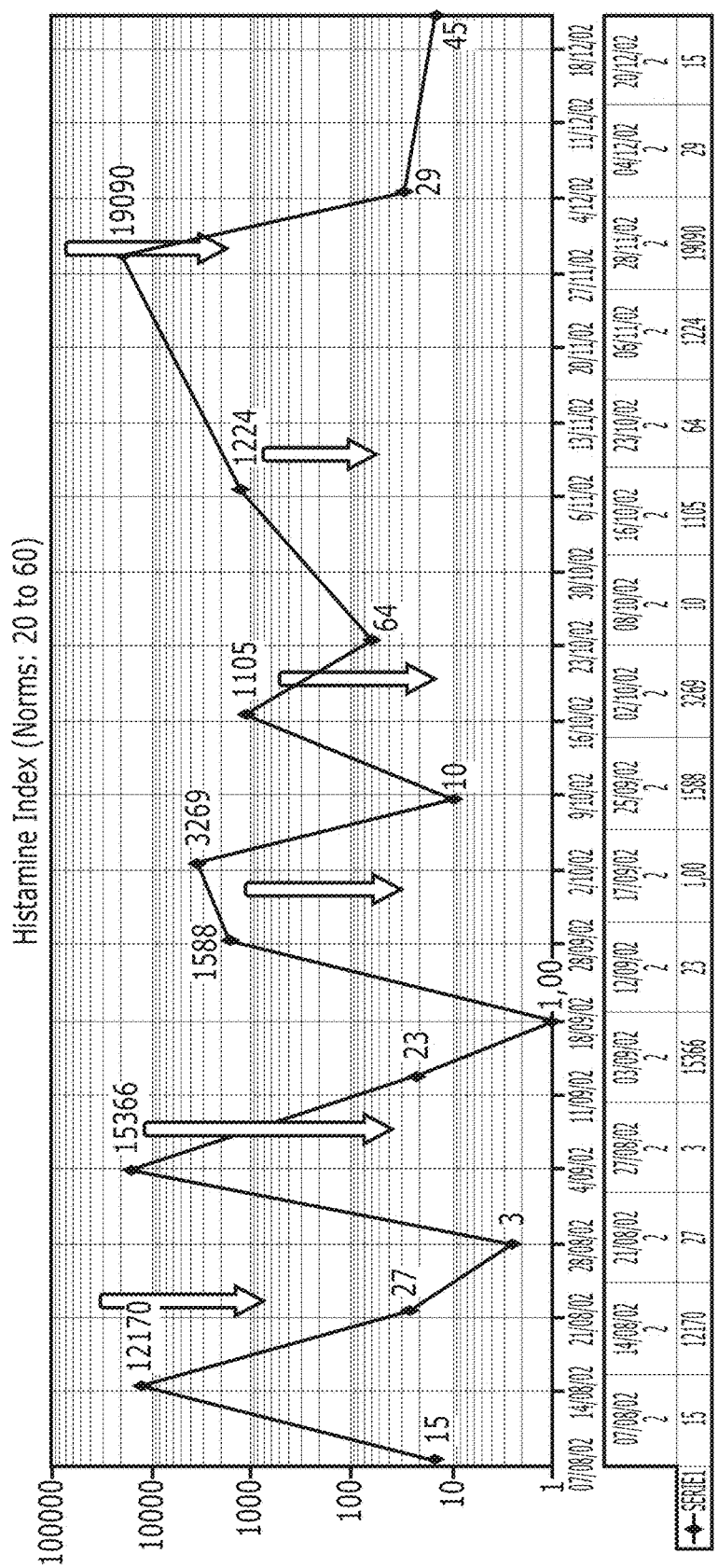

FIG. 6 illustrates the patient's histamine index over a period of time, with the arrows indicating the dates of the patient's chemo sessions. As shown, the dates of the chemo sessions are indicated by arrows on the graph (August 8, August 29, September 19, October 10, October 31, November 21, all 2002).

The illustrated histamine index trend shows a peak after perfusion and a subsequent return to the basal state, which is getting more and more difficult through time, until the chemotherapy ends. This may open new opportunities for tracking patients under chemotherapy treatment. In this regard, the time to get to the peak of the histamine reaction and its intensity may permit one to identify a patient's risks to strong histaminic reactions with their associated effects (e.g., nauseas, vomiting, cephalalgias, various allergies, etc.) and, if desired, apply a corrective complementary therapy.

PUBLICATION

*Effect of Paclitaxel (Taxol) and Its Solvent Cremophor EL on Mast Cell Histamine Secretion and Their Interaction with Adriamycin,*
G Decorti, B F Klugman, L Candussio, L Baldini,
Department of Biomedical Sciences, Faculty of Medicine, Trieste, Italy,
Anticancer Res 1996 January-February, vol. 16, No 1, pp 317-320.

Example Case 10: Effect of Cortisone on Chronic Allergy (Asthma)

In a tenth example, consider the case of a sixty-two-year-old female with osteoporosis and multiple food intolerances, and who has suffered from asthma since childhood. The patient is given cortisone (60 mg/day) for two months prior to a consultation on Apr. 19, 2010. The patient's related index evolution between Jan. 26, 2010 and Apr. 19, 2010, and the consultation looks as follows:

| Index | 2010 Jan. 26 | 2010 Apr. 19 | Female Norms Mini | Female Norms Maxi |
|---|---|---|---|---|
| Cortisol | 0.4 | 14.5 | 3 | 7 |
| ACTH | 676004 | 0.25 | 0.7 | 3 |
| DHEA | 251080 | 4 | 5 | 9 |
| Adaptation Ratio (Eosinophils) | 3.30 22.1 | 0.16 1.3 | 0.25 1 | 0.5 5 |
| Histamine | 11969 | 15 | 20 | 60 |
| Bone Remodeling | 8 | 27 | 2.5 | 8.5 |
| Parathormone | 16.9 | 3.1 | 2 | 42 |

As shown in the above table, as a consequence of the cortisone treatment, the cortisol jumps by a very large factor (over 30). Example embodiments of the present invention can detect a high level of cortisol without measuring it in the blood. Relative to the ACTH index, physiological studies (as referred below) have demonstrated that an upsurge in cortisol blocks the ACTH, which may be identified by example embodiments without measuring it in blood. As also shown, DHEA being under control of ACTH, the DHEA index sharply declines, together with ACTH, as indicated by its measurement. Further, the increase in cortisol results in a significant reduction in the eosinophils, and consequently a decrease in the histamine index. And a large increase in cortisol, through its catabolic effect on bone, may increase the bone remodeling index, coupled with a significant decrease of parathormone, in reaction to the liberation of calcium by the bone catabolism. The related indexes show a large consistency with the physiological moves identified in Research papers listed below.

PUBLICATIONS

*Alterations in Cortisol Negative Feedback Inhibition as Examined Using the ACTH Response to Cortisol Administration in PTSD,*
R Yehuda, R K Yang, M S Buchsbaum, J A Goller,
The Traumatic Stress Studies Program, Psychiatry Department, Mount Sinai School of Medicine, and the Bronx Veterans Affairs Medical Center, 130 West Kingsbridge Road, Bronx, N.Y. 10468, USA,
Psychoneuroendocrinology (2006) May; 31(4): pp 447-451.
*Effect of ACTH and Prolactin on Dehydroepiandrosterone (DHEA), Its Sulfate Ester and Cortisol Production by Normal and Tumorous Human Adrenocortical Cells,*
T Feher, K S Szalay, and G Szilagyi,
Hungarian Academy of Sciences, Postgraduate Medical School and Semmelweis University Medical School, Budapest, Hungary,
Journal Steroid Biochemistry (1985) August; 23(2): pp 153-157.
*Eosinophils Activate Mast Cells to release Histamine,*
A M Piliponsky, D Pickholtz, G J Gleich, F Levi-Schaeffer,
Dept of Pharmacology, School of Pharmacy, The Hebrew University-Hassad Medical School, Jerusalem, Israel,
Dept of Immunology, Mayo Clinic and Foundation, Tochester, Minn., USA,
Int. Arch Allergy Immunology (1999) 118, N) 2-4, pp 202-203.
*Profiles of Endogenous Circulating Cortisol and Bone Mineral in Healthy Elderly Men,*
E. Dennison, P. Hindmarsh, C. Fall, S Kellingway, D Barker, D Philips and C Cooper,
Medical Research Council Environmental Epidemiology Unit, University of Southampton, Southampton General Hospital, Southampton, UK,
Cobbold Laboratories, Middlesex Hospital, London, UK,
The Journal of Clinical Endocrinology & Metabolism (1999),
Journal of Endocrinology (2009) 201, pp 241-252 Vol 84, No 9, pp. 3058-3063.
*Cortisol Mobilizes Mineral Stores from Vertebral Skeleton In The European Eel: an Ancestral Origin for Glucocorticoid-Induced Osteoporosis,*
M Sbaihi, K Rousseau, S Baloche, F Meunier, M Fouchereau-Peron, and S Dufour, Museum Natioal d'Histoire Naturelle, Paris, France, Marine Station of Concarneau, Concarneau, France.

4-2-3: Multiple Patients with One Pathology Example
Case 11: Study of Fibromyalgia Cases versus Healthy Cases (2×20) In the following eleventh example case, multiple patients with one pathology are evaluated. In this example, consider a sampling of twenty females aged between 30 and sixty (with one-third from 40 to 50) who suffer from fibromyalgia, and a similar sampling of twenty healthy females. In the patients with fibromyalgia, the most commonly-observed symptoms include: muscular pains and inflammatory lesions, abdominal pains, insomnia, headaches, anxiety and depression, gastro-oesophageal reflux disease (GERD) and chronic fatigue.

The Biological Simulation Model of example embodiments of the present invention identified in the patients with fibromyalgia a number of areas of endocrine imbalance, as illustrated in the below table. For example, these patients had an excess of aldosterone that may create swellings and peripheral edemas, and an excess of peripheric serotonin (shortage of central serotonin) that may create depression, migraines, headaches headaches and gastro-intestinal troubles (GERD). These patients also exhibited the following: a shortage of somatostatin (hypo function of exocrine pancreas), an excess of insulin, relative to insulin resistance, an excess of intra-cell insulin activity: high cell permeability and osmolarity, and an excess of oxidoreduction and free radicals.

| | Median Values | | Female Norms | |
|---|---|---|---|---|
| Index | Healthy | Fibromyalgia | Mini | Maxi |
| Aldosterone | 756 | 10818 | 77 | 2688 |
| Peripheral Serotonin | 5.1 | 26.2 | 1.5 | 7.5 |
| Somatostatin | 1.9 | 0.5 | 1.5 | 5.0 |
| Insulin versus Insulin resistance | 2.9 | 43.8 | 2 | 4 |
| Intra-cell insulinic activity (cell osmolarity) | 4.6 | 47.9 | 8 | 12 |
| Oxidoreduction | 0.4 | 2934 | 0.7 | 2.0 |
| Free Radicals excess | 10 | 4848 | 2 | 6 |

This eleventh example illustrates the multiplicity of the dysfunctions underlying the broad scope of the fibromyalgia syndrome observed in a group of patients. For a given patient, the distribution of the relevant indexes, coupled with the clinical examination, may permit one to develop the appropriate therapeutic. For example, a patient may be treated to reduce aldosterone if the patient is suffering from swellings and peripheral edemas, and/or treated with supporting central serotonin if the patient is suffering from neurologic troubles (depression, headaches, etc.). The majority of patients suffer from metabolic troubles associated with a cell over nutrition affecting the muscles, associated with a hypo functioning of the exocrine pancreas (low somatostatin), and coupled with an excess of oxidation and free radicals. For fibromyalgia, as for kinds of syndromes, example embodiments of the present invention permit an extended study of the pathology, which affects a large part of the population, by working on much larger samples in order to break the broadly called "fibromyalgia syndrome" in homogeneous pathology subsets, with repeatable symptoms and dysfunctions, which permits to associate adequate therapeutics.

4-2-4: Major Relevant Indexes for a Given Pathology
The following example cases evaluate the major relevant indexes for a given pathology.

Example Case 12: Evolution of a Metastasized Colon Cancer

In a twelfth example, consider the case of a forty-six-year-old female with the following antecedents: cousin diagnosed with rectum cancer at age 50, paternal grandmother diagnosed with colon cancer at age 50, and maternal aunt diagnosed with breast cancer and colon cancer at age 60. On Jul. 9, 2008 a right colon tumor (tubulovillous adenocarcinoma stage T1-M2, with lymph nodes metastases (5)) was identified through a colonoscopy. Then, on Jul. 29, 2008, the patient underwent a right ileocolectomy, which was followed by chemotherapy (six cycles of Folfox) ending in February 2009. On Jun. 2, 2009, the patient underwent a thoraco-abdomino-pelvic scan, from which three hepatic lesions were identified in the right side of liver (confirmed three days later by a PET scan). The patient was then again given chemotherapy treatment (three cycles of Folfori-Avestin), ending in July 2009. On Aug. 27, 2009, the patient underwent a right hepatectomy to clear metastases from the colon cancer, and from Sep. 15, 2009 to Feb. 3, 2010, the patient was yet again given chemotherapy (eleven cycles of Folfori-Avestin).

On Nov. 24, 2009, a CT scan (chest/abdomen/pelvis) of the patient came back normal, as did a similar scan on Feb. 9, 2010. On Mar. 11, 2010, however, a PET (positron emission tomography) scan showed multiple disseminated hypermetabolic lesions (retro-peritoneal, Virchow's nodes, a right hilar pulmonary and a new hepatic lesion). And on Apr. 12, 2010, a rachis MRI and a CT scan (abdomen/pelvis) showed spin bone lesions at the lumbar level, multiple disseminated hepatic and nodular lesions, compression of the intra-hepatic bile ducts and an intra-hepatic dilatation. The classical biological data and related index evolution across three milestones: July 2009, March 2010 and Apr. 2010 for this patient are shown in the below table.

|  | 2009 Jul. 16 | 2010 Mar. 8 | 2010 Apr. 15 | Mini | Maxi |
| --- | --- | --- | --- | --- | --- |
| Lab Data | | | | | |
| LDH | 347 | 438 | 787 | 266 | 500 |
| Osteocalcin | 17 | 7 | 3 | 11 | 43 |
| Alkaline Phosphatases | 37 | 243 | 860 | 35 | 104 |
| CEA | 2.6 | 3.5 | 13.3 | | 10 |
| CA 125 | 18.8 | | 178.5 | | 35 |
| SGOT | 36 | 84 | 164 | 5 | 45 |
| SGPT | 60 | 135 | 335 | 5 | 35 |
| GGT | 38 | 486 | 1273 | | 35 |
| Index | | | | | |
| Cata-Ana | 0.4 | 4.2 | 9.8 | 1.8 | 3 |
| Growth | 2 | 32 | 229 | 2 | 6 |
| Somatostatin | 16.9 | 0.4 | 0.3 | 1.5 | 5 |
| Turnover | 11 | 105 | 484 | 40 | 60 |
| Bone Remodeling | 3 | 68 | 727 | 2.5 | 8.5 |
| Metabolic Estrogen | 0.3 | 1.4 | 4.8 | 0.2 | 0.4 |
| bMSH/aMSH | 6.2 | 4.8 | 21.3 | 6 | 8 |
| Thyroid Metabolic | 4.6 | 3.8 | 15.7 | 3.5 | 5.5 |
| PTH | 6.4 | 4 | 0.6 | 2.5 | 42.4 |
| Apoptosis | 2.46 | 0.03 | 0.004 | 0.3 | 0.7 |

After eleven cycles of chemotherapy from September 2009 to Feb. 3, 2010, the patient seemed to be cancer free as evidenced by a normal CT scan (chest/abdomen/pelvis) on Feb. 9, 2010. On that basis, chemotherapy was terminated. One month later, based on March 8 data, the Biological Simulation Model of example embodiments of the present invention showed a sharp degradation of the state of the patient, a few days before the March 11 PET scan showed a spreading of the pathology.

In July 2009, there were only three small hepatic lesions on the right side of the liver, which were extracted the following month (right hepatectomy in August 2009), without other signs of extension. Classical lab data shows no out of line situation, except a slight increase of SGPT transaminases and gamma GT, consistent with the state of the liver. The Biological Simulation Model of example embodiments of the present invention, on the other hand, shows that the potential of anti-growth factors are still strong (high somatostatin at 16.9), a balanced cell renewal favoring normal cell development (low turnover and high apoptosis), and normal cellular activity (balanced beta/alpha sympathetic), without metabolic outburst (normal estrogenic and thyroid activity). These elements of the Biological Simulation Model suggest good control of the organism over the pathology.

On Mar. 8, 2010, only one month after the end of the chemotherapy, the patient suffered a sudden reactivation of the pathology, as evidenced by the radical change of the biological state of the patient. Classical biology shows an increase of LDH (347 to 438), alkaline phosphatases (37 to 243), SGOT (36 to 84) and SGPT (60 to 135) transaminases, as well as gamma GT (38 to 486), all of which indicate a serious issue at liver level. The Biological Simulation Model of example embodiments of the present invention shows an outburst of the pathology, as supported by the evolution of a number of indexes that confirm the generalized spreading of cancer. These supporting indexes include a relative increase of catabolic activity by a factor 10 (0.4 to 4.2); a boost of GH activity by a factor 16 (2 to 32); an increase in turnover by a factor of 10, favoring the development of malignant cells (11 to 205), associated with a collapse of apoptosis by a factor of 80 (2.46 to 0.03); a collapse of anti-growth factors by a factor of 40 (somatostatin 16.9 to 0.4); and a sharp increase of the bone remodeling (3 to 68), coupled with a boost of the estrogens metabolic activity (0.3 to 1.4), which indicates the development of bone metastases as later confirmed in the April 12 MRI.

On Apr. 10, 2020, the biological assessment, four weeks later, shows an outburst of the pathology and a sharp evolution within one month, raising fears of imminent death of the patient. Classical data of digestive markers shows the importance of hepatic damage: LDH is sharply up (438 to 787), as is Alkaline Phosphatases (243 to 860), SGOT (84 to 164) and SGPT (135 to 335) transaminases, gamma GT (486 to 1273) and CEA (3.5 to 13.3), with a decrease of osteocalcin blood content (7 to 3), associated with the raise of bone remodeling and metastases. The Biological Simulation Model of example embodiments of the present invention confirms the sharp degradation of the pathology and its links with hormonal dysfunctions. In this regard, the Biological Simulation Model shows an increase of the relative catabolic activity (4.2 to 9.8), and an upsurge of GH activity (32 to 229) and bone remodeling, reflecting the spreading of bone metastases. The Biological Simulation Model also shows a strong reactivation of the thyroid activity (3.8 to 15.7), triggered by the upsurge of the beta sympathetic activity (bMSH/aMSH 4.8 to 21.3), and generating a collapse of the parathormone activity (4 to 0.6). Finally, the outburst of the estrogens metabolic activity (1.4 to 4.8) indicates a large use of the last resources of the patient, coupled with a lack of anti-growth capability (somatostatin 0.4 to 0.3). All of these elements give a possible explanation of why the pathology escapes the traditional cancer therapies.

The analysis of this case shows the reliability of the information given by the Biological Simulation Model indexes, confirmed by the correlation with the information given by classical biological and radiological data (e.g., CT scan, MRI, PET scan). The multiplicity of dysfunction factors highlighted in this case raises the need of complementary therapies able not only to act on the pathology, but also to contain/correct such dysfunctions which encourage cancer spreading. The Biological Simulation Model of example embodiments of the present invention may therefore complement the classical biology measurements and permit one to understand the biological mechanisms underlying a pathology in action. This could open new therapeutic perspectives in the etiologic diagnostic of a pathology, as well as in the tracking of the evolution of the state of a patient and of the effects of ongoing treatments.

Example Case 13: Evolution of a Metastasized Prostate Cancer

The above sixth example case draws a link between the bone remodeling index and bone metastasis. Now, a thirteenth example case addresses the major indexes associated with the overall pathology (metastasized prostate cancer), and does so based on the sixty-four-year-old patient from the sixth example case. Consider the below table in which five groups of indexes have been selected for analysis. These five groups of indexes describe the evolution of the pathology and its degree of severity (death occurred two months after the last biology).

| Index | 2007 Jan. 3 | 2007 May 9 | 2007 Oct. 15 | Male Norms Mini | Male Norms Maxi |
| --- | --- | --- | --- | --- | --- |
| Cortisol | 24 | 136 | 8173 | 3 | 7 |
| Adaptation | 0.33 | 0.09 | 0.01 | 0.25 | 0.5 |
| (Eosinophils %) | 4.0 | 1.0 | 0.5 | 1.0 | 5.0 |
| Serotonin | 264 | 93 | 49900 | 1.5 | 7.5 |
| GH | 62 | 21 | 83 | 2 | 6 |
| Growth Index | 1567 | 23650 | 506730 | 40 | 1000 |
| Bone Remodeling | 62 | 25 | 80 | 2.5 | 8.5 |
| Adenosis | $10^5$ | $10^5$ | 3302 | 10 | 30 |
| Anti-Growth | 1.0 | 8.4 | 0.7 | 10 | 15 |
| Somatostatin | 0.04 | 0.06 | $9 \times 10^{-5}$ | 1.5 | 5 |
| Necrosis | 521 | 12 | 417 | 2.5 | 6 |
| Inflammation | 1695 | 58 | 28384 | 0.3 | 2.5 |
| Apoptosis Rate | $10^{-4}$ | $10^{-3}$ | $10^{-4}$ | 0.3 | 0.7 |
| Fibrosis Rate | 1.1 | 5.0 | $10^{-3}$ | 6 | 8 |
| Insulin | 13.6 | 6.0 | 153 | 1.5 | 5 |
| Insulin Resistance | $10^{-3}$ | 0.01 | $10^{-7}$ | 0.8 | 1.3 |
| Oxidoreduction | $10^6$ | 23 | $10^{11}$ | 0.7 | $10^{11}$ |
| βMSH/αMSH | 4.9 | 7.0 | 16.5 | 6 | 8 |
| Thyroid Yield | 3.7 | 6.1 | 24 | 1.5 | 2.5 |
| Cancer Expansivity | 1408 | 236 | 1806 | 0.01 | 3.2 |

The first group of indexes, including the cortisol, adaptation, eosinophils (percentage) and serotonin indexes, indicates the importance of the aggression and the huge resources provided by the adrenal gland (cortisol). The adaptation ratio accordingly reduces sharply illustrated by the eosinophils content of the leukocytes (0.1%).

The second group of indexes includes the GH, growth, bone remodelling, adenosis, anti-growth and somatostatin indexes. As to these indexes, cancer is a degenerative pathology with unlimited proliferation of malignant cells, requiring an upsurge of growth hormone activity (GH), with a sharp reduction of the anti-growth activity (including somatostatin) and an hyperplasic growth illustrated by the adenosis index.

The third group of indexes includes the necrosis, inflammation, apoptosis and fibrosis indexes. As to this third group, different cellular deaths are deeply perturbed by the pathology with a sharp reduction of apoptosis (0.0001), a surge of necrosis (416) linked with a very high inflammation and a fibrosis, initially high and collapsing (0.004) when the organism cannot any more fence the impacted area.

The fourth group of indexes includes the insulin, insulin resistance, oxidoreduction, βMSH/αMSH and thyroid yield indexes. These indexes illustrate the disorders created by the huge energy needs for the proliferation of malignant cells, in terms of insulin upsurge, with sharp reduction of insulin resistance to let the glucose access the malignant cells, the associated growth of oxidoreduction and free radicals, and an upsurge of the thyroid (3.7 to 24), triggered by a sharp increase of the betasympathetic (beta/alpha balance measured by the βMSH/αMSH index), to organize the energy distribution.

The fifth group includes one index, cancer expansivity, which illustrates the generalized proliferation of the pathology.

4-3. TESTING THE BIOLOGICAL SIMULATION MODEL ON THE ENDOCRINE SYSTEM

Figure 7:
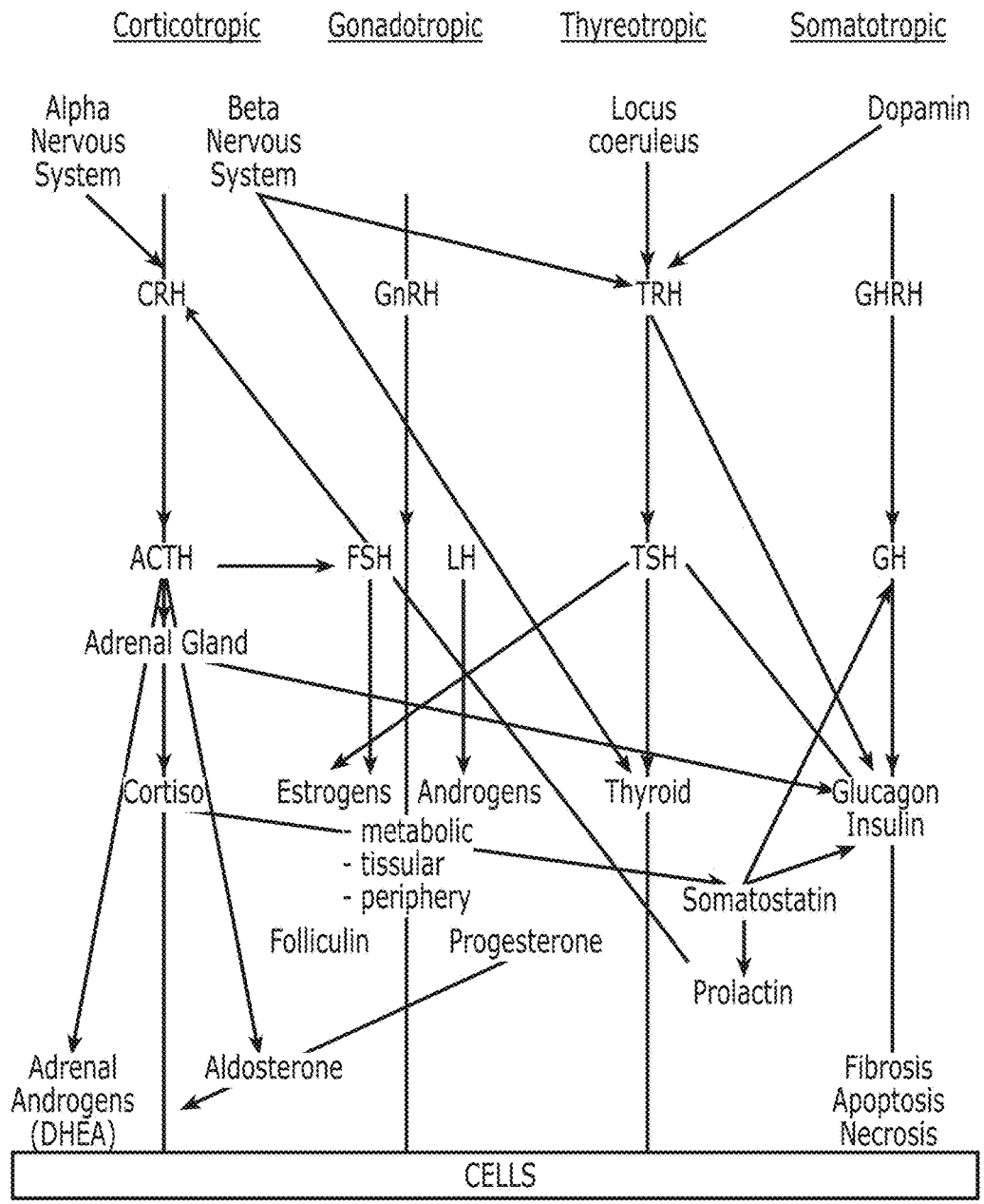
FIG. 7 is a graph of the endocrine system.

Consider the graph of the endocrine system shown in FIG. 7.

The functioning of the global metabolism of the human organism implies that the endocrine system acts along a precise sequence of catabolic and anabolic alternate phases, which repeats indefinitely.

This sequence starts from the corticotrope axis, moves to gonadotrope axis, then to thyrotrope axis and somatotrope axis, to restart indefinitely from the corticotrope axis along the same scenario, in link with the regular "vertical" activity of each of these axes, working along a similar feedback system.

The EMA™ system gives a way to evaluate the internal endocrine system relationships along vertical, horizontal and radial links.

A. The corticotropic axis plays a critical role in the energy distribution. It is the starting point of the General Adaptation Syndrome, which represents the response of the organism to internal or external aggressions. It has also a so-called permissive role in the secretion activation of other endocrine axis.

The metabolic activity of the corticotropic axis is primarily catabolic. It covers the protein metabolism (increased catabolism of muscular, osseous, cutaneous, adipic and lymphoid tissues), the carbohydrates metabolism (increases glycaemia by increasing gluconeogenesis and insulin resistance), the lipid metabolism (by decreasing the hepatic lipogenesis, and increasing Free Fatty Acids), and the hydroelectric metabolism (reduces intracell water penetration and facilitates Na+ re-absorption and K+ urinary elimination).

The physiological activity of the corticotropic axis relates to interaction with the cardiovascular system (amplifies vasoconstricting impact of catecholamines, such as adrenalin, increase sinoatrial conduction), the digestive system (increases lymphatic absorption of insoluble fats, increases gastric hyperchlorhydria), the circulatory system (increases content of neutrophils, red cells and platelets by splanchnic liberation, reduces blood content of eosinophils by sequestration in lungs or in spleen), and the nervous system (amplifies alpha sympathetic activity and reduces pituitary responses to hypothalamus hormones).

Under therapeutic influence, it amplifies anti-inflammatory and anti-allergic actions.

B. The gonadotropic axis manages the overall sexual hormones, which play a critical role on anabolism, particularly for the protein anabolism, the muscular development and the skeletal maturation.

The metabolic activity of the gonadotropic axis is strongly anabolic, with direct access on the cell nucleus. This includes, for estrogens, preparation and production of anabolism building blocks; for androgens, organization and completion of anabolism (architecture). It includes, for progesterone, intermediate role between estrogens and androgens, extend action of estrogens, delay action of androgens, both anti-estrogens and anti-androgens activities. And it includes, for adrenal androgens, lower secretion level than genital androgens, important role in 3 periods in life: puberty period (initiation of genital function), end of pregnancy (preparation of childbirth) and andropause/menopause (buffering genital secretion deficiencies).

As to the physiological activity of the gonadotropic axis, for estrogens, its predominant role is on osseous structure, stimulating growth of bone and bone cartilage. For androgens, its predominant role is on musculature, stimulating pineal growth (stature), close the epiphyseal cartilage (end of growth). And for adrenal androgens, it plays a minor role, except during puberty (construction role) and during genital pause (moderating catabolic effects of glucocorticoids).

C. The thyreotropic axis mobilizes the energy reserves of the organism by increasing the basic metabolism, and acts upon the somatotrope axis to initiate the reconstruction phase. The role of the thyroid is to support catabolism, in order to bring to all levels of the organism the necessary materials required for the anabolic reconstruction. At bone level, the thyroid initiates the bone to liberate the calcium in order to facilitate reconstruction activity.

The metabolic activity of the thyreotropic axis is strongly catabolic. It increases cell oxygen uptake, generating a catabolism of energetic substrates and an increase of metabolism. It also increases glycaemia by stimulating gluconeogenesis and glucogenesis, and increases lypolysis of adipic tissue and increases blood content of Free Fatty Acids, captured by muscles. Further, it balances protein anabolism and catabolism in an euthyroid state.

The physiological activity of the thyreotrope axis has an impact on the nervous system (supports neuronal development from second trimester of fetus life through early post-natal life, helps maintain normal oxidative status in the brain, preventing neurologic degenerative disorders). It also has an impact on growth and development (stimulates growth factors and increases number of glucose receptors during period of increased metabolic demand, increases angiogenesis). And it has an impact on the musculoskeletal system (increases osteoclasy for bone rebuilding, and muscle tone and development), and cardiac system (permissive effect on catecholamines for improving cardiac conduction and myocardial contractility).

More particularly, TRH alters rate and accuracy of DNA transcription, favors a pro-inflammatory state in a terrain with estrogen relaunching of thyroid axis and an hyper catabolic state, and stimulates endocrine pancreas for insulin release as well as through its stimulation of prolactin. And TSH increases insulin resistance, stimulates endocrine pancreas, increases cell turnover and membrane stability, increases rate of fibrosis.

D. The somatotrope axis is the constructor of the body. It has a strong dependence on the thyreotropic axis at every level (TRH, TSH and thyroid hormones) creating a fifth virtual "thyreo-somatotropic" axis. It serves at the end of the adaptation cycle for doing the reconstruction work to restore the initial state of the body.

The metabolic activity of the somatotrope axis is strongly anabolic, having a number of hormones involved in energy substrates. And in terms of acquisition and utilization, it ensures through growth and anti-growth factors the level of nutrient utilization and the cohesion of its integration.

More particularly, glucagon is stimulated by adrenaline and TRH, plays a role in short term energy management via glycogenolysis in the liver and long term glucose management via neoglucogenesis, and competes with insulin to control glycaemia. Insulin resistance is not an hormone, but a state that blocks insulin's metabolic activity to time nutrient entry to cell growth cycle, stimulated by low TSH, low prolactin and high GH and conversely inhibited by the reverse. Insulin supports production and storage of all energy elements (proteins by stimulating their synthesis, fats by inhibiting glycolysis and stimulating lipogenesis, glucose by inhibiting glycolysis and supporting neoglucogenesis). It can act as a growth factor if it follows GH (distribution of nutrients) or as an anti-growth factor, if it precedes GH (pathological situation).

The physiological activity of the somatotrope axis provides (via glucagon) and dispenses (via insulin) a brief and intense energy (glucose) to maintain the basal metabolic activity and ensure sufficient adaptation (glucose oxidation).

More particularly, GH is inhibited by somatostatin and accelerates the rate of protein synthesis for cell development and, upon initiation of the General Adaptation Syndrome and the thyreotropic axis, helps reconstruction to restore the initial state, once catabolism has been established (corticotropic and thyreotropic axis), and acts on gonadotropic axis to rebuild its reserves of raw materials. prolactin is intermediate between growth and anti-growth, reduces GH (but GH does not stimulate prolactin), is reduced by dopamine and estrogens, interrupts somatotropic cycle to relaunch ACTH and corticotropic axis, is stimulated directly by TRH which influences the passage from FSH to LH for androgen production, and can stimulate alpha sympathetic when in permanent increase. And Insulin distributes glucose to cells or sends it to liver for reserves, its synthesis is stimulated by hyperglycemia, is inhibited by somatostatin, Alpha sympathetic and a high TSH, and can block GH if hyperhemia.

Figure 8:
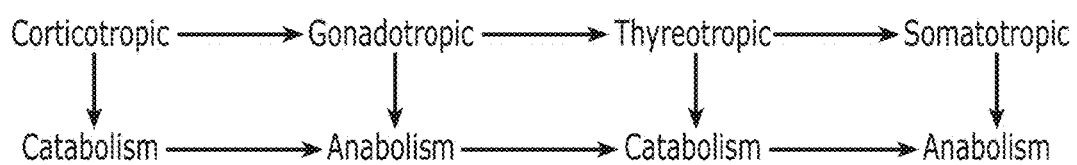
FIG. 8 is a graph providing a summary of the catabolic and anabolic activities of the axes of the endocrine system.

In summary and with reference to FIG. 8, the metabolism of the body is divided into two categories complementary and tightly interlinked:

a. catabolism: an activity of destruction, breaking down of substances and creation of energetic elements, and b. anabolic: an activity of reconstruction, building up of substances and utilization of energetic elements.

There cannot be any anabolism without a catabolism phase, and vice versa. The endocrine system follows that logic, and it is imperative to study closely the link between the axes to get a complete picture of the organism.

More information regarding application of the Biological Simulation Model according to the endocrine system according to example embodiments, see the attached Evaluation Guidelines.

4-4. THE ENDOBIOGENIC MEDICAL ASSISTANT (EMA™)

Figure 9:
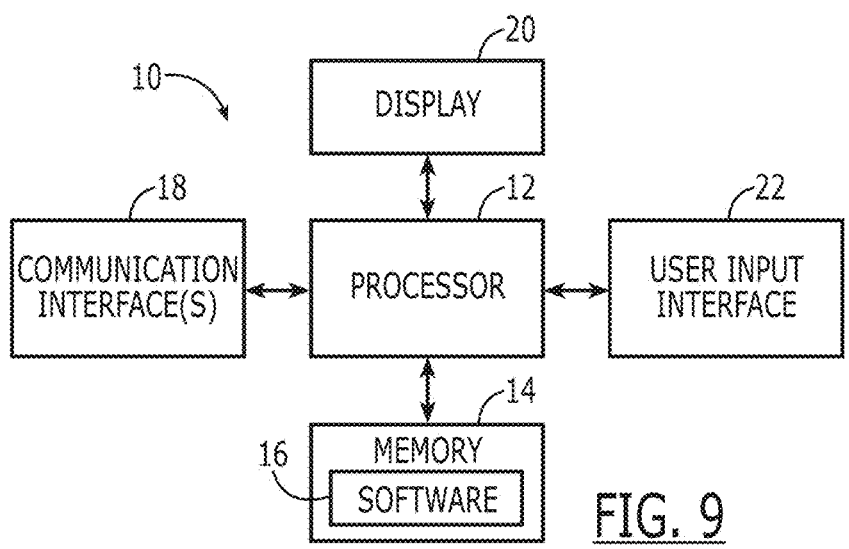
FIG. 9 is a schematic block diagram of an apparatus configured to operate in accordance with exemplary embodiments of the present invention.

Referring to FIG. 9, a block diagram of one type of apparatus configured according to exemplary embodiments of the present invention is provided, such as an apparatus configured to function as an EMA™. The apparatus includes various means for performing one or more functions in accordance with exemplary embodiments of the present invention, including those more particularly shown and described herein. It should be understood, however, that one or more of the entities may include alternative means for performing one or more like functions, without departing from the spirit and scope of the present invention.

Generally, the apparatus of exemplary embodiments of the present invention may comprise, include or be embodied in one or more fixed electronic devices, such as one or more of a laptop computer, desktop computer, workstation computer, server computer or the like. Additionally or alternatively, the apparatus may comprise, include or be embodied in one or more portable electronic devices, such as one or more of a mobile telephone, portable digital assistant (PDA), pager or the like.

As shown in FIG. 9, the apparatus 10 of one exemplary embodiment of the present invention may include a processor 12 connected to a memory 14. The memory can comprise volatile and/or non-volatile memory, and typically stores content, data or the like. In this regard, the memory may store content transmitted from, and/or received by, the apparatus. The memory may also store one or more software applications 16, instructions or the like for the processor to perform steps associated with operation of the apparatus in accordance with exemplary embodiments of the present invention (although any one or more of these steps may be implemented in hardware alone or in any combination with software and/or firmware).

In addition to the memory 14, the processor 12 may also be connected to at least one interface or other means for displaying, transmitting and/or receiving data, content or the like. In this regard, the interface(s) may include at least one communication interface 18 or other means for transmitting and/or receiving data, content or the like, such as to and/or from other device(s) and/or network(s) coupled to the apparatus. In addition to the communication interface(s), the interface(s) may also include at least one user interface that may include one or more wired and/or wireless (e.g., Bluetooth) earphones and/or speakers, a display 20, and/or a user input interface 22. The user input interface, in turn, may comprise any of a number of wired and/or wireless devices allowing the entity to receive data from a user, such as a keyboard or keypad, a joystick, or other input device.

The EMA™ according to one exemplary embodiment may be implemented as a web-accessible system in which the apparatus 10 may function as a web server receiving information from and providing information to users of similar apparatuses that may function as clients.

Figure 10:
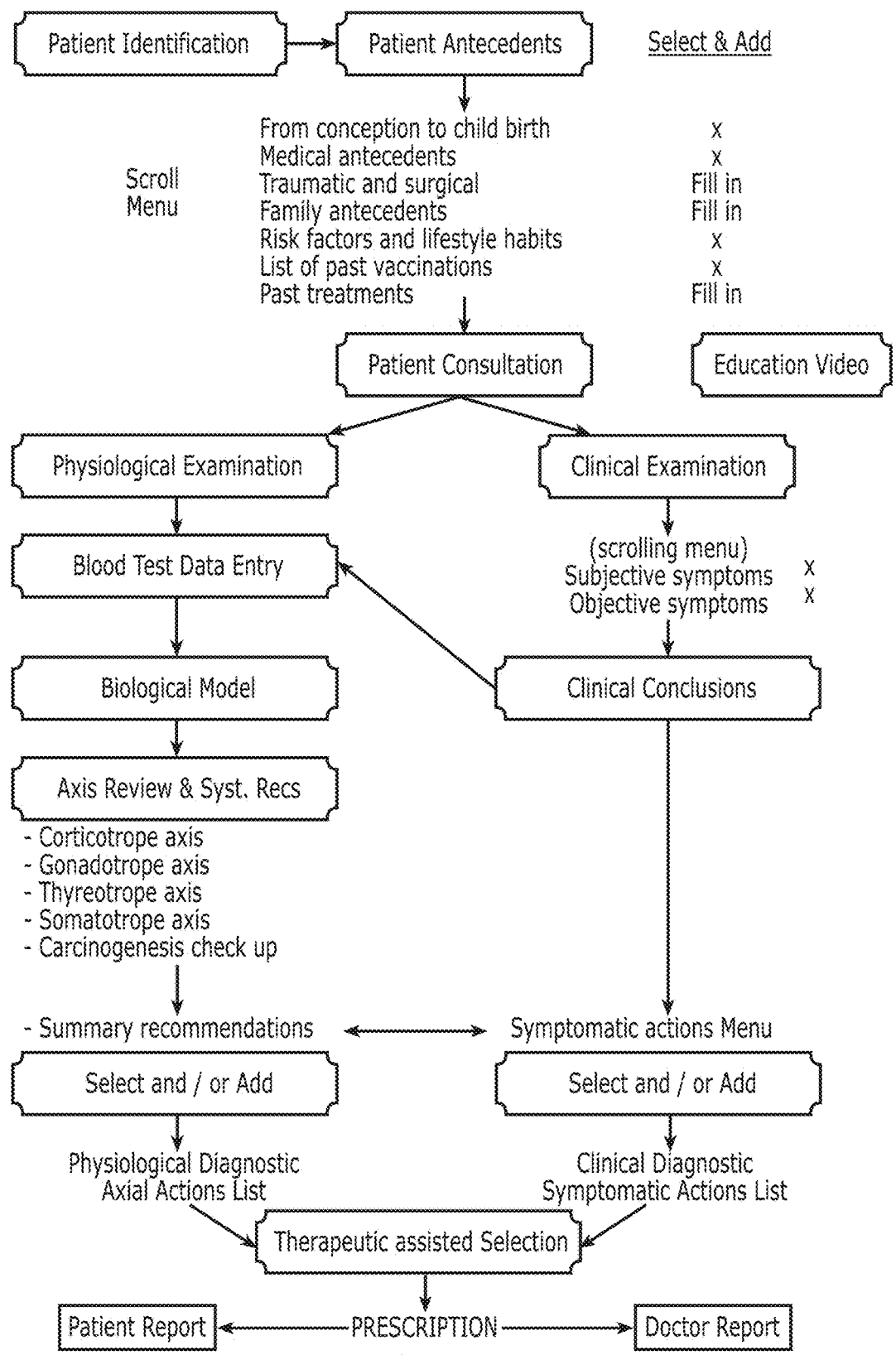
FIG. 10 is an overall system flow according to various exemplary embodiments of the present invention.

In accordance with exemplary embodiments, the EMA™ assists a practitioner across the whole patient process to get the best possible evaluation of the state of the patient and create the relevant prescription. FIG. 10 illustrates an overall system flow according to various exemplary embodiments. As shown, the system flow may be summarized through five phases:

1. patient antecedents (for new patient) followed by add-consultation (all patients);
2. clinical examination and conclusions on clinical diagnostic;
3. physiological examination and conclusions on physiological diagnostic;
4. selection of axial and symptomatic actions; and
5. selection of therapeutic items and creation of prescription.

The clinical examination phase may follow the classical approach with identification of subjective (patient based) signs and objective signs (result of clinical review). The diagnostic will lead to a set of symptomatic actions to select from a pre-defined list of 32 items or add, if required.

The physiological examination phase takes, as its source of data, the Biological Simulation Model defined from the blood test data, including a set of indexes to be analyzed by endocrine axis. The objective is to identify the list of endocrine dysfunctions underlying the state of the patient and requiring corrective actions. In total, there are 43 possible actions, of which many are mutually exclusive, for example, inhibit versus trigger a hormone or an organ. In practical terms an analysis of the endocrine system will generate between six and twelve corrective actions, depending on the severity of the dysfunctions. The system recommends a set of actions for the practitioner to select and/or add, if required.

In the therapeutic phase, EMA™ recommends a set of therapeutics for both the axial and the symptomatic actions for the practitioner to select and/or add and based on the user input, it produces a full prescription, including dosage.

Figure 12:
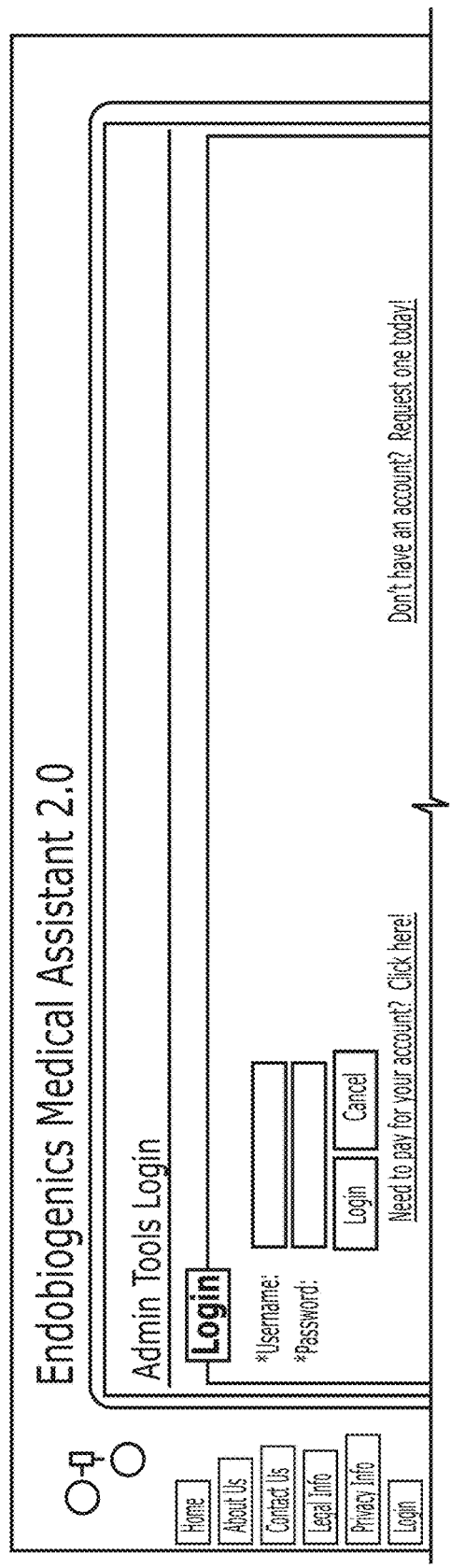
Figure 13:
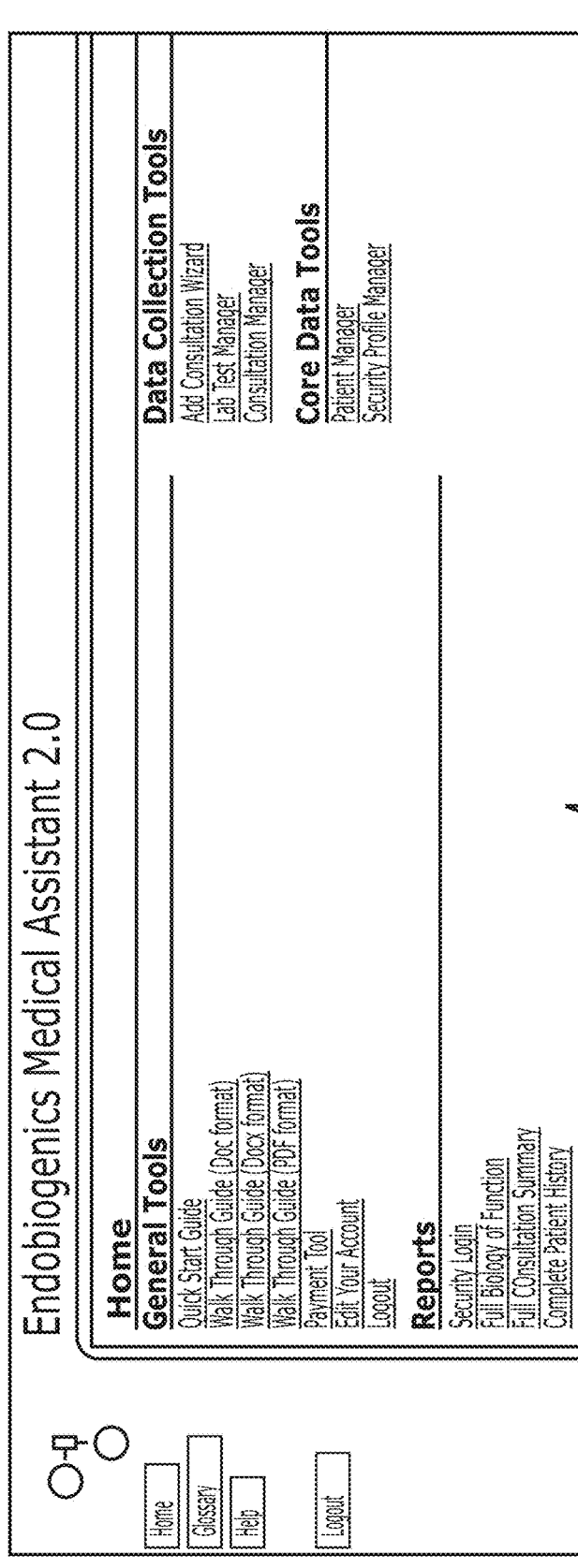
Figure 15:
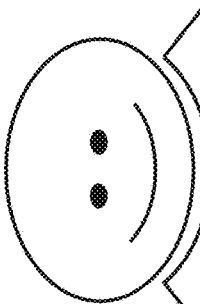

Reference is now made to FIGS. 11-36, which illustrate portions of various example displays that may be presented by EMA™ during operation. As shown in FIGS. 11 and 12, a user accessing EMA™ may be presented with a display including information regarding EMA™, and a display from which a user may authenticate or otherwise login to the system. After logging in to the system, the user may be presented with a home page such as that shown in FIG. 13. The home page includes a number of links for accessing features of the system, and for which the user may obtain information by selecting the "Quick Start Guide" link. As also shown in the home page, under "General Tools," the user may change information specific to their account (such as username and password). Under "Reports," the user may view security activity concerning their account and the full history of patient data. Under "Data Collection Tools," the user may manage Patient data, and under "Core Data Tools," the user may manage patient basic information and their own security profile.

Also under "Data Collection Tools," the home page includes an "Add Consultation Wizard" to access a wizard for guiding the user through entering patient data and creating a new consultation. In this regard, selecting the "Add Consultation Wizard" may direct the user to an add consultation screen such as that shown in FIG. 14. From the wizard screen, the user may select an existing patient, or if the desired patient does not exist within the system, add a new patient. In instances in which a new patient is being added, the user may select "add patient" to direct the system to present an add-patient display, such as that shown in FIG. 15, from which the user may enter patient administrative data into the system (including a patient picture if desired), and then return to the add consultation screen.

A user may select an existing or newly-added patient from the wizard screen by selecting the "Add New Consultation" beside the respective patient's name. The system may respond by presenting the first of a number of displays of the consultation wizard, namely the consultation information display, such as that shown in FIG. 16. From this display, the user may select the doctor, facility, date of treatment, whether the patient has cancer, and notes about the consultation.

From the consultation information display, the user may also access a patient review, such as that shown in FIG. 17, from which the user may edit patient basic information and patient history for an existing patient or enter patient history for a new patient. For example, as shown in FIG. 18, patient antecedents may be added or edited by selecting "Add New Patient Antecedent Items," and selecting the appropriate classification (four possibilities: From Conception to Childbirth, Medical Antecedents, Risk factors and Lifestyle habits, List of Vaccinations). Once the user has selected the classification, the user will be offered a two-level menu of possible antecedents to choose from:

Example: Medical Antecedents → Cancer type
Cardiovascular
...............

Neurological → Alzheimer
　　　　　　　　Amyotrophic Lateral Sclerosis
　　　　　　　　............
　　　　　　　　Depression ← Selected If a triangle is presented on the first menu, it indicates a sub-classification to address specific diseases, e.g., Diabetes within Endocrine, Hepatitis within Digestive, or a differentiation between Men and Women for Genital Diseases.

Figure 19:
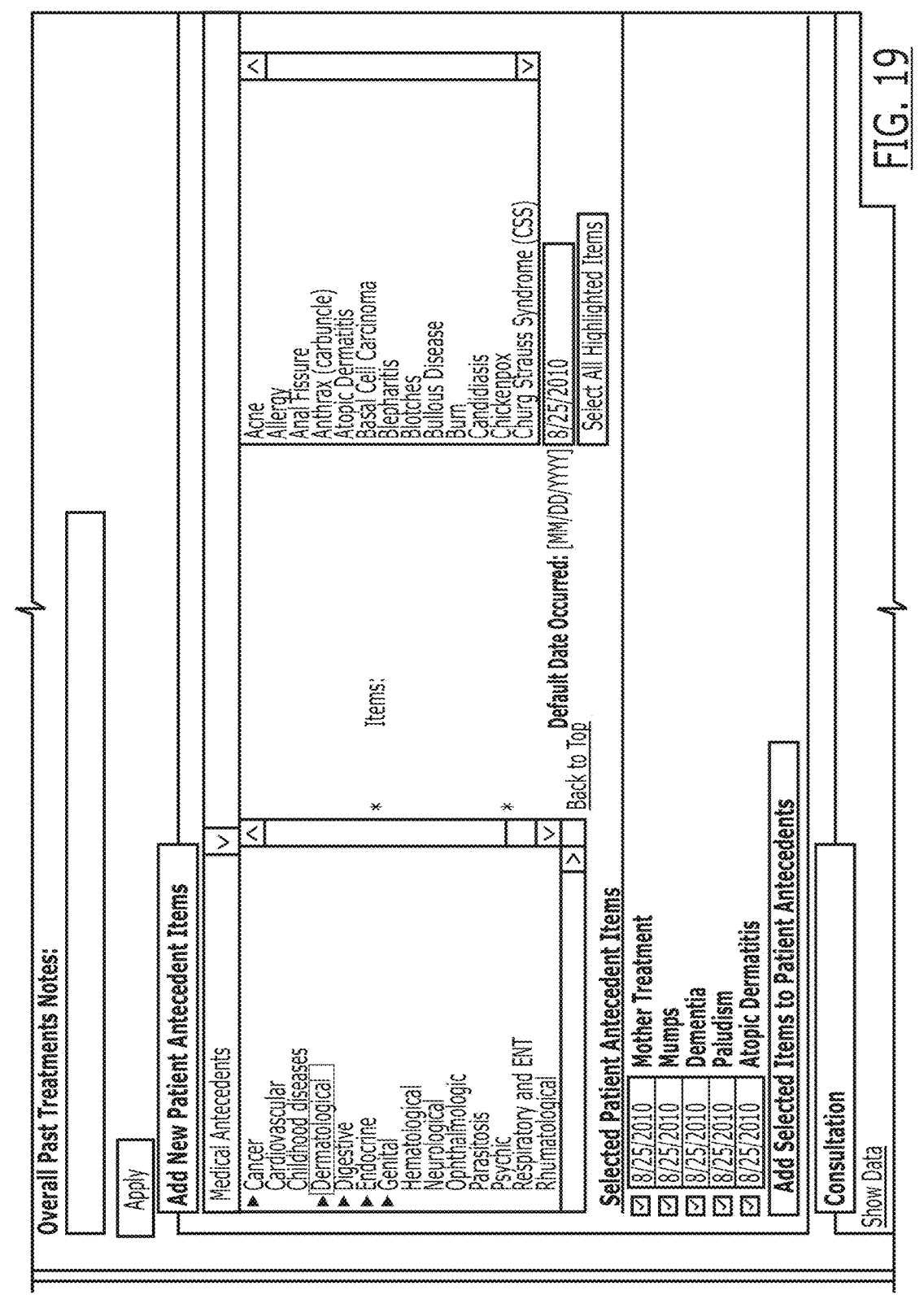

Once the user has selected all Antecedents, the user may enter a date for occurrence of each Antecedent and enter by selecting "Add Selected Items to Patient Antecedents," as shown in FIG. 19. The user may also add summary notes to different categories to be included in the patients file or add additional details to the antecedents you selected, as shown more particularly in FIG. 20.

After entering the patient antecedents, the EMA™ (the system) may present a patient examination display, an example of which is shown in FIG. 21. As shown in FIG. 21, the patient examination display may include (shown at the bottom of the display), a drop-down menu that enables the user to enter Subjective Signs, Measurements, Objective Signs and Newly Diagnosed Medical Antecedents. And as shown more particularly in FIG. 22, the display may also include a number of other sections including a Patient Examination Summary (notes from the user), Subjective Signs (as indicated by the Patient), an Objective Signs section for receiving information regarding the respective signs identified during the clinical examination, and a Newly Diagnosed Medical Antecedents section (notes only), the actual antecedents are selected in the lower section. The other sections may further include a Measurements section that may receive from the user, the basic measurements taken during the consultation, or taken by an assistant (blood pressure, height, weight, and pulse). In this regard, the patient's body-mass index (BMI) may be automatically computed.

Figure 23:
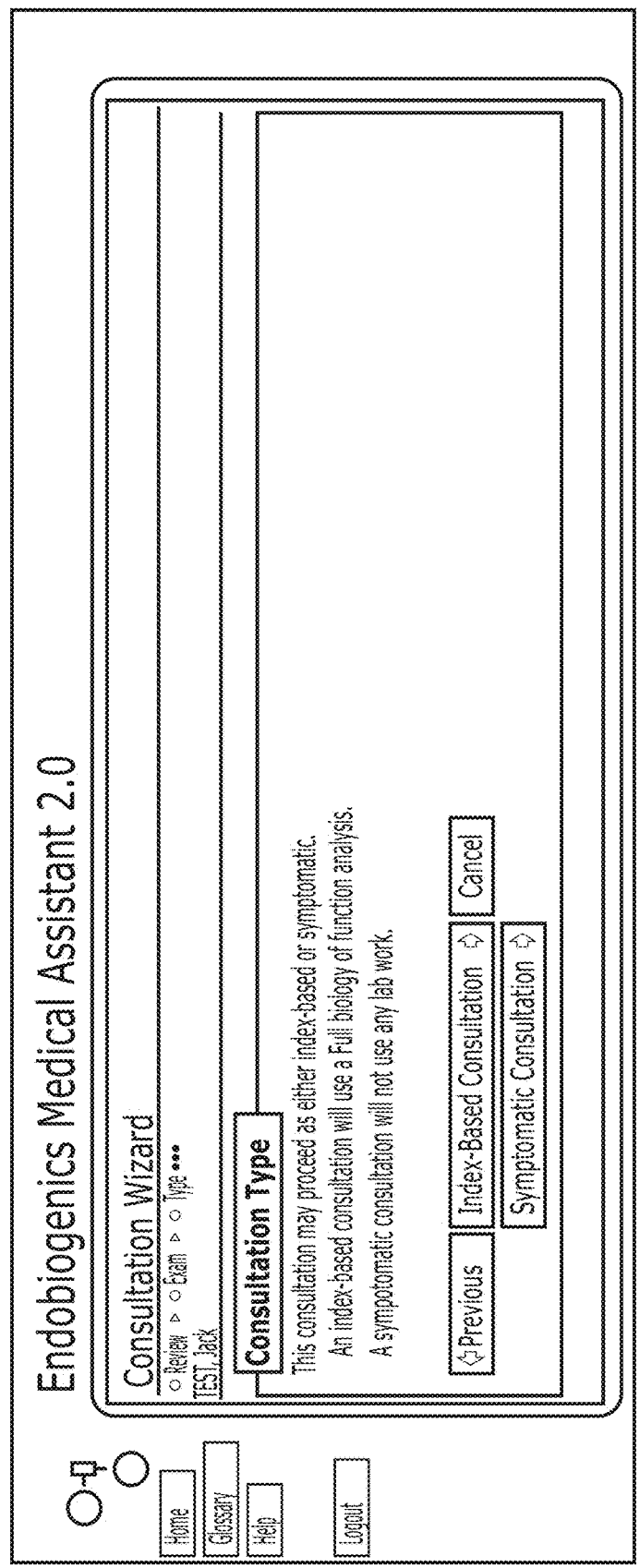
Figure 27:
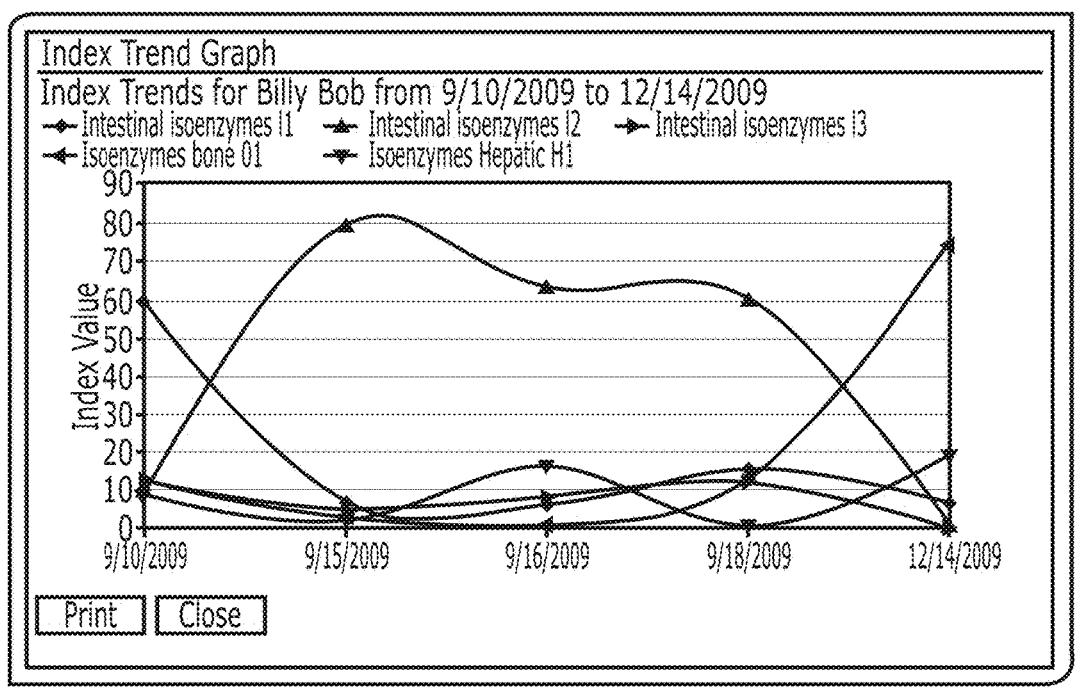
Figure 28:
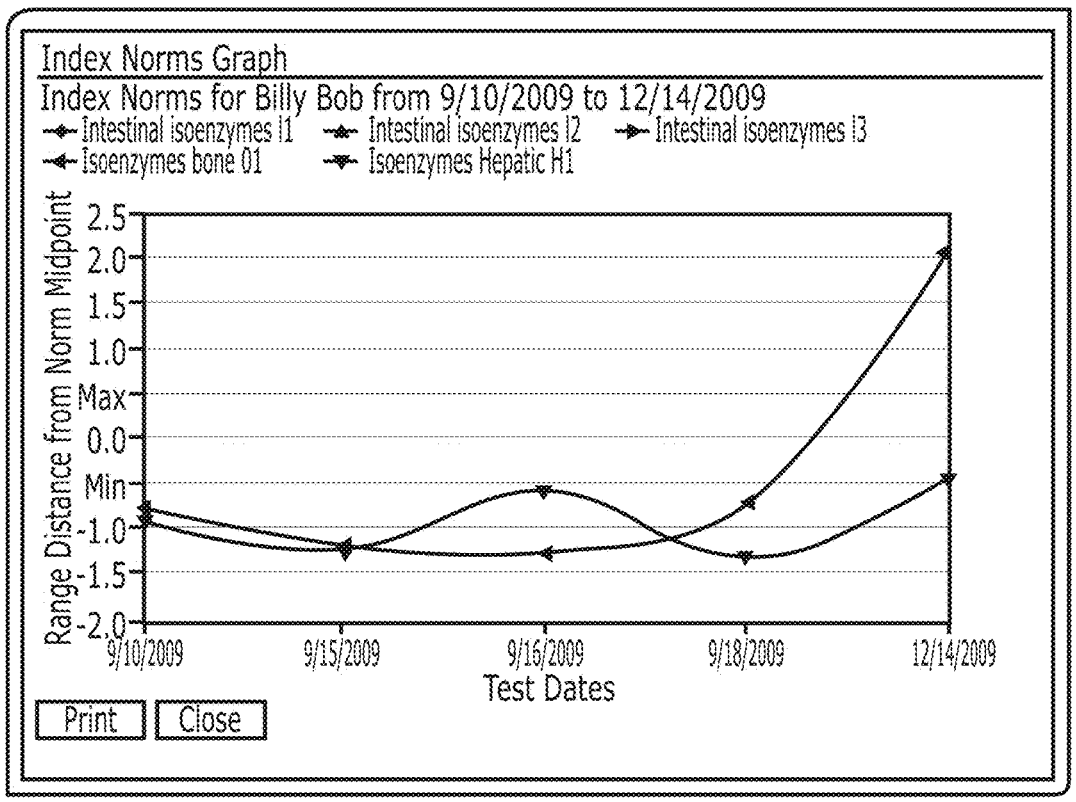

After completing the patient examination display, the user may proceed to the next display of the consultation wizard, namely the consultation-type display, an example of which is shown in FIG. 23. From this display, the user may decide how they wish to proceed in the wizard. As shown, the two principal options are an index-based consultation (leading to the biology of functions) with a consultation using generated indexes from lab work data, or a symptomatic consultation with a consultation based on the symptoms identified during the Clinical Examination, without lab work data. In an instance in which lab work is available and has been entered in a lab test manager, the user may select "Edit Recent Lab Work." In this regard, the lab test manager may be implemented in separate software that enables the user to enter lab test when received, independent of a consultation. The data may then be recalled at the time of a consultation. On the other hand, in an instance in which lab work has not yet been entered, the user may manually enter the lab work data by selecting "Manually Enter/Import Lab Work" and entered either manually or by uploading an Excel spreadsheet.

In an instance in which the user selects the symptomatic consultation option, the user may be directed to an action-summary selection display that in this instance, may present an entire menu of possible actions (axial or symptomatic) without recommendations. The user may then select from those actions based on their patient interview and clinical examination. An example of this display is shown in FIG. 32.

In an instance in which the user selects an "Index Based Consultation," the user may first enter the lab data into the system, such as by selecting "Manually Enter/Import Lab Work" to open an add-lab-test display such as that shown in FIG. 24. From this display, the user may enter information on: patient name, blood index category (male or female for adults or for children), and pregnancy or cancer state of the patient. The user may also enter information on the date of the lab test (anterior to the date of the consultation), which will sort out the sequencing of the biologies in a consolidated biology report. If the date is left blank, the system may default this date to the date of the consultation. Further, the user may enter the dates of last menstruation and chemotherapy, both factors that may distort some indexes or some data from the test (Leukocytes, e.g., for chemotherapy). The lab test date has to be set up prior to the chemotherapy date. And the user may enter the name of the testing lab, such as for further understanding of lab norms needed for four basic data (LDH, CPK, Osteocalcin and Alkaline phosphatases). The user may then select "Next" to manually enter the lab results, or select "Import Lab Results" to import the lab results (e.g., from the lab, or from a central facility within a hospital, clinic or research group).

In an instance in which the user chooses to manually enter the lab results, the add-lab-test display may further present a "Lab Test/Blood Work Index Results" section, as shown for example in FIG. 25. From this section, the user may start with the four lab norms (mini-maxi) for LDH, CPK, Osteocalcin and Alkaline phosphatases. In this regard, the sum of the leukocytes % distribution should add to 100%, as should the sum of the Isoenzymes % distribution. The system may be configured to accept any sum between 99 and 101% for these values, and may show a red flag if the sum is under/above this band. Also of note, the data needed for the Biological Simulation Model start with the red cells data and finish with the calcium data. Other data may be required and are optional, and the list may be extended to cover multiple uses.

After entering the lab results, the user may select "Next" to direct the system to present a biology-of-function report display, such as that shown in FIG. 26. This display includes indexes of the Biological Simulation Model regrouped along the four endocrine axes and along a special grouping related to carcinogenesis relevant indexes. This display may also repeat the lab results at the end of the biology. In an instance in which there has been a previous biology entered for the patient, the last one preceding the current biology will be shown automatically to highlight comparisons between the last two biologies. For the biologies, the report display may provide a color or other indication of whether an index is above, below or within norms. The report display may also provide an arrow or other indication of whether the current biology is up or down versus the last biology, and may further provide emphasis in instances in which the current biology is strongly up or down.

As also shown, each index has two numbers labeled "s" and "f." In this regard, "f" refers to function and provides a measure of the activity of a hormone or an organ in a given environment. And "s" refers to structure and provides a measure of the same activity, but excluding the impact of the adaptation. The structure and display values may be presented in a number of different manners. For example, the values may be stacked one below the other, or may be split in different columns. Many indexes have the same value for structure and function, which means that the adaptation impact is negligible for those particular indexes. Other indexes may have significantly different values for structure and function, e.g., a highly stressed person may have different values for cortisol, adrenal gland, metabolism rate, insulin or the like.

Various ones of the indexes may be visualized on a graph for trend and comparison purposes, and may be selected for visualization by a check-box or other means. The same facility may also exist on a full-biology-of-functions report display, which may permit the user to highlight on a graph the full history of an index.

Generally, the system provides two graphic options. In a first option, as shown for example in FIG. 27, a trend graph may be presented. The trend graph may be presented on a normal or logarithmic scale. In a second option, as shown for example in FIG. 28, a norms graph may be presented. This graph highlights the indexes selected in comparison with norms. The technique used is the variance to mid-point of the norms, to be able to put different norms on a same graph. Both graphs may cover the entire biologies entered in the system.

Returning to the biology-of-function report display, the user may continue by selecting "Next" to begin a biological analysis of the patient by axis: corticotrope, gonadotrope, thyreotrope and somatotrope. There are forty-two possible axial actions over the endocrine system, including two actions not covered by the system (stimulate or inhibit parasympathetic) that can only be identified from the clinical examination. The system will recommend actions by axis, but the user does not have to make a selection for each axis as all recommended actions are recapped at the end, in an action module of the wizard. Notably, the consistency and the repeatability of the Biological Simulation Model are ensured by the interlink between different indexes: 84% of the indexes are indirect, i.e., indexes of indexes, because this is the way the organism works. Accordingly, everything is interlinked, and the system takes this into account in the algorithm built to produce axial recommendations.

Figure 29:
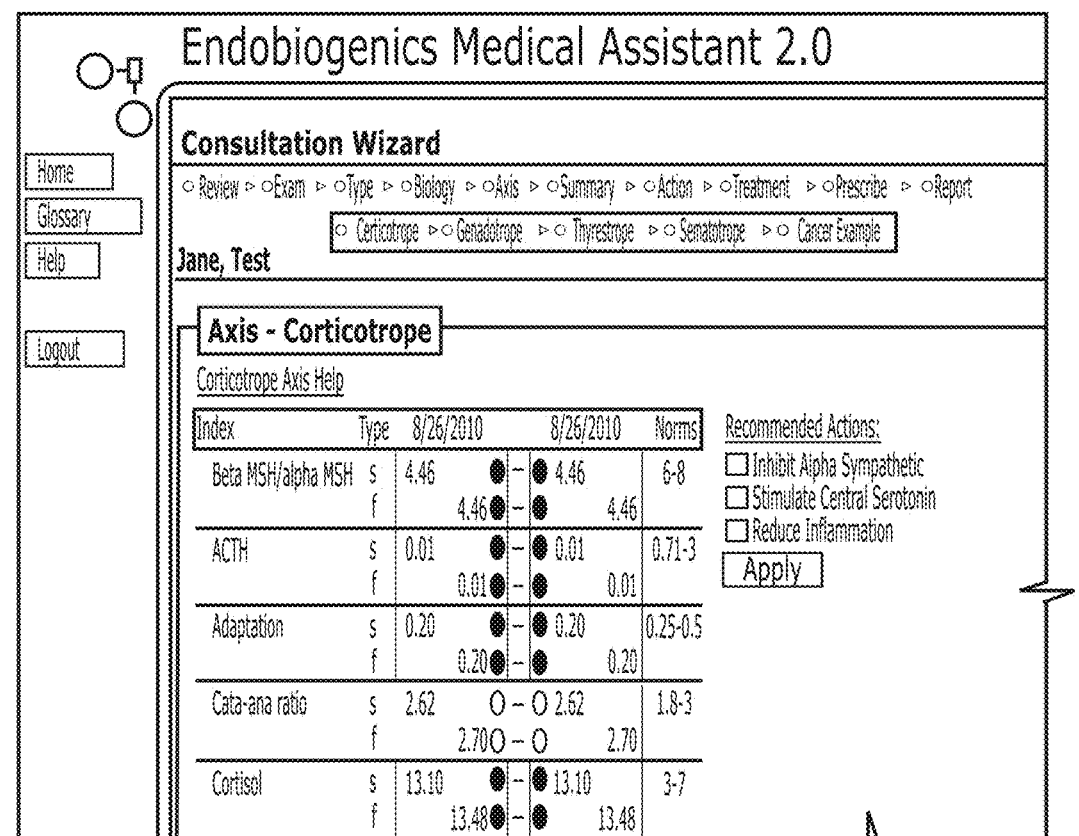
Figure 30:
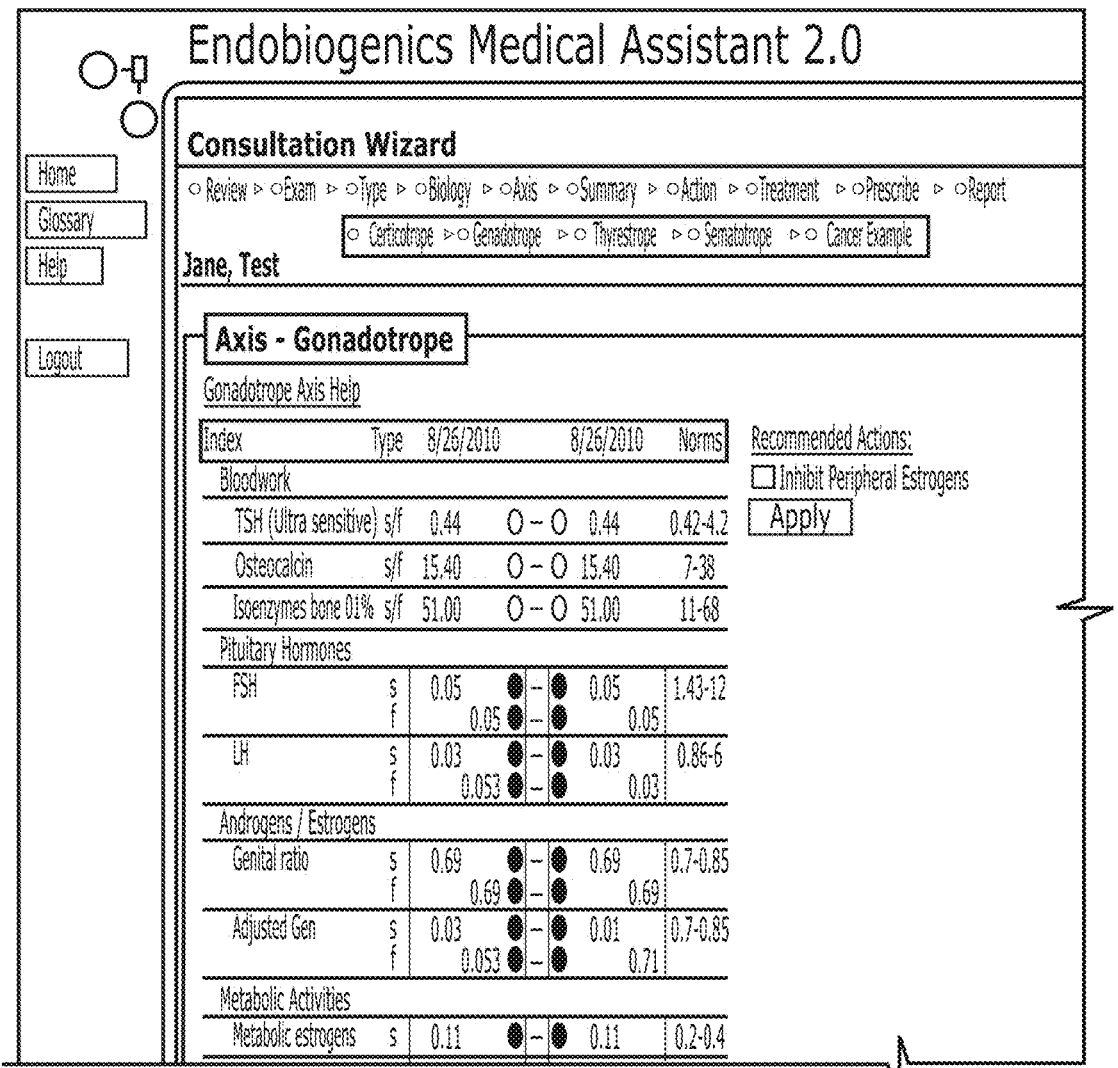

Examples of the biological analyses displays for the corticotrope and gonadotrope axes are shown in FIGS. 29 and 30, respectively. These displays may include a notes section intended to carry the user's personal observations as the user goes through each axis, which notes may then reappear in a biology summary display, where the user may wish to make their overall synthesis for the patient report. Also, as shown in FIG. 30, as the user moves their on-screen cursor over an index, the system may present a definition of the index.

In addition to the four axes, the biological analysis of the patient may also cover a fifth element, which is not an axis analysis. Instead, the fifth element shows indexes specially designed to track a degenerative process such as the cancer disease. Like any index, one generally cannot may any conclusions from a single index value, but instead from a series of indexes that can picture the overall parameters playing a role in the disease. If some indexes like DNA fracture, cell fracture, global expansiveness can give some indications, global factors such as the strength of activity of the immune system, the Growth Hormone, the estrogens, the anti-growth factors, the thyroid, the oxidoreduction, may play equally a major role in the evolution of the disease.

Figures 1, 31:
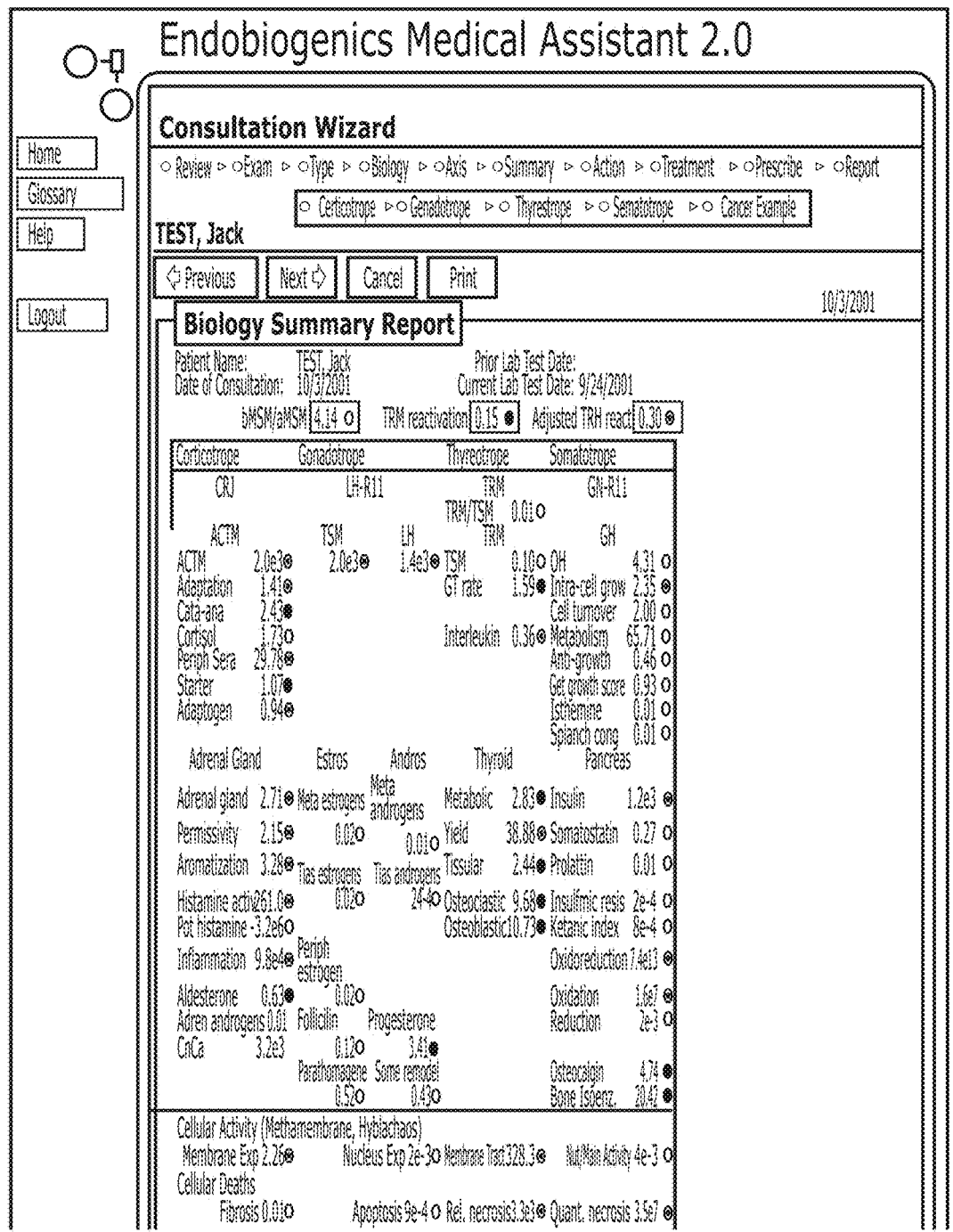

As shown in FIG. 31, for example, the system may display a biology summary report after the user navigates through the axes. It shows the key indexes for the current biology with the same code of evolution from the previous biology (circles for position versus norms, before and now, and an arrow indicating the trend). A space may be reserved for the personal conclusions of the user on the biology axial analysis.

FIG. 32 illustrates an example action summary selection display, which may be next presented in the process. This display includes three columns. In one column, the display includes a recap of the recommended axial actions. In another column, the display includes the set of other possible axial actions. And in the third column, the display includes the set of possible symptomatic actions.

From the action summary selection display, the user may select some or all of the recommended actions and/or select some of the complementary list of axial actions, as well as select some of the symptomatic actions, if needed, for complementary actions. In an instance in which the user does not have a biology for the patient, the user may select some of the symptomatic actions. The user may also select some of the axial actions if their clinical examination could identify some endocrine dysfunctions suggesting some specific axial actions, without system recommendations. Notably, the system may not trigger two axial actions (stimulate or inhibit para sympathetic) as they are expected to be selected upon the outcome of the clinical examination, if required.

Figures 1, 33:
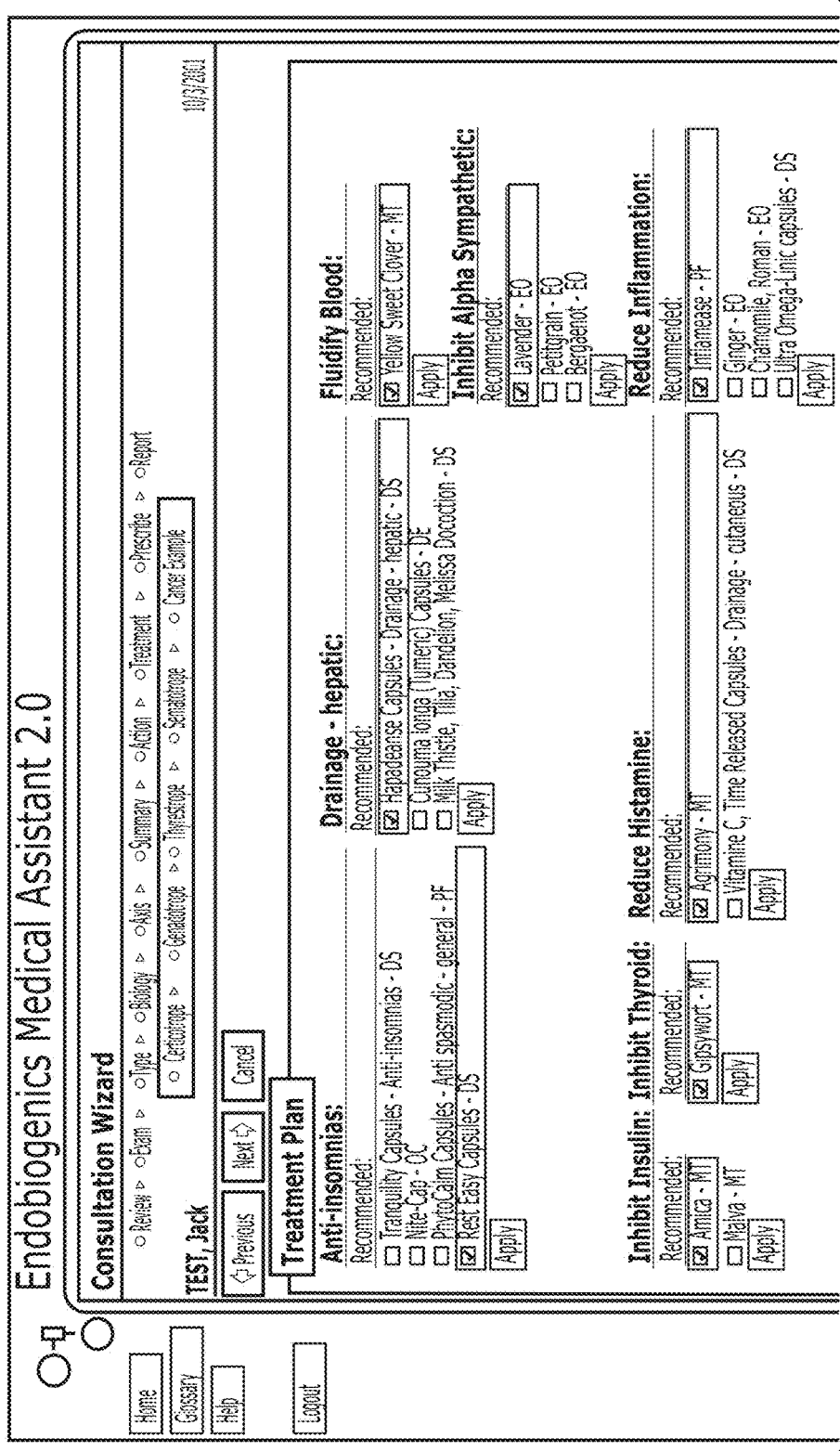
Figure 33:
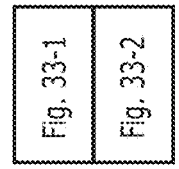

As another step in the process, the system may present a treatment plan display, such as that shown in FIG. 33. Here the user may select medications (selected items highlighted) to be included in a treatment plan, for both axial and symptomatic actions. Generally, a single choice is offered by action. A multiple choice may be offered to provide an alternative choice, in case of conflicting effects of product properties with the patient configuration.

Figure 34:
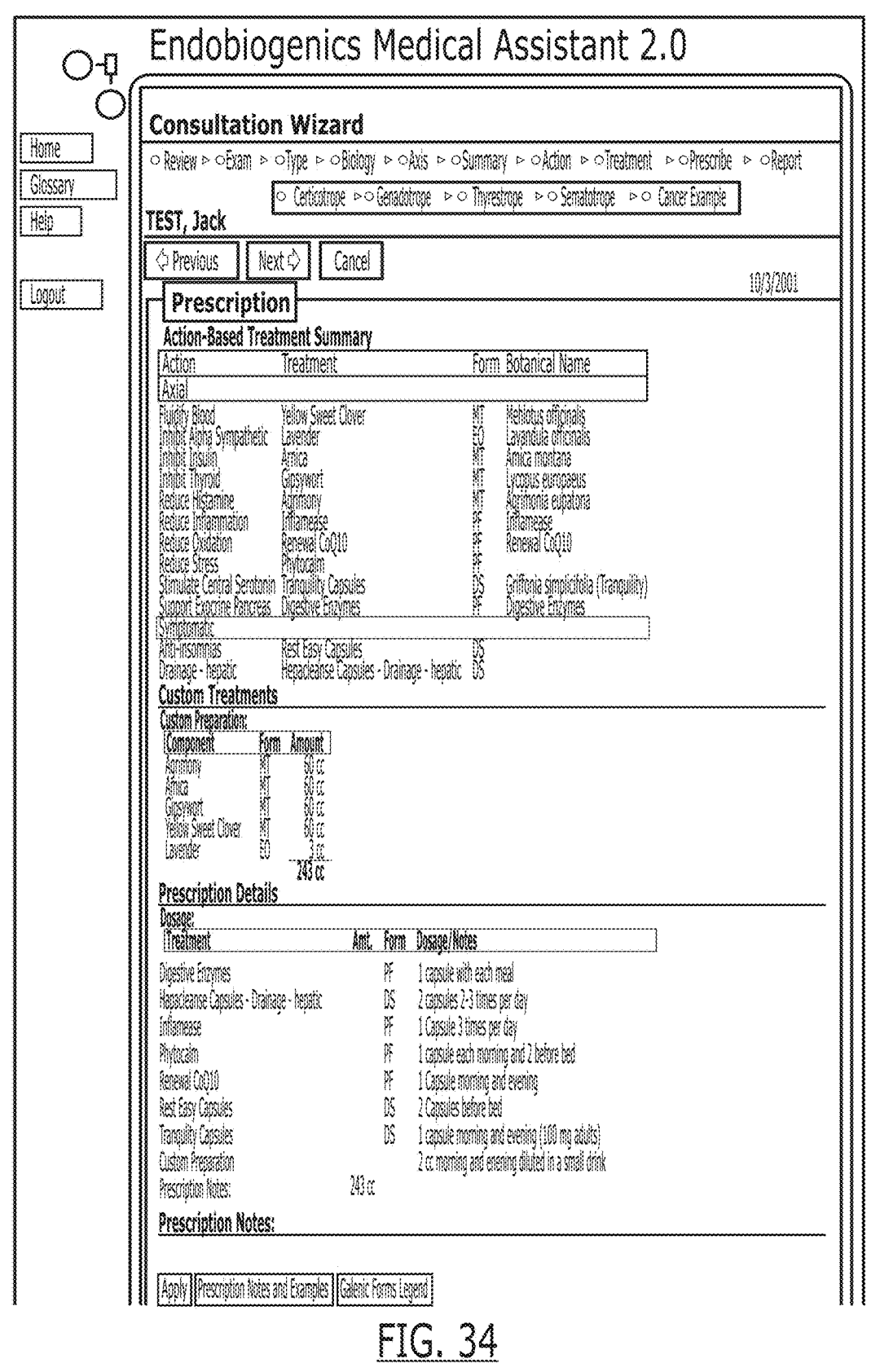

The system may also present a prescription display such as that shown in FIG. 34. This display may summarize the physiological actions selected and the associated medications automatically combined into custom preparations, where possible, with dosage. The system may also provide price quotes and prescription assistance, such as by the user selecting "Prescription assistance," and an order may be requested directly from a selected medication provider.

Figures 1, 35:
Figures 2, 35:
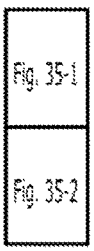

Finally, the system may present a doctor report display, such as that shown in FIG. 35. The report provided by this display may be reviewed by the user, and may be sent from the user to another user such as to a colleague practitioner. The system provides two variations of the report, namely a patient report and a prescription report.

According to one aspect of the present invention, all or a portion of the apparatus of exemplary embodiments of the present invention, generally operates under control of a computer program. The computer program for performing the methods of exemplary embodiments of the present invention may include one or more computer-readable program code portions, such as a series of computer instructions, embodied or otherwise stored in a computer-readable storage medium, such as the non-volatile storage medium.

It will be understood that each step of a method according to exemplary embodiments of the present invention, and combinations of steps in the method, may be implemented by computer program instructions. These computer program instructions may be loaded onto a computer or other programmable apparatus to produce a machine, such that the instructions which execute on the computer or other programmable apparatus create means for implementing the functions specified in the step(s) of the method. These computer program instructions may also be stored in a computer-readable memory that can direct a computer or other programmable apparatus to function in a particular manner, such that the instructions stored in the computer-readable memory produce an article of manufacture including instruction means which implement steps of the method. The computer program instructions may also be loaded onto a computer or other programmable apparatus to cause a series of operational steps to be performed on the computer or other programmable apparatus to produce a computer implemented process such that the instructions which execute on the computer or other programmable apparatus provide steps for implementing steps of the method.

Accordingly, exemplary embodiments of the present invention support combinations of means for performing the specified functions, combinations of steps for performing the specified functions and program instruction means for performing the specified functions. It will also be understood that each step or function, and combinations of steps or functions, can be implemented by special purpose hardware-based computer systems which perform the specified functions or steps, or combinations of special purpose hardware and computer instructions.

4-5. CONCLUSIONS

The methodology of example embodiments of the present invention is based on the current knowledge of the Physiological science: it provides an integrative new way of assessing the functioning of the organism, which positions the endocrine systems as the manager of the endocrino-metabolic and tissue equilibrium of the human body.

Using biological data obtained from a simple blood analysis, it permits, through a new approach on the linkage between the endocrine system elements (axis), to assess the functionality of these elements at cell, tissue, and global level.

The benefits of this approach are multiple:

1. assistance for a quantified evaluation of the functional biological state of a patient; identification of physiological dysfunctions linked with diseases; proposition of diagnostic conclusions;

2. assistance for selecting therapeutic treatment;

3. assistance for tracking efficiency of therapeutic treatments: modifications induced on the physiological state of the patient; early biological detection of drug side effects before clinical evidence;

4. assistance for prevention: early detection of pathology risks; and 5. assistance for research work: new links between physiological imbalances and specific diseases.

Many modifications and other embodiments of the invention will come to mind to one skilled in the art to which this invention pertains having the benefit of the teachings presented in the foregoing descriptions and the associated drawings. It should therefore be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

5. EVALUATION GUIDELINES – Corticotrope axis

Endocrine system

| *Peripheric alpha* ↓ | | | | |
|---|---|---|---|---|
| CRF ↓ | → | Gn-RH | TRH | GH-RH<br>GH-IH |
| ACTH | → | FSH / LH | TSH | GH |
| Adrenal gland<br><br>Cortisol<br>Aldosterone<br>Adrenal andros | | Ovaries<br>Testicles<br><br>Estros/ Proges<br>Genital andros | Thyroid<br>Parathyroïd<br><br>T4 / T3<br>PTH<br>Calcitonin | Pancreas<br>Liver<br><br>Insulin<br>Glucagon<br>Somatostatin |
| | C | E    L    L | S | |

The corticotrope axis is the key initiator of the General Adaptation Syndrome, which is the physiological response of the body to an aggression. It holds also a permissive role of secretion activation of other endocrine axis through the cortisol, which has a major metabolic role and generates multiple actions on the body's physiological systems

EVALUATION GUIDELINES – Corticotrope axis

SEARCH SEQUENCE

| Measurements | Assesment |
|---|---|
| Beta / Alpha MSH ↓ | → relative position beta vs alpha sympathetic<br>usually alpha dominant, i.e. index < norm (6-8)<br>if beta dominant (>8), watch impact on thyroid |
| Adaptation | → level of demand and overall body response |
| Cortisol | → level of cortisol response and associated peripheral factor (serotonin) |
| Starter | → level of 1st complementary adaptation response (glucagon route) |
| Adaptogen index ↓ | → level of 2$^{nd}$ complementary adaptation response (beta endorphins route) |

| | |
|---|---|
| Adrenal gland | |
| Adaptation-permissivity | →adaptation vs permissivity, index can be negative |
| Global activity | (adaptation purely permissive) |
| Permissivity | →adrenal gland global activity in its dual mission |
| Aromatization | (adaptative response vs permissivity /aromatization) |
| ↓ | |
| Histamine | |
| Histanine activity | →if adrenal gland activity low, histamine likely high |
| Potential histamine | →histamine receptors activity |
| Thrombogenic risk | →circulatory risk on lumenal structure |
| Thrombotic risk | (atheromas risk) and blood content (thrombotic risk) |
| ↓ | |
| Inflammation | |
| Inflammation | →level of inflammation and links with other indexes |
| Necrosis | |
| ↓ | |
| ACTH | →level of adrenal gland stimulation |
| Adrenal androgens | usually very low level = high demand = high cortisol |
| DHEA | →ACTH downwards stimulation over adrenal |
| Central aldosterone | androgens and central aldosterone |

| BACK-UP |
|---|

1 – BetaMSH / AlphaMSH:

** this index measures the relative activity of the beta sympathetic versus the alpha sympathetic
- bMSH and aMSH are two stimulating hormones of melanocytes which reactivate the adrenal gland through 2 complementary ways
….. the regular activation through the ACTH-cortisol route with beta sympathetic and adrenalin release
….. if needed an additional cortisol activation, through the alpha MSH, the so called short adaptation cycle
- if bMSH/aMSH > 8, beta sympathetic is predominant, with a stimulation impact over the thyroid
- if bMSH/aMSH <6, alpha sympathetic is predominant

** link with other indexes:
- thyroid metabolic index: the higher is the bMSH/aMSH, and the more active is the thyroid, bMSH/aMSH varies like the thyroid metabolic index
- adaptogen index (see definition below), which increases in the short adaptation cycle, hence bMSH/aMSH varies like the inverse of the adaptogen index

2 – Adaptation index:

| | | | |
|---|---|---|---|
| Eosinophils ↘ | | | |
| | Adaptation | → | Link ACTH – FSH |
| Monocytes ↗ | | | |

** this index evaluates both the adaptation demand and the adrenal gland answer. It also measures the relative adaptation activities of ACTH vs FSH → index low (<0.25):
- either a strong adaptation effort with low eosinophils, under stimulation of strong glucocorticoids (cortisol),
- or a situation of high chronic stress, with an increase of monocytes, under repeated stimulation of FSH by ACTH, with an inadequate estrogenic response.
- low index can also be the consequence of a high monocytosis, which can lead to mortality in cases such as an acute myocardial infarction, a bacterial sepsis or a cancer.

- low index can also reflect a state of imbalance of the immune system, that favors auto-immune and pro-inflammatory states inducing chronic morbidity such as Diabetes Mellitus, Hemodialysis, or Asthma → index high (>0.5):
- either the beginning of a response to an aggression, with an increase of eosinophils, under stimulation of ACTH,
- or a strong anabolic response to stress (lower monocytes) as one would expect during a response to an infection

3 – Adrenal response:

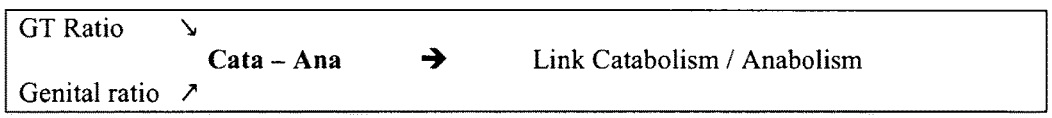

Cata-ana ratio**: it measures the relationship between catabolism and anabolism and it is an indication of the installation of the General Adaptation Syndrome (GAS) against the aggression
→ ratio low (<1.8): anabolism is dominant with a strong estrogeny ; It is a reconstruction phase, cortisol tends to weaken, except if the organism is in a situation of chronic stress (see above). Metabolic yield is usually high
→ ratio high (>3.0): catabolism is dominant, cortisol tends to increase to manage adaptation. Metabolic yield is usually low

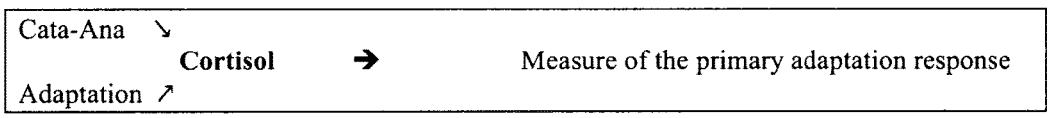

Cortisol**: it measures the activity of cortisol, which is the response of the adrenal gland to manage adaptation
→ index low (<3.0): either the adaption demand is low (hence the index is high), or the consumption of cortisol is high: situation of chronic stress with metabolic short cut, which reactivates cortisol and intra-cell activity with insulin increase,
→ index high (>7.0): it is a measure of the adaptative effort and of the seriousness of the aggression. This figure can reach several thousands in a situation of generalized cancer There are 2 other factors which participate in the adrenal response:

1 - peripheral serotonin: it measures the level of activity of peripheral serotonin. By extension it gives some indication of the activity level of central serotonin.
- there are 2 main factors influencing peripheral serotonin: <u>cortisol</u> (adaptative response) and /or <u>starter</u> (use of glucagon route, see below)

- more details on serotonin:
- serotonin interrelates between para and alpha sympathetic in order to extend the effects of para sympathetic at metabolic and functional level
- serotonin manages the intra-cell distribution of glucose through TRH and insulin, except in brain where the glucose distribution is under direct responsibility of serotonin
- peripheral serotonin receptors, located primarily in the bowel, are stimulated by adaptation to manage locally the glucose consumption
- an <u>excess of peripheral serotonin</u>, is usually associated with a <u>shortage of central serotonin,</u>

2 - peripheral aldosterone: it measures the peripheral impact of aldosterone during the General Adaptation Syndrome
- there are several factors impacting peripheral aldosterone, the major ones being:
- passive cell permeability induced by aldosterone
- and cortisol, reflecting the level of the adaptative response

- more details on aldosterone:
- it is part of the General Adaptation Syndrome
- it is under direct control of ACTH and it is increased by the glucocorticoids secretion
- it is followed afterwards by a stimulation of the resin angiotensin system (RAS), while will block the aldosterone in return Note: it may occur that the peripheral aldosterone is negative, induced by a negative passive cell permeability, consequence of a <u>negative adaptation / permissivity</u> index (see below) . The adaptation is then managed only through the <u>permissive channel</u> and the peripheral aldosterone is reduced to a stand-by role 4 – Alternative adaptation responses:

It may occur that the adrenal gland is not strong enough to manage the adaptation effort: it has two alternatives
- use the glucagon response through pancreas, to create a temporary hyperglycemia
- use the beta endorphins route, implicated with the immune function \*\* <u>Glucagon response:</u>

| | | |
|---|---|---|
| Mob. leucocytes ↘ | | |
| | I. starter → | relative level of glucagon (pancréas) |
| Mob. plaquettes ↗ | | vs adrenalin (adrenal medulla) |

\* Starter index: it measures the relative level of glucagon vs adrenalin in the initiation of the GA Syndrome
- The normal reaction to stress is a release of adrenalin, which blocks extra-cell energy except in sensitive areas, which need additional energy: it is the so-called immediate mobilization, to send energy where it is most needed
- if the aggression is due to last, or if it is chronical, the organism chooses the glucagon route: it is the deferred mobilization, with glucose distribution to cells, implying a metabolic overreaction
→ index low (<0,85): adrenalin dominates
→ index high (>1.15): glucagon dominates The starter index is the ratio of two indexes:
- leukocytes mobilization
- platelets mobilization

\* Leukocytes mobilization: it measures the mobilization of leukocytes out of the splanchnic area
→ index low (<0.85): immediate mobilization of Adaptation General Syndrome (AGS), i.e. beta sympathetic action and release of adrenalin. Alpha sympathetic is strong and prevents the evacuation of leukocytes
→ index high (>1.15): deferred mobilization of AGS, with stimulation CRF→TRH→Pancreas i.e. the glucagon route \* Platelets mobilization: it measures the mobilization of platelets out of the splanchnic area. Platelets sequestration depends on androgens production, while platelets desequestration depends on beta sympathetic.
→ index low (<0.85): sequestration dominates, hence androgens likely to be strong
→ index high (>1.15): desequestration dominates, hence beta sympathetic likely to be strong \*\* Endorphins response:

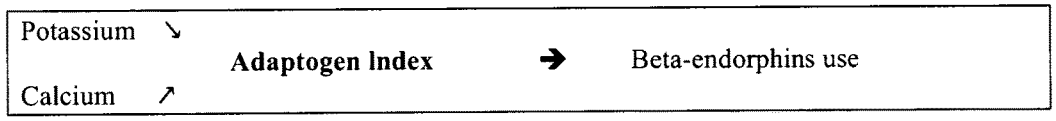

\* Adaptogen index: it measures the usage of beta endorphins in the management of adaptation. It is equal to the ratio K / Ca, and the norms are between 0.75 and 0.9
1 – in case of an <u>acute stress</u> using the AGS, circulating Calcium is slightly reduced, while circulating Potassium is stable, generating a slight reduction of the adaptogen index, which usually does not last
2 – in case of a <u>repetitive stress</u>, there is an increase of aldosterone which restores Calcemia, and reduce Potassium, generating a <u>decrease of the adaptogen index</u> through a decrease of Potassium
3 – when body uses the <u>short cut of beta endorphins</u>, it does not solicit aldosterone, hence no Potassium reduction, while Calcium is reduced through the release of adrenalin, which creates an hypocalcemia, As a consequence the <u>adaptogen index increases</u>

5 – Adrenal gland activity:

**\*\* adaptation-permissivity index:** it measures the difference between adaptation and permissivity
*Warning*: this is not a ratio, therefore it can turn to be negative, when permissivity is bigger than the adaptation response → this is an element to watch, because it indicates that the adaptation is purely permissive.
This situation can be found, when the adrenal gland is exceptionally strong
in comparison with cortisol and generating a very strong permissivity.

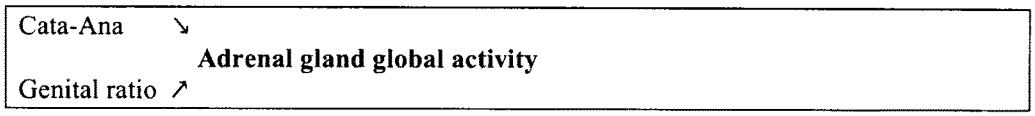

```
Cata-Ana     ↘
                 Adrenal gland global activity
Genital ratio ↗
```

**\*\* Adrenal gland global activity:** it measures the global activity of the adrenal gland, and it usually varies within a narrow range, between 2.7 and 3.3. As such it indicates whether the adrenal gland is weak or strong, but it does not indicate, whether it fulfills its dual role of adaptation and permissivity.
For this purpose, it is convenient to watch the ratio Cortisol/Adrenal gland, which should be around 3:
- ratio > 3: cortisol is over-stimulated by the ACTH, we have a strong adaptation demand and answer, and either an adrenal gland insufficient, or a cortisol essentially adaptative, with limited permissivity role
- ratio < 3: the adrenal gland response is adequate
- ratio < 1: this is an extreme situation, strong adrenal gland and weak cortisol, permissivity dominates, and adaptation becomes purely permissive (adaptation-permissivity <0)

Links with other indexes:
- adrenal gland global activity varies like the cata-ana index: the higher is the cata-ana, the higher is adrenal gland activity
- adrenal gland global activity varies like the inverse of the genital ratio (ratio androgens / estrogens): the higher is the genital ratio, the lower is the adrenal gland index → this explains why certain chemotherapies, using androgens anti-aromatase, when used for too long, can increase dramatically the genital ratio, and weaken considerably the adrenal gland.

**\*\* permissivity:** it measures the activity of the adrenal gland in the synthesis and the secretion activity of other hormones (permissivity)
This index permits to understand the weight of the adaptation effort on the adrenal gland activity:
- the less permissive is the adrenal gland, the more the endocrine system works in a stand-by mode, hence a reduction of the overall metabolism
- a reduction of permissivity, due to a strong stress-based cortisol, can however be a factor of thyroid reactivation to increase the catabolism and restore the overall metabolism Links with other indexes:
- permissivity varies like adaptation: the higher is the adaptation index, the lower is the cortisol response, and the higher is the permissivity

- permissivity varies like the inverse of the genital ratio: the higher is the genital ratio, the lower is the permissivity \*\* aromatisation: it measures the relative activity of aromatization of the adrenal gland compared to its other activities, and the norms vary between men (0.5 to 0.9) and women (0 .6 to 1.2)

Links with other indexes:
- aromatization varies like permissivity
- aromatization varies like the <u>inverse of the genital ratio</u>: the lower is the genital ratio, the higher are the estrogens, corresponding to a higher need for adrenal androgens aromatization.

6 – Histamine:

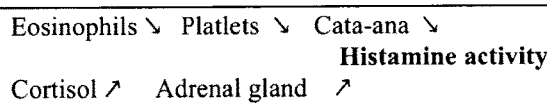

| Eosinophils ↘ Platlets ↘ Cata-ana ↘ |
| --- |
| Histamine activity |
| Cortisol ↗ Adrenal gland ↗ |

\*\* Histamine activity: it measures the activity of circulating histamine, and the norms vary between men (36 to 76) and women (20 to 60).

- usually a low histamine (<36 M or < 20 W) implies a strong adrenal gland, and the adaptation is well managed
- conversely, a high histamine (>76 M or >60 W) implies a weak adrenal gland
- however, it may happen that histamine is high, in spite of a normal adrenal gland: this may occur when the adaptation demand is weak (high adaptation index) or when the cortisol response is insufficient (high eosinophils)

Links with other indexes:
- histamine varies like the inverse of adrenal gland activity (see above)
- histamine activity varies like the inverse of cortisol activity: a strong cortisol response usually generates a low histamine

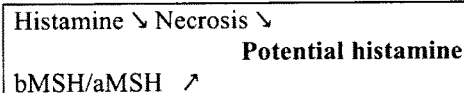

| Histamine ↘ Necrosis ↘ |
| --- |
| Potential histamine |
| bMSH/aMSH ↗ |

\*\* Potential histamine: it measures the amount of histamine receptors ready for use
*Warning*: this index can be negative, if the adaptation-permissivity index is negative, i.e. an adrenal gland index high relative to cortisol → it then indicates an excess of histamine receptors versus the needs of the body Roles of ACTH and of alpha sympathetic:
- ACTH increases the number of histamine receptors
- alpha sympathetic loads the histamine receptors,
hence, when histamine activity is high, it is usually the consequence of both a high ACTH and a strong alpha sympathetic Links with other indexes:
- potential histamine varies like histamine activity: self-explanatory
- potential histamine varies like the inverse of bMSH/aMSH: self-explanatory
- potential histamine varies indirectly like necrosis

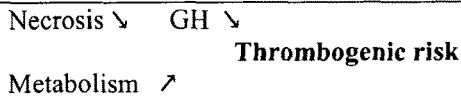
Necrosis ↘     GH ↘
                Thrombogenic risk
Metabolism ↗

Thrombogenic risk:** it measures the risk of degeneration of the inner walls of the arteries (atheroma)

Links with other indexes:
- thrombogenic risk varies like necrosis and the growth hormone
- thrombogenic index varies like the inverse of metabolism rate

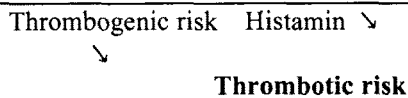
Thrombogenic risk    Histamin ↘
        ↘
        Thrombotic risk

Thrombotic risk:** it measures the risk of a blood clot production. By extension, it permit the level of blood coagulability.
Links with other indexes:
- thrombotic risk varies like thrombogenic risk
- thrombotic risk varies like the histamine activity

7 – Inflammation:

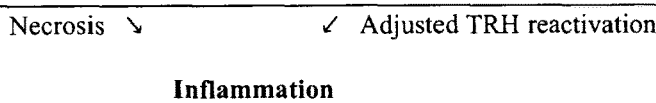
Necrosis  ↘          ↙ Adjusted TRH reactivation

Inflammation

Inflammation:** it measures the inflammation activity from internal source
- the main influencing factor is the level of necrosis.
- occasionally the adjusted TRH reactivation can increase the inflammation

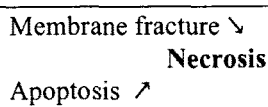
Membrane fracture ↘
        Necrosis
Apoptosis ↗

Necrosis:** it is a relative measurement of cellular death by necrosis versus cellular death by apoptosis

8 – ACTH and other related hormones

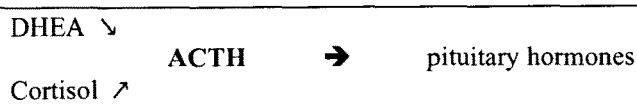
DHEA ↘
        ACTH   →    pituitary hormones
Cortisol ↗

ACTH:** it measures the activity of the ATCH pituitary hormone
-ACTH stimulates directly the cortisol and therefore the higher is the cortisol and the lower is ACTH, and conversely. ACTH activity varies like the inverse of cortisol activity
- ACTH stimulates also adrenal androgens (of which DHEA) but with a time delay: adrenal androgens can block the cortisol secretion without slowing down ACTH, which therefore varies like DHEA.

---

Seasonal changes:
- at beginning of Fall, hyper ACTH + hyper FSH, then peak of cortisol in october, which reactivates thyroid secretions. It is often a time of decompensation for degenerative diseases, like cancer, reactivated through hyperthyroidism. End of summer is also a time of increase of cardiovascular risks, after the excess of vitamin D, which generates an excess of calcium and calcareous deposits on arteries and coronaries
- at beginning of Spring, decrease of adrenal gland and thyroid activities, generating a temporary increase of ACTH and TSH to reset their reactivity levels. There will be no increase of alpha sympathetic, when ACTH reduces, because the level of reactivity has changed. This increases of ACTH can generate seasonal infections like cystitis or pyelonephritis, linked with too slow decrease of thyroid activity.

---

Adrenal androgens:** it measures the metabolic activity of adrenal androgens, which are stimulated by the ACTH

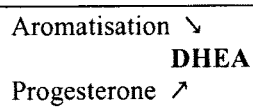

DHEA:** it measures the activity of DHEA, an adrenal androgen getting transformed through aromatization into testosterone and estrogens
- DHEA varies like aromatization, since it is the source of aromatization.
- Progesterone is a precursor of DHEA: when stress is very high, DHEA can be very low, because its consumption is high, generating an increase of Progesterone to refill the DHEA

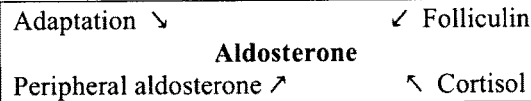

Aldosterone:** it measures the activity of the aldosterone, a key mineralocorticoid, which monitors the sodium to the detriment of potassium. The norms vary between Men (0,005 to 0,08) and Women (0,03 to 0,05)
- an excess of central aldosterone, which retains sodium and water, tends to increase the blood volume and the arterial pressure, reduce potassium (risk of cramps or cardiac rhythm troubles), and generate strong thirsts and polyuria
- a shortage of central aldosterone, which can be the consequence of an excess of activity in periphery (linked with the cortisol adaptative response), will generate a chronic dehydration and on a longer term a possible destruction of the adrenal gland
In practical terms:
1 – usually, the central aldosterone activity, is either normal or a little bit low, the consequence of an excessive activity in periphery to support the cortisol response to an aggression. Two options: treat it indirectly by acting on the cortisol and the adrenal gland, or treat it with a specific plant (« lespedezza capitata », see Therapeutics Guidelines), if the level of aldosterone activity is very low 2 – more rarely, the central aldosterone activity can be significantly ahead of the norm. It could be temporary and the consequence of diarrheas and other types of dehydration, but it could also be lasting resulting from a double stimulation upwards (ACTH/alpha) and downwards (Renin). It then needs to be treated with a specific plant (« crocus sativa », see Therapeutic Guidelines)

EVALUATION GUIDELINES 2 – Gonadotrope axis

Endocrine system

*Peripheric alpha* ↓

| CRF → | Gn-RH | TRH | GH-RH |
| | | | GH-IH |

↓

| ACTH → | FSH / LH | TSH | GH |

| Adrenal gland | Ovaries | Thyroid | Pancreas |
| Cortisol | Testicles | Parathyroïd | Liver |
| Aldosterone | Estros/ Proges | T4 / T3 | Insulin |
| Adrenal andros | Genital andros | PTH | Glucagon |
| | | Calcitonin | Somatostatin |

| C E L L S |

The gonadotrope axis manages the genital hormones, which play a key role on the protidic anabolism through their activity on the cell nucleus, and which contribute to growth, bones and muscles development. Three data play a key role in the evaluation of the activities of the gonadotrope axis:
- TSH, which plays the link between the anabolic estrogenic demand and the catabolic thyroid response
- Osteocalcin by its impact on bones activities and indirectly on estrogens activity
- and Alkaline phosphatases bones isoenzymes, an indicator of overall anabolic activity

EVALUATION GUIDELINES – Gonadotrope axis

SEARCH SEQUENCE

| Measurements | Assessment |
|---|---|
| FSH / LH | → vary like ACTH |
| | → adaptation reconstruction phase after the catabolic |

| | |
|---|---|
| ↓ | phase driven by the corticotrope axis<br>→ a high cortisol will induce indirectly a high estrogenic activity, with low upstream levels (ACTH and FSH/LH) |
| Androgens / Estrogens ratio<br><br>↓ | → relative strength of androgens and estrogens at pituitary level:<br>- either globally (genital ratio)<br>- or excl. the effect of adaptation (Adj. gen. ratio) |
| Metabolic activities<br><br>↓ | → metabolic activities of estrogens and androgens in total and across sourcing (adrenal and genital)<br>→ folliculin and progesterone activities |
| Tissue activities<br>↓ | → tissue activities in central (estrogens and androgens) and in periphery (estrogen receptors) |
| (Estrogens activities in a very low TSH environment < 0,5) | → different metabolic and tissue measurements |
| Bones and muscles activities | → Parathormone and link with T4 (agonist role)<br>→ Bone remodeling and link with GH<br>→ Muscle activity |

BACK-UP

1 – FSH – LH:

ACTH→FSH:** there is a link between the two pituitary hormones, which is the adaptation. The linkage goes one way from ACTH to FSH, without slow down feeed-back from FSH→ when a stress occurs, both ACTH and FSH increase together, whatever was the FSH level at that stage, and the higher is the stress, the lower is the adaptation index and the higher is the FSH increase.
As for any hormone, the threshold levels of response will vary according to needs, but in case of ACTH and FSH, their threshold levels will vary together.

LH:** varies with FSH and the ratio LH / FSH varies like the ratio of androgens over estrogens, excluding adaptation impact.

2 – Androgens / Estrogens ratio:

| |
|---|
| Red cells ↘<br>          Genital ratio<br>Leukocytes ↗ | genital ratio:** it measures the ratio of the global activity of androgens vs estrogens. The red cells synthesis is primarily caused by androgens, which are stimulated by the LH pituitary hormone, while the leukocytes are under the influence of estrogens, which are stimulated by the FSH pituitary hormone:
→ by extension the ratio red cells / leukocytes is called the genital ratio and varies like LH / FSH
- chemotherapies: a chemo treatment tends to destroy estrogenic receptors, which has as an immediate effect of reducing leukocytes, and consequently the genital ratio <u>increases</u>. The lack of estrogens will reduce in turn the amount of androgens and the genital ratio will <u>reduce</u> in a second phase. In a third phase, the estrogenic reactivation will increase leukocytes, then red cells by an increase of androgens, and the genital ratio will <u>increase</u> and return to a <u>normal level.</u>

| Adj. Red cells ↘ |
|---|
| Adj. Genital ratio |
| Adj. Leucocytes ↗ | adj. genital ratio**: it measures the ratio of the global activity of androgens vs estrogens, excluding the effect of adaptation.
In some infectious states, requiring acute adaptation effort, the adjusted genital ratio will be a better way to evaluate the structural balance between androgens and estrogens.

3 – Metabolic activities:

| TSH ↘ | aromatized estrogens |
|---|---|
| Estrogens metabolic activity → | |
| Osteocalcin ↗ | genital estrogens |

Total estrogens metabolic activity**: it is the sum of 2 components activities, aromatized estrogens (coming from transformation of adrenal androgens) and genital estrogens:
- the estrogens metabolic activity is anabolic and varies like TSH: if anabolic activity prevails over catabolism, the thyroid is low and the TSH is high
- the estrogens metabolic activity which covers essentially bone metabolic activity will vary like the reverse of osteocalcin blood content: if the latter is high, osteocalcin is not used in the bones and the estrogens metabolic activity will be low and vice versa

| Estrogens metabolic activity ↘ | adrenal androgens |
|---|---|
| Androgens metabolic activity → | |
| Adjusted Genital ratio ↗ | genital androgens |

Total androgens metabolic activity**: self-explanatory definition, and it is the sum of 2 components activities, adrenal androgens and genital androgens
- androgens metabolic activity is oriented primarily towards muscles (80%) and secondarily towards bones (20%), while estrogens metabolic activity is oriented primarily towards bones.

| Estrogens metabolic activity ↘ |
|---|
| Folliculin activity |
| Progesterone ↗ |

Folliculin**: it measures the estrogenic activity in its folliculin sourcing, i.e. estrogens produced by ovaries and, in small quantity, by testicles
- the state of <u>hyperfolliculiny</u> is characterized by an increase of estrogens and FSH, with an unbalance between estrogens and progesterone. The potential dysfunctions are: short menstrual cycles (70% of cases), increased sexual desire
among women, mammary dystrophy (coming from an imbalance between estrogens and progesterone), uterine fibroma (when hyper FSH and increase in estrogens receptors), melanoma (participation of thyroid and hyper MSH), sweats (with a strong para sympathetic, a strong alpha sympathetic reactional, and a beta sympathetic asynchronized)

| Estrogens metabolic activity ↘ | |
|---|---|
| Progesterone activity | |
| Adrenal androgens ↗ | ↘ Genital ratio |

Progesterone**: it is a precursor of DHEA to be transformed into testosterone and estrogens, through the aromatization scheme:
- the higher is the estrogenic metabolic activity, the higher is the demand for aromatization, and the higher is the progesterone
- the lower is the adrenal androgens, as a consequence of aromatization, and the higher is the progesterone to refill the DHEA.
- an insufficient progesterone triggers an increase of LH and hence an increase of the genital ratio 4 – Tissueactivities: 3 types of measurements in central and in periphery:
- central estrogens tissue activities
- central androgens tissue activities
- peripheral estrogens tissue activities 5 – Very low TSH environment (TSH < 0,5):
When TSH is very low, it tends to distort the formulas and suggest measurements which are understated. A set of specific low TSH measurements has been designed to cover:
- the metabolic estrogens activity
- and the tissue estrogens activity in central 6 – Bones and muscles activities:

| Calcium ↘ | Osteocalcin ↘ |
|---|---|
| Parathormone | |
| Thyroid yield ↗ | |

Parathormone**: it measures the activity of the parathormone, an hormone, synthetized and released by the parathyroid glands, that controls the distribution of calcium and phosphates in the body.

<u>Parathormone action</u> concerns essentially <u>bones</u> and <u>kidneys</u>:
- at bones level, it favors osteolysis, which triggers transfer of calcium (as well as osteocalcin) and phosphates from bones to blood → it varies like calcium and osteocalcin blood levels
- at kidneys level, it favors phosphates elimination through kidneys Parathormone plays a similar osteolytic role than thyroid, hence if T4 is high, parathormone activity is slow and conversely → it varies like the reverse of T

| TSH ↘    GH activity ↘ |
|---|
| Bone remodeling |

\*\* Bone remodeling: it measures the bone remodeling activity. Bone is a dynamic tissue which goes constantly through remodeling, even after growth and modeling of the the skeleton have been completed.
There are <u>two essential factors</u> which play a role in the bone remodeling:
- <u>GH activity</u>, which measures the metabolic activity of the Growth hormone
- <u>TSH</u>, which reactivates estrogens in their contribution to growth, mainly focused on bones This index helps to study the bone metabolism:
- if low ( <2), there is a risk of osteoporosis
- if very high (20 and above), likelihood of arthrosis or arteriosclerosis
- beyond 80, it could be a situation of a broad resorption of the bone tissue or the beginning of bone metastasis. These risks, which could indicate a Piaget disease, become likely beyond 200.

| Structural Androgens ↘    CPK ↘ |
|---|
| Muscles metabolism |
| Structural Estrogens ↗  Bones isoenzymes ↗ |

\*\* Muscles metabolism: it measures the ratio of muscles metabolic activity versus bones metabolic activity
- on one side, the structural androgens (i.e. excluding the effect of adaptation) and the CPK to qualify the muscles metabolic activity
- on the other side, the structural estrogens (i.e. excluding the effect of adaptation) and the Bone isoenzymes of Alkaline Phosphatases, to qualify the bones metabolic activity

EVALUATION GUIDELINES 3 – Thyreotrope axis

Endocrine system

*Peripheric alpha*
↓

| CRF | → | Gn-RH | TRH | GH-RH |
|---|---|---|---|---|
|  |  |  |  | GH-IH |

↓

| ACTH | → | FSH / LH | TSH | GH |
|---|---|---|---|---|

| Adrenal gland | Ovaries Testicles | Thyroid Parathyroïd | Pancreas Liver |
|---|---|---|---|

| Cortisol | Estros/ Proges | T4 / T3 | Insulin |
| Aldosterone | Genital andros | PTH | Glucagon |
| Adrenal andros | | Calcitonin | Somatostatin |

| C E L L S |
|---|

The thyreotrope axis mobilizes energy reserves by increasing basic metabolism and it has a number of interactions with the somatotrope axis to initiate the reconstruction efforts. The role of the thyroid is to support catabolism in order to bring to all body levels the material it needs for the anabolic reconstruction.
At the bone level, the thyroid dismantles the structure of the bone in order to release calcium, which will participate in the osteoblastic reconstruction.
TSH is an essential factor, which represents both the estrogenic demand and indirectly the thyroid response, with all the implications
on the somatotrope axis.

EVALUATION GUIDELINES – Thyreotrope axis

SEARCH SEQUENCE

| Measurements | Assessment |
|---|---|
| TSH | → Standard range (0.7 to 4.7): tends to be too wide  More practical range: 1.5 to 2.5 |
| Gonado / thyreotrope cross activities  ↓ | → Genito-thyroid ratio: indications on the Relationship between TSH and thyroid, and on the thyroid response to the estrogenic demand  → Gonado-thyreotrope index: relative strength of the estrogenic demand |
| Thyroid activities  ↓ | → Metabolic activity: if high, watch beta sympathetic  Thyroid yield: if high, TSH low and vice versa  Tissue activity  Bone support activity (osteoclasic and osteoblastic) |
| Thyroid lateral adaptation reset  ↓ | → level of permanent reactivation of the thyroid for adaptation purpose, independently of the General Adaptation Syndrome |
| TRH activities  ↓ | → TRH endocrine activity  TRH intra-thyroid (T3 vs T4)  TRH vs TSH tissue activity  TRH direct action over pancreas  TRH reactivation by locus coeruleus |
| Amylosis activiy | |

| BACK-UP |
|---|

1 - Gonado / thyreotrope cross activities

| Neutrophils ↘ | | |
|---|---|---|
| | Genito-thyroid (GT) ratio → | gonado-thyreotrope link |
| Lymphocytes ↗ | | |

**\*\* Genito-thyroid ratio:**
The secretion of granulocytes (of which neutrophils represent 90% of total) is dependent on estrogens, while the secretion of lymphocytes is dependent on TSH. By extension the ratio Neutrophils / Lymphocytes represents the thyroid response to the estrogenic demand, since TSH varies like the inverse of thyroid: the higher is the ratio, the lower are the lymphocytes and consequently TSH, hence the higher is the thyroid.

This index has 2 meanings: it measures the thyroid response to both the TSH stimulation and the estrogenic demand
1 – thyroid response to TSH stimulation:
- if ratio < 1.5: TSH predominant
- if ratio > 2.5: thyroid predominant
2 – thyroid response to estrogenic demand:
- if ratio <1.5: thyroid response is insufficient to cover estrogenic demand, in spite of a strong TSH stimulation, without prejudging on their absolute levels
- if ratio > 2.5: thyroid response is satisfactory compared to the estrogenic demand, and high relative to TSH stimulation. By extension the estrogenic demand is equally high.

| TSH ↘ | | |
|---|---|---|
| | Gonado-thyreotrope index → | gonado-thyreotrope link |
| GT ratio ↗ | | |

**\*\* Gonado-thyreotrope index:** it measures the relative level of the estrogenic demand compared to the thyroid response. It is another way to measure the strength of the estrogenic demand.

2 – Thyroid activities:

| LDH ↘ | |
|---|---|
| | Thyroid metabolic activity |
| CPK ↗ | |

**\*\* Thyroid metabolic activity:** . The 2 components LDH and CPK are enzymes, which are sensitive to thyroid activity, but in a different manner:
1 – CPK are activated much faster than LDH, and therefore their blood rate tends to decrease faster. An increase of the overall metabolism tends to favor first the muscular activity, hence a higher use of CPK and a subsequent decline of their blood rate.
2 – LDH are slower to get into action, and they tend to increase each time the TSH relative activity is increased.

The ratio LDH / CPK gives an appreciation of the metabolic activity of the thyroid in its capacity of providing the organism with its energy needs. It differs from the state of the thyroid (hypo or hyper), because it depends on the needs of the body. This index can be relatively low, with an hyperthyroidism, if this hyperthyroidism is insufficient to respond to functional needs.

- if index is high ( > 5.5), it suggests that cells are being over-stimulated by thyroid hormone, even if blood levels of thyroid hormone are in the normal range (cells might just be more sensitive to the thyroid hormone that is presented to them). Thus, there will be an increase in the catabolism in cells. Increased catabolism often results in excess of free radicals which can be damaging to healthy tissue. It can also result in a loss of bone density leading to osteoporosis. In addition, increased thyroid activity stimulates the beta sympathetic nervous system and this can result in hyperactivity, nervousness, high blood pressure, and irritability. Increased sympathetic nervous activity will then increase the demand on adrenal gland, contributing to adrenal exhaustion.

- if index is low (<3,5), it suggests that thyroid gland is not making enough thyroid hormone or that peripheral tissues are not converting T4 to T3, or that cells are not adequately receptive to the effects of thyroid hormone. As a result, the body is not able to catabolize adequately, and thus it essentially operates as if it is starving for energy. Fatigue and poor tissue structure result from this situation (brittle nails, brittle dry hair, dry fragile skin).

| Thyroid metabolic activity ↘ |
|---|
| Thyroid yield |
| TSH ↗ |

Thyroid yield**: it measures the metabolic activity relative to the level of pituitary stimulation (TSH). By extension, it measures the threshold of thyroid response to TSH stimulation
- Triodothyronine (T3) and L-thyroxine (T4) are the 2 elements of the thyroid hormone, at central level (T3) or at peripheral level (T4). The transformation T4→T3 is done under TRH stimulation
- T4 liberates calcium from bones (osteoclasic activity): it is directly stimulated by estrogens
- the transformation T4→T3 creates a decrease of T3 and hence a reactivation of TSH
- iodine brings the material to synthetize T4, but it has no effect on TRH
- thyroglobulin is a precursor of T4, stocked in thyroïd: it increases when thyroid cannot satisfy demand of T4

- TSH and thyroid: TSH at blood level measures the level of solicitation of the thyroid and its capacity to respond to the global needs of the the body. It indicates in particular the level of catabolism required by the functional level of anabolism. At bones level, TSH manages directly the number of osteoblasts required to produce osteocalcin.

- Beta sympathetic and thyroid: the beta sympathetic has a direct stimulation over the thyroid, by facilitating the transformationT4→T3: it liberates some reserve hormones between T4 and T3, which reactivates the whole TRH loop.

| |
|---|
| Thyroid metabolic activity ↘ |
|                      Thyroid tissue activity |
| GT ratio ↗ |

\*\* Thyroid tissue activity: it measures the metabolic activity relative to the thyroid response to the TSH stimulation → the higher is the response, the lower is the index, and vice versa. By extension, it measures the tissue activity of the thyroid.

\*\* Bone support activity: 2 types a – osteoclasic activity: it measures the catabolic activity of the thyroid over the bones (osteolysis). It varies like the LDH, with catabolic action, and like the inverse of Bone isoenzymes of alkaline phosphatases, which measures the overall bone anabolic activity.

b – osteoblastic activity: it measures the anabolic activity of the thyroid over the bones (reconstruction phase). It varies like the CPK, with anabolic action (favors synthesis of Adenosine triphosphate during muscular effort) and like the inverse of osteocalcin blood level (the lower is the osteocalcin and the higher is the osteoblastic activity)

3 – Thyroid lateral adaptation reset:

| |
|---|
| Insulin resistance ↘ |
|                      Thyroid lateral adaptation reset |
| Gonado-thyreotrope index ↗ |

\*\* Thyroid lateral adaptation reset: it measures the permanent level of reactivation of the thyroid for adaptation purpose, independently of the General Adaptation Syndrome This index is rarely used, because rarely out of norms, however it can be useful
to understand patients who tend to have a permanently high insulin resistance which
prevents to maintain sufficient cells nutrition through glucose, resulting in
an underweigth situation This index is highly dependent on TSH value: the higher TSH is, the lower is the insulin activity, and consequently the higher is the insulin resistance (see below, TSH and the somatotrope axis)

4 – TRH activities:

- Role of TRH:
- stimulate TSH and estrogens (through TSH and through stimulation of estrogenic receptors)
- triggers secretion of prolactin
- releases histamine
- stimulate GHRH, which in turn stimulates both GH and somatostatin
- stimulate calcitonin (parathormone antagonist), which lowers calcium and phosphate blood levels and helps reintegration in bones
- is decreased by dopamine
- is increased by noradrenaline (alpha sympathetic)

| |
|---|
| TSH ↘ |
|         TRH endocrine |
| T4 ↗ |

\*\* TRH endocrine: it measures the endocrine activity of TRH within the thyreotrope axis

| |
|---|
| T3 ↘ |
|         TRH intra-thyroid |
| T4 ↗ |

\*\* TRH intra-thyroid: it measures the relative level of T3 vs T4

| |
|---|
| Amylosis ↘ |
|         TRH / TSH |
| Adenosis ↗ |

\*\* TRH / TSH: it measures the level of TRH activity on tissues, relative to TSH activity. It can be associated with 2 factors
1 – the build-up of amyloid deposits, which is a catabolic activity, directly under TRH influence
2 – the activity of adenosis, which is an hyperplasic activity, hence anabolic, and TRH varies like the inverse of adenosis This index is tricky and ones should not conclude that the endocrine activity of TRH increases because the TRH/TSH index increases:
- TRH is very sensitive to stress, all kinds of stress, and the index can jump, for example, in a period of high mental creativity, without endocrine activity
- when it is a situation of <u>chronical stress,</u> the index can decrease, although TRH increases, because the TRH-TSH threshold is increased. It is a situation where TRH action focused on the thyreotrope axis
- conversely, the TRH/TSH index can increase, when TRH action is <u>external</u> to the thyreotrope axis, for example focused on pancreas, which activates the endocrine pancreas in its glucagon activity, and increases the CA 19/9 mark

| |
|---|
| Monocytes ↘ |
|         Thyroid reactivation index |
| Lymphocytes ↗ |

\*\* Thyroid reactivation index: it measures the level of stimulation of the thyreotrope axis by the locus coeruleus. By extension, it measures the disadaptation of the organism (see below)

The reactivation of the thyreotrope axis is done through a <u>short circuit</u> of the adaptation process between thyroid, parasympathetic, cerebral cortex and locus coeruleus, which reactivates the alpha sympathetic. The latter will trigger a chain reaction: Alpha → CRF → TRH → Thyroid in periphery (T4), with the help of Interleukin, which reactivates FSH and estrogens, which in turn will reactivate TSH and the thyroid.

When this disadaptation goes along with a feeling of losing self-confidence, the organism can move towards either a depression state or towards a state favoring the activation of inflammation. As an example, a simple antidepressant plant treatment can give excellent results on a rheumatoid arthritis in its early stage Thyroid reactivation ↘   GT ratio ↘
      Adjusted Thyroid reactivation index

\*\* Adjusted Thyroid reactivation index: it measures the endogenous part in the level of solicitation of the thyreotrope axis by the locus coeruleus.

This index is rarely used, however, <u>if the index is high</u>, it can be one of the two causes of inflammation with necrosis.

5 – Amylosis activity:

\*\* Amylosis index: it measures the level of solicitation of the amyloid activity of the organism
- there are some 21 amyloid proteins, which are gamma globulin proteins created by the bone marrow to protect ourselves against infections and other diseases. There are destroyed afterwards, but it happens that they can mix with other substances to create amyloid fibrils.
- these <u>amyloid fibrils</u> are extra-cellular: they have no nucleus and they do not generate inflammatory reaction, but they tend to gradually choke normal structures. They cannot generate cancer, because they have no nucleus
- the <u>organs</u> which can suffer from these amyloid fibrils are the kidneys (renal insufficiency), the heart (cardiomyopathy), the digestive tract (diarrhea), the liver, the skin and the nervous system, generating cellular degeneration (for example Alzheimer's disease)

<u>EVALUATION GUIDELINES  4 – Somatotrope axis</u>

<u>Endocrine system</u>

*Peripheric alpha*
↓

| CRF | → | Gn-RH | TRH | GH-RH<br>GH-IH | |
|---|---|---|---|---|---|
| ↓ | | | | | |
| ACTH | → | FSH / LH | TSH | GH | |
| Adrenal | | Ovaries | Thyroid | Pancreas | |

| gland | Testicles | Parathyroïd | Liver |
| --- | --- | --- | --- |
| Cortisol | Estros/ Proges | T4 / T3 | Insulin |
| Aldosterone | Genital andros | PTH | Glucagon |
| Adrenal andros | | Calcitonin | Somatostatin |

C E L L S

The somatotrope axis controls the cellular development through the growth hormone, which increases the speed of synthesis of proteins and other cell elements. The role of the somatotrope axis in the General Adaptation Syndrome is to do the reconstruction work to restore the initial state, upon request from the thyreotrope axis, and it will act on the gonadotrope axis to ensure availability of raw material.

The pancreas has a key role for supporting the cell growth activity through 2 hormones: insulin, which reduces glycaemia, and increases glucose penetration at cell level and glucagon, which liberates into blood the glucose produced in the liver from the glycogen.

SEARCH SEQUENCE

| Measurements | Assessment |
| --- | --- |
| - Metabolism and congestion: ↓ | → metabolism components (cata, ana) and link with thyroid and estrogeny<br>→ watch overall metabolism rate and link with adrenal gland => usually strong cortisol leads to hypo metabolism<br>→ impact of hypo metabolism on ischemia and congestion |
| - Growth and anti-growth ↓ | → watch impact of TSH on cell turnover and intra-cell growth<br>→ growth elements and growth scores |
| - Pancreatic and prolactin activities ↓ | → impact of TSH and cata-ana on insulin<br>→ impact high insulin on oxidation<br>→ cortisol impact on somatostatin & link with GH<br>→ link insulin resistance and ketonic index<br>→ link insulin resistance and pro-amyloid<br>→ link prolactin and somatostatin |
| - Oxidoreduction activities | → oxidoreduction and its components<br>→ link Oxidation with TSH<br>→ excess of free radicals versus needs |
| - Cellular activity:<br>. Membrane expansion rate<br>. Structural expansion rate<br>. Membrane fracture rate<br>. Cellular permeability | → link with catabolism<br>→ link with anabolism<br>→ link with metabolism and turnover<br>→ link with potential histamine |

| | |
|---|---|
| - Cellular death: | |
| . Fibrosis | → impact of high TSH (low thyroid) |
| . Apoptosis | → link with cell proliferation |
| . Physiological Apoptosis | → link with congestion |
| . Relative Necrosis vs Apoptosis | → link w. Membrane fracture |
| . Quantitative necrosis | → effective necrosis |

→ TSH and the somatotrope axis:
- TSH, reflecting of the state of thyroid, has a very large influence on the somatotrope axis, either accelerating or inhibiting cell growth, The scope of variance of TSH is large (in practical terms from 0,6 to 3, i.e. a factor of 5), which can overcome the influence of other factors:
- TSH low = Thyroid strong = Cell growth activated
  → Cell turnover decreased (= accelerated)
  → Intra cell growth increased
  → Anti-growth decreased
  → Somatostatin decreased
  → Insulin increased
  → Insulin resistance decreased
  → Membrane expansion increased
  → Membrane fracture increased
  → Oxidation increased
- TSH high = Thyroid weak → reverse effect

BACK-UP

1 – Metabolism and Congestion:

| |
|---|
| Thyroid metabolic activity ↘ |
| Catabolism rate |
| Adrenal gland ↗ |

\*\* Catabolism rate: it measures the catabolic activity of the organism.

- catabolism depends almost exclusively on the thyroid activity, and logically the catabolism rate varies like the thyroid metabolic activity
- adrenal gland: a high stress, triggering an increase of the adrenal gland activity, tends to reduce the metabolism (see below Metabolism and stress), and hence catabolism varies like the reverse of adrenal gland activity

| |
|---|
| Catabolism rate ↘ |
| Anabolism rate |
| Cata-ana ratio ↗ |

\*\* Anabolism rate: it measures the anabolic activity of the organism.

**  Metabolism rate: it measures the overall metabolic activity of the organism
It is the weighted sum of its components (catabolism and anabolism)

- Metabolism and stress: a situation of stress usually generates a situation of hypometabolism, because the adrenal gland is insufficient to cover both its adaptation and its permissivity requirements, the trade off in favor of adaptation reducing the linking of the adrenal gland with anabolic activities, through permissivity .

- Metabolism and cancer:
- in the development of a tumor, there is always a time of strong increase of cellular activity, which will trigger a strong increase of metabolism
- the tumor will, at a point in time, secure its own metabolism through the growth factors. It will reach an intra-cellular hyper metabolism « on site », which will not appear in the global measurement of metabolism: the latter will reduce sharply, and it is usually an indication of a regain of activity of the pathology.

- Metabolism and congestion: a reduction in metabolism usually triggers a congestion phenomenon, which is an adaptation mechanism to increase cells nutrition in a constrained environment. If the congestion response is stronger than expected, it can suggest a pathogenic environment

| Bone remodelling ↘ | Ajusted apoptosis ↘ |
|---|---|
| | Ischemia |
| Metabolism rate ↗ | |

** Ischemia: it measures the level of tissue congestion relative to the level of cell metabolic activity

- metabolism → it is the primary factor of ischemia: a reduced metabolism will indicate a production of metabolites and energy insufficient versus the requirements, and consequently a lack of oxygenation which will increase ischemia
- adjusted apoptosis → it is a consequence of ischemia which creates a beginning of necrosis. The organism will increase apoptosis to eliminate the cells
in difficulty, and the higher is the ischemia, the higher is the reactional apoptosis
- bone remodeling is a big consumer of estrogenic metabolism to the detriment of other cells: it is an amplifying element and the bigger is bone remodeling, the higher is the risk of ischemia

- Ischemia is a decrease or a stop of blood circulation in an organ or a tissue. The immediate implication is a congestion of the organ to supplement additional circulatory elements in the damaged area.
- ischemia generates a lack of oxygenation, which can be reversible, when it hits a muscle during a strong effort. A chronical ischemia can have more serious consequences, such as an inflammation of blood vessels (vasculitis), which can trigger necrosis processes and generate infarction, breathing troubles, and various metabolic disorders.
- vasculitis does not imply necessarily arteriosclerosis, it implies an hyper metabolic activity, with congestion and increase of blood volume. It usually implies an hyperactivity of vessels histamine on site.

| Ischemia ↘ |
|---|
| Splanchnic congestion |
| Carcinogenic expansion ↗   Metabolism ↗ |

\*\* Splanchnic and Pelvic congestion: they are the major centers for congestion within the organism
- the splanchnic congestion manages the digestive function
- the pelvic congestion manages the urinary elimination
- the link between the two types of congestion is through the vascular system
→ a splanchnic congestion, called for increasing adaptation, usually creates a pelvic congestion through a slow-down of the venous return
→ conversely a pelvic congestion does not necessarily generate a splanchnic congestion, except on a longer time frame, when the adaptation of pelvic organs requires an hyper activity both hepatic and pancreatic.

\*\* Splanchnic congestion: it measures the relative level of active congestion of the splanchnic area. It varies like ischemia and is increased by a reduced metabolism. Congestion being the physiological response of the organism to an organ under aggression, in order to increase its nutrients and oxygenation, it will precede an increase in inflammation, and as such it serves its role of protection as long as the Carcinogenic expansion is low. It will decrease when the Carcinogenic expansion prevails and generates an increased inflammation through necrosis (see definition in the Cancer example related indexes)

| Fibrosis ↘ |
|---|
| Adenosis |
| Carcinogenic expansion ↗ |

\*\* Adenosis: it measures the activity of endocrine factors which can trigger hyperplasia
- adenosis describes the set of events which trigger an organ to increase its yield and volume, through an increase of metabolism. This increase of exchanges will induce imbalances in the organ, either because it suffers from ischemia or from congestion, or beacuse the organ is particularly solicitated. It can trigger an uterine fibroma, associated with an uterine congestion, or a thyroid adenoma, or nothing initially in spite of an adenosis very high. On a longer term, a high adenosis could lead to a global hyperplasia within a tissue or an organ, which could eventually become cancerous.
- there are two main factors inducing adenosis:
1 – an excess of fibrosis: adenosis is a temporary phenomenon of accelerated growth which precedes hyperplasia: like any type of growth, adenosis needs fibrosis to prevent an excessive expansion, hence fibrosis varies like adenosis and the organism will put in place a state of fibrosis to isolate the organ, with suspicious growth, from the rest of the organism
2 – carcinogenic expansion: like for congestion, adenosis precedes carcinogenic expansion and varies like its inverse. It will tend to decrease when the pathology development will become important. (see definition in the Cancer example related indexes)

- Treatment: a long standing adenosis can be potentially dangerous, particularly if it is the consequence of a carcinogenic expansion excessively low. It can be reduced by treating the excess of fibrosis, which is often associated with an excess of TSH.

2 – Growth and anti-growth:

| TSH ↘ | Bone isoenzymes ↘ |
|---|---|
| | Turnover |

Turnover**: it measures the speed of cell renewal. The higher it is, the slower is the speed of renewal and conversely.
- they are mainly 2 factors involved in the turn-over:
1 – TSH, which indicates indirectly the level of catabolic activity, necessary for any cell renewal activity: the lower is TSH, the stronger is the thyroid, and the lower is the turnover, hence the faster is the cell renewal
2 – Alkaline phosphatases Bones isoenzymes: they indicate the level of anabolic activity, supported by estrogens. Turnover varies like the Bones isoenzymes, which usually vary in a narrower range than TSH.

- a cancer development often results into a slower speed of cell renewal, hence a higher turnover.
- conversely an hyperthyroidism will tend to reduce TSH and the turnover, resulting in a higher speed of cell renewal

| Bones isoenzymes ↘ | |
|---|---|
| | Growth hormone activity |
| Osteocalcin ↗ | |

GH activity**: it measures the activity of the Growth hormone

- there are mainly 2 factors involved in the measurement of the GH activity:
1 – Alkaline phosphatases Bones isoenzymes: like above, they indicate the level of anabolic activity, supported by estrogens. GH varies like Bones isoenzymes
2 – Osteocalcin: this protein plays a key role in the bone development activity, and by extension in the anabolic activity. Its blood level is an indication of its activity: the lower it is and the higher is its activity, and consequently GH varies like the inverse of osteocalcin.

- organic growth: this concerns the growth of the number of cells, not the growth of the cell renewal. The following will occur:
…an increase of GH
…a more important increase of anti-growth and apoptosis
…an intra-cellular growth very low
…an increase of the TSH/thyroid ratio, in other words high TSH and low thyroid yield
…an increase of the ratio para sympathetic / alpha sympathetic to increase secretions

- intra-cellular growth: this concerns the growth of the cellular activity.
The following will occur:
…a high cortisol and a low GH ....an increase of oxidoreduction and a nucleus hyper activity leading to necrosis
...a decrease of the TSH/thyroid ratio, in other words an hyperthyroidism triggering an hyper oxidation and some necrosis.

```
GH activity ↘
         Intra-cellular growth
Turnover ↗
```

\*\* intra-cellular growth: it measures the intra-cellular activity of growth factors. It is equal to the growth activity, corrected by the speed of cells renewal In other words, when the turnover is low (hence fast), the intra-cellular growth is high and conversely.

- TSH and intra-cellular growth: a low TSH usually triggers a high intra-cellular growth.

```
Somatostatin ↘        Cortisol ↘
              Anti-growth
```

\*\* Anti-growth: it measures the activity level of the anti-growth factors.
Anti-growth varies like 2 elements:
- somatostatin, an antagonist of GH
- cortisol, which has an anti-anabolic role

- TSH and Anti-growth: a high TSH usually triggers a high anti-growth activity.

```
GH ↘     Anti-growth ↘
         GH growth score
Intra-cellular growth ↗
```

\*\* GH growth score: it measures only the result of the GH metabolic activity, excluding the effect of anti-growth factors

- GH growth score and GH: both can vary in opposite directions, f.e. a high GH growth score with a low GH, and conversely. The explanation is as follows:
....growth occurs when anti-growth factors are adapted to GH
....if GH is strong, with an insufficient anti-growth, the GH growth score will be insufficient, hence low. GH will decrease as GH growth score increases

- TSH and GH growth score: a high TSH amplifies the value of the GH growth score

```
GH growth score ↘
         Global growth score
Somatostatin ↗
```

\*\* Global growth score: it measures the real growth resulting from the balance between growth and anti-growth factors. It is equal to the GH growth score adjusted by the somatostatin, which is a strong GH antagonist.

- Global growth score and cancer: Global growth score is a useful measurement to track the evolution of a cancer. The higher it is, the higher is the development risk.

3 – Pancreatic and prolactin activities:

| Cata-ana ↘ | | |
|---|---|---|
| | Insulin | |
| TSH ↗ | Turnover ↗ | |

\*\* Insulin: it measures the level of the endocrino-metabolic activity of the insulin. There are 3 main factors which describe 3 essential roles of insulin:
....the cata-ana ratio is the indicator of the installation of the General Adaptation Syndrome, where insulin plays a key role to release the glucose to the priority organs. By extension it varies like the cata-ana ratio
....the insulin participates with the thyroid in the mobilization of energy stocks, hence it varies like the thyroid, or the inverse of TSH: a strong TSH inhibits insulin and conversely a low TSH, hence a strong thyroid, generates a strong insulin
....the third role of insulin is to increase cells nutrition to support their renewal.
Insulin varies like the inverse of turn-over: a low turnover indicates a fast cell renewal, hence an important nutritional requirement and an increase of insulin.
Conversely an increase of turnover is a sign of a slowdown in cells renewal, and will generate a decrease of insulin.

- Insulin actions and reactions: It is the only hormone which can reduce glycaemia, in order to get the blood glucose to penetrate cells to increase their energy or to return to liver to be kept in reserve as glycogen. Its stimulation is direct: an hyperglycemia will stimulate insulin synthesis. Insulin reactions are numerous:
....it is inhibited by somatostatin, which also inhibits GH
....it is inhibited by serotonin
....it is inhibited by alpha sympathetic
....it is inhibited by a strong TSH (and increased by a weak TSH)
....it blocks GH activity, in case of hyperemia \*\* Insulin and stress:
- the normal reaction to a stress situation is a discharge of adrenalin through the beta sympathetic
- when aggression seems to last or if it is chronical, the organism will choose the glucagon route, with liberation of glucose, which triggers an increase in metabolism, and a participation of insulin:

| Insulin ↘ | | |
|---|---|---|
| | Demyelination | |
| GH ↗ | Intra-cell. growth ↗ | |

\*\* Demyelination: it measures the relative part of insulin adaptation activity in its chronological link with GH
There are 3 factors which influence demyelination:

1 – Insulin: when insulin increases, driven by glucagon, the demyelination index increases. This does not imply an actual demyelination, but rather an environment favorable to demyelination
2 – GH and intra-cellular growth: they are factors of amplification of the demyelination development, which is only active when insulin anticipates over GH, i.e. the lower are GH and the intra-cellular growth, relative to insulin, and the higher is the risk of demyelination The <u>Adjusted demyelination index</u> (demyelination index adjusted by the starter index, hence the relative weight of glucagon), gives an amplification of the demyelination risk.

```
Anti-growth ↘
           Somatostatin
Cortisol ↗
```

\*\* Somatostatin: it measures the activity level of the somatostatin
There are 2 factors which influence Somatostatin:
1 – Anti-growth: the role of somatostatin is <u>strongly inhibitor</u>, particularly over the Growth hormone (GH). It is one of the main anti-growth factors and it varies like the Anti-growth index
2 – Cortisol: it increases GH receptors activity, while Somatostatin has a reverse effect on same receptors, hence Somatostatin varies like the reverse of Cortisol
*Example*: during childhood, cortisol activity decreases until the age of 11-13 years old, when the overall GH growth score, resulting from Growth and Anti-growth factors is at its peak. Afterwards the cortisol will increase with the decrease of the overall GH growth score until the age of 20, triggered by the decrease of both GH and Anti-growth factors, including Somatostatin
- Somatostatin permits to assess the level of activity of the <u>exocrine pancreas</u>:
when exocrine pancreas is under functioning, somatostatin is usually insufficient, while endocrine pancreas is over functioning, generating an hyperemia.
- Somatostatin has a strong inhibiting activity:
… it strongly inhibits GH, and reduces also TSH secretion
… it reduces <u>neurons excitability</u> and inhibits many neurotransmitters secretion
… at the level of the pancreatic islets, somatostatin inhibits, through paracrine effect, the secretions of insulin and glucagon, which explains the reverse activities of exocrine and endocrine pancreas
… at <u>gastrointestinal level</u>, somatostatin, inhibits most of the peptides secretions, reduces exocrine secretions, inhibits digestive motricity and reduces blood output at the level of the mesentary
… somatostatin secretion is <u>stimulated</u> by the <u>beta-sympathetic</u>

```
Somatostatin ↘
           Insulin resistance
Insulin ↗
```

\*\* Insulin resistance: it measures the level of inhibition of the membrane activity of the insulin, independently of its temporary activity, linked to adaptation.
There are 2 main factors which influence the insulin resistance:

1 – the somatostatin: insulin resistance is a GH inhibitor at cell level, hence it varies like somatostatin, which is a strong GH inhibitor
2 – the insulin: insulin resistance varies like the reverse of insulin, i.e.
it decreases when insulin is strong, to facilitate the glucose access to cells, and conversely it is strong when insulin is low.

- insulin resistance will increase in case of stress to prevent the glucose access to cells, in order to ensure that the priority organs (heart, brain, muscles,..) get enough energy elements.

| Starter ↘ |
|---|
| Ketonic index |
| Insulin ↗ |

Ketonic index**: it measures the relative part in the cell nutrition of the ketonic route, relative to the insulin route
There are 2 main factors which influence the ketonic index:
1 – the starter index, which indicates the relative level of glucagon versus the level of adrenaline in the initiation of the General Adaptation syndrome. This mobilization will increase glycaemia before the organism can react. The ketonic index will vary like the starter index, since an hyperglycemia triggers another
way of cell nutrition
2 – Insulin is the classic way of cell nutrition response to an adrenalin discharge: the lower is the insulin, the higher is the need for an alternative nutrition (in this case lipids generating some ketonic waste) and the higher is the ketonic index, which varies like the reverse of insulin.

| Insulinic resistance ↘ | Reduction ↘ |
|---|---|
| Pro-amyloid activity | |

Pro-amyloid**: it measures the level of cell hypometabolism. By extension it measures the level of respiratory and nutritional insufficiency at cell level
There are two factors which influence this measurement:
1 – the insulin resistance, which inhibits the glucose access to cells: the higher is the insulin resistance, the lower will be the level of cell metabolism, and the higher will be proamyloid activity.
2 – the reduction, which measures the reduction phase of the oxidoreduction and by extension it measures the level of anti-oxydant activity of the organism. It will increase the level of respiratory insufficiency at cell level, and consequently the proamyloid activity varies like the reduction.

| PAP (Prostate Acid Phosphatase) ↘ |
|---|
| Pancreatic index |
| PSA (Prostate specific Antigen) ↗ |

Pancreatic index**: it measures the level of cell nutrition of the exocrine pancreas. It is equal to the PAP/PSA ratio:
- if ratio < 0,7 → pancreatic insufficiency

- if ratio > 2,0 → pancreatic hyperactivity

- Prostate cancer risk factors: the probability of a prostate cancer increases if:
....increase of PSA, without similar increase of PAP, generating an hypo activity of the exocrine pancreas
....GH factor high
....turnover very low, hence fast cell renewal
....jncrease of alkaline phosphatases intestinal isoenzymes (sign of hypermetabolism and fast metabolic exchanges)
....genital insufficiency at androgens level (hence low estrogeny)

| Somatostatin ↘ | TSH ↘ |
|---|---|
| | Prolactin index |
| GH activity ↗ | |

Prolactin index:** it measures the level of activity of the prolactin and indicates the level of stimulation of the General Adaptation Syndrome.
There are 3 main factors which influence the prolactin:
1 – the somatostatin: prolactin is part of the somatotrope axis and plays a key role in the move from growth to anti-growth. It inhibits GH, hence it varies like the somatostatin
2 – TSH: prolactin is stimulated by TRH, which stimulates TSH, hence prolactin varies like TSH
3 – GH: prolactin inhibits GH, hence the higher is GH, the lower is prolactin and conversely. Prolactin varies like the reverse of GH.

- Prolactin actions and reactions:
- it makes the bridge between growth and anti-growth by ensuring the reactivation of the ACTH and of the corticotrope axis
- it inhibits GH, but GH does not stimulate prolactin
- it is inhibited by Dopamine and Estrogens
- it is stimulated directly by TRH ; which helps influencing the transfer between FSH and LH
- it can transform Estrogen receptors into Progesterone receptors: this is why applying anti-estrogens without blocking the prolactin can be counter-productive, because it reactivates FSH-LH and the progesterone
- it stimulates MSH
- if permanently increased, it can generate an increase of the alpha sympathetic by reactivity

- Dopamin actions and reactions:
- it is closely associated with Prolactin: it inhibits Prolactin and conversely, when it decreases, prolactin increases
- it can inhibit Prolactin to the point of preventing the reactivation of ACTH
- it is inhibited by T3 and estrogens
- it stimulates GH
- it inhibits the pituitary hormones (ACTH, FSH, LH) and TSH to a lesser degree: it modulates the secretion of pituitary hormones:
→ Example: a lasting decrease of cortisol will reactivate ACTH, which would become permanent without the intervention of the central Dopamine. The latter will reduce the reactivity of ACTH, by inhibiting the Prolactin, and modify the threshold level of ACTH response to a decrease of cortisol.

4 – Oxidoreduction activities:

| Insulin ↘ | Necrosis ↘ |
|---|---|
| | Oxidoreduction |
| Fibrosis ↗ | Somatostatin ↗ |

\*\* Oxidoreduction : it measures the resulting level of oxidoreduction, following oxidative and anti-oxidant actions.

There are a number of factors which influence oxidoreduction, but the base logic is rather simple:
1 – oxidoreduction <u>varies like</u> factors which <u>support a fast cell renewal</u>, which require a high level of oxidoreduction . The main factors are shown above, starting with Insulin, a mandatory step to bring energy to cells and Necrosis, the indirect implication of a fast intra-cell growth, with high membrane fracture
2 – oxidoreduction <u>varies like the reverse</u> of factors which <u>inhibit growth</u> and consequently reduce the needs for a high oxidoreduction. Factors such as Fibrosis and Somatostatin do inhibit the growth and have been selected for that reason.

| Insulin ↘ | Intra-cell growth ↘ |
|---|---|
| | Oxidation |
| Anti-growth ↗ | |

\*\* Oxidation: it measures the oxidation in the oxidoreduction. By extension, it contributes to the assessment of the level of cell respiration.

There are 3 main factors which influence the oxidation:
1 – growth factors which contribute to the demand of oxidation: Insulin and Intra cell growth
2 – anti-growth factors which reduced the demand for oxidation: Anti-growth

| Reduction ↘ | |
|---|---|
| | Reduction |
| Oxidoreduction ↗ | |

\*\* Reduction: it measures the part of reduction in the oxidoreduction. By extension, it contributes to the assessment of the anti-oxydant activity of the organism.

| Oxidoreduction ↘ | |
|---|---|
| | Free radicals |
| Insulin ↗ | |

\*\* Free radicals: it measures the circulating rate of free radicals. Since by definition the free radicals are circulating unstable oxygen molecules, the rate varies like oxidoreduction, corrected by the oxygen molecules which penetrate cells through insulin

| Free radicals ↘ | DNA fracture ↘ |
|---|---|
| Free radicals harmfullness | |
| Apoptosis ↗ | |

Free radicals harmfulness:** it measures the rate of toxic free radicals relative to justified free radicals. By extension it indicates the excess of energetic supply versus organism needs. It will tend to be very high during a cancer proliferation phase

5 – Cellular activities:

| Intra-cell growth ↘ | Catabolism rate ↘ |
|---|---|
| Membrane expansion rate | |

Membrane expansion rate:** it measures the level of the membrane metabolic activity. Two growth factors are involved:
1 – the <u>intra-cell growth</u>, which measures the level of cellular activity of growth factors
2 – the <u>rate of catabolism</u>, which is the starting point of the cellular expansion
- a <u>strong membrane expansion rate</u> indicates a predominance of <u>growth factors</u> over <u>structural factors</u>: the higher is the membrane expansion, and the closer
is the risk of a membrane fracture with necrosis

| Nucleus-Membrane activity ↘ | Anabolism rate ↘ |
|---|---|
| Structural expansion rate | |

Nucleus expansion rate:** it measures the level of metabolic activity of the nucleus. There are 2 factors involved:

1 – the <u>nucleus-membrane activity</u> which expresses the relative level of metabolic activity (nucleus versus membrane)
2 – the <u>rate of anabolism</u> of the organism, resulting from the action of estrogens over nucleus.
- a <u>strong nucleus expansion rate</u> indicates a predominance of <u>structural factors</u> over <u>growth factors</u>. It will indicate in particular a strong intra-cellular protein activity.

| Metabolism rate ↘ | |
|---|---|
| Membrane fracture rate | |
| TSH ↗ | Turnover ↗ |

Membrane fracture rate:** it measures the degree of fragility of the membrane and in consequence its risk of break-up

- There are 3 factors involved in this measurement:
1 – the <u>rate of metabolism</u>: a membrane expansion requires metabolic activity, and hence the membrane fracture rate varies like the rate of metabolism
2 – any membrane expansion requires the thyroid in its contribution to the metabolic activity. The membrane fracture rate will vary like the level of <u>thyroid activity</u>, hence like the reverse of TSH. The stronger is the thyroid activity, the lower is the TSH and the higher is the membrane fracture rate.

3 – membrane expansion varies like the cell renewal: the faster is the cell renewal (i.e. the lower is the turnover), the higher is the membrane expansion, and consequently the membrane fracture rate will vary like the reverse of the turnover.

- when membrane fracture rate is high, it usually does not correspond to a situation of an active cancer pathology. A high rate is more reassuring than worrying, since it usually leads to necrosis. Membrane fracture can appear over terrains which can generate cancers over time, from the nuclear waste, but it does not appear over active cancer terrains. When cancer starts developing, membrane fracture will reduce.

** Cell permeability: there are 2 measurements:
1 – Active cell permeability: it measures the degree of cross-membrane permeability, which is under estrogenic influence
2 – Passive cell permeability: it measures the degree of cross-membrane activity strictly osmotic, which is influenced by 3 factors:
... necrosis which is facilitated by an increased cell permeability
... nucleus / membrane relative activity, which triggers membrane access to nutrients and facilitates cell permeability
... cortisol, which tends to weaken the membrane, particularly in its adaptative role, measured by the adaptation permissivity index.
→ Warning: this index can be negative, if the adaptation-permissivity is negative. It should then be considered on its absolute value 6 – Cellular deaths:

| TSH ↘   Osteocalcin ↘ |
|---|
| Fibrosis |

** Fibrosis: it measures the fibrosis activity of the organism, from a simple isolation to the hardening degeneration of a set of tissues or organs

- there are 2 main factors influencing fibrosis:
1 – TSH: fibrosis is an anti-growth factor, hence it will be stimulated by a weak thyroid, i.e. a strong TSH, and it will vary like TSH
2 – osteocalcin: a high fibrosis is often associated with an imbalance of calcium metabolism in the area under fibrosis, triggering an increase of osteocalcin blood level, hence fibrosis varies like osteocalcin blood content

* more details on Fibrosis:
- it is a progressive destruction of the nucleus with transformation into an inert fibrotic issue, which is not eliminated, contrary to cellular deaths through apoptosis and necrosis.
- it solidifies membranes through keratinization: the cell fracture decreases, the nucleus-membrane activity reduces in favor of a stronger membrane and the rate apoptosis decreases
- it is part of the growth syndrome and it puts a boundary on growth. Fibrosis is a necessary component to have a « normal » growth.

- <u>when fibrosis is high</u>, the fibrosis hyper activity indicates a modification of growth factors: it can be a situation of <u>reconstruction</u> of the organism or it could be a situation of <u>anti-growth</u> to respond to an anomaly of structure. Response will be given by analyzing somatotrope and thyreotrope axis:
....either they are in phase, f.e. both in hyper activity, we have a situation of reconstruction, and fibrosis is part of that reconstruction
....or they are not in phase, a high fibrosis indicates a defense system to protect an organ against an aggression, and it could imply a pre pathologic situation
- fibrosis increases in case of <u>viral hepatitis</u>, when it is moving towards cirrhosis. It can equally increase with degenerative pathologies, like <u>multiple sclerosis</u> or <u>Alzheimer disease</u>, or with other pathologies such as <u>arthrosis</u> or <u>atheroma</u>.
- in case of cancer pathologies, organism tries first to circumvent the group of damaged cells through fibrosis, and when those cells proliferate (hyperplasia),
fibrosis will <u>collapse</u>, well before a tumor is formally identified.

| |
|---|
| Structural expansion rate ↘ |
| Apoptosis |
| Membrane expansion rate ↗ |

\*\* Apoptosis: it measures the overall level of apoptosic activity of the organism.
There are 2 main factors influencing the apoptosis:
1 – <u>Structural expansion rate</u>, which indicates the metabolic level of the nucleus: the higher is the nucleus expansion, the closer we get to the cell programmed death, occurring after a limited amount of cell divisions. Apoptosis index <u>will vary like</u> the nucleus expense rate
2 – <u>Membrane expansion rate</u>: the stronger is the membrane expansion, the higher is the risk of membrane fracture, with break-up of the cell: it is a situation of <u>necrosis</u> with nuclear waste, instead of a programmed death by apoptosis. Conversely a weak membrane expansion rate reduces necrosis and increases apoptosis. Apoptosis varies <u>like the reverse</u> of membrane expansion rate.

\* more details on Apoptosis: it is a kind of active cell death, associated with a shrinkage of the cell, resulting in a fragmentation into waterproof elements, which will be absorbed through macrophagocytosis. It is a programmed death for cells in excess or potentially harmful
→ Apoptosis is a clean death, without waste, as opposed to Necrosis which will trigger cell burst, followed by a local inflammatory reaction, with waste which will hit the liver.
→ there can be 2 kinds of opposite situations in terms of pathologies:
- an <u>insufficient apoptosic system</u>: it can be due to an increase of anti-apoptosis processes to facilitate organic cell growth, or it can be due to a lack of reactivity of the cell nucleus, an hypo activity which prevents to increase apoptosis: this kind of situation can lead to uncontrolled cell proliferation and represents a high risk of carcinogenesis
- an <u>over activation of the apoptosic system</u>: it is a situation of pathologic apoptosis by excess of apoptosis, which can be due to an over reactivity of the cell nucleus, which triggers an increase of apoptosis, or to an over activation of initiating factors of apoptosis..
The latter can be, beyond physiologic apoptosis, an abnormal reactivation of apoptosis factors from the mitochondria, the cytoplasm or the membrane: this kind of situation will be found in many digestive diseases, including viral hepatitis, and also in the influenza and the AIDS disease.

| Apoptosis ↘ |
| Adjusted Apoptosis |
| Nucleus-Membrane activity ↗ |

\*\* Adjusted apoptosis: it measures the relative level of physiological apoptosis activity as a whole relative to apoptosis activity resulting from dysfunctional adaptation
→ the adaptation apoptosis is an anticipated cell death (versus its biological programmed death) decided by the organism when a lesion has created an abnormal cell, and hence a need for an anticipated death.

- The index Adjusted apoptosis varies like the overall apoptosis corrected by the relative activity level of the nucleus versus the membrane (Nucleus-Membrane activity)
It will indicate whether there are some added apoptosic factors, which we will find in congestive syndromes, adenomas or when there is a need to increase the thyroid volume to satisfy organism needs: there will be first a reduction of apoptosis to increase the tissue volume, and later an increase apoptosis to recover normal volume.

| Membrane fracture rate ↘ |
| Relative Necrosis |
| Apoptosis ↗ |

\*\* Relative Necrosis: it measures the relative cellular death by necrosis versus cellular death by apoptosis
There are 2 factors affecting the Relative Necrosis:
1 – the membrane fracture: necrosis is a consequence of membrane fracture, and hence Relative Necrosis varies like Membrane fracture
2 – the apoptosis: necrosis is an alternative to apoptosis, and the relative necrosis is a measurement relative to the apoptosis, hence it varies like the reverse of apoptosis

| LDH ↘    Necrosis ↘ |
| Quantified Necrosis |

\*\* Quantitative necrosis: it measures the quantification of the tissue necrosis for the organism. It is equal to the Relative necrosis adjusted by LDH, which expresses the thyroid metabolic activity required to create necrosis.

What is claimed is:

1. A method of treating a patient the method comprising:
receiving a list of signs from a clinical examination of the patient, and interpreting the signs into one or more potential organism dysfunctions across the endocrine system and the autonomous nervous system;
receiving blood test data and running a biological simulation model, including calculating a set of measurements called indexes, which measures interrelationships between one or more of hormones and blood test data, hormones and hormones, or hormones and organs;
analyzing, from the indexes, the endocrine system by axis of the endocrine system and in sequence along an adaptation process from the corticotropic axis (catabolic) to the gonadotropic axis (anabolic), then to the thyreotropic axis (catabolic) and finally to the somatotropic axis (anabolic);
running a selection algorithm from the indexes to identify the patient as having one or more biological dysfunctions across the endocrine system and the autonomous nervous system, capable of participating in the genesis, installation and evolution of a pathology in the patient, and recommending one or more corrective actions based on the identified one or more biological dysfunctions;
validating the one or more potential organism dysfunctions from the clinical examination through the identified one or more biological dysfunctions;
consolidating diagnostic actions including the recommended one or more corrective actions into a single diagnostic, and receiving selection of one or more diagnostic actions therefrom; and
treating the patient having the one or more biological dysfunctions to prevent or degrade the pathology, the patient being treated with a therapeutic strategy applicable to each selected diagnostic action, and including a quantified dosage of an associated medication for at least one selected therapeutic strategy.

2. The method of claim 1, wherein the blood test data is received to an apparatus, including a processor and a memory storing executable instructions, that, in response to execution by the processor, causes the apparatus to at least run the biological simulation model to calculate the set of indexes, and run the selection algorithm to identify the one or more biological dysfunctions.

3. The method of claim 1, wherein treating the patient includes for each selected diagnostic action:
providing one or more proposed therapeutic options for selection by the user; and in response thereto,
receiving selection of one of the proposed therapeutic options as the therapeutic strategy for the respective diagnostic selected action.

4. The method of claim 1, wherein receiving selection of one or more diagnostic actions further includes receiving selection of any user add-ons from the single diagnostic, each user add-on being a diagnostic action other than the recommended one or more corrective actions.

5. The method of claim 1, wherein the one or more corrective actions are recommended by axis of the endocrine system.

6. The method of claim 1 further comprising performing the clinical examination from which the list of signs is identified and interpreted into the one or more potential organism dysfunctions.

7. The method of claim 1 further comprising drawing blood from the patient to acquire a sample of blood from which the blood test data is obtained.

* * * * *

UNITED STATES PATENT AND TRADEMARK OFFICE
CERTIFICATE OF CORRECTION

PATENT NO. : 9,953,139 B2
APPLICATION NO. : 14/754193
DATED : April 24, 2018
INVENTOR(S) : Jean-Claude Lapraz Page 1 of 1

It is certified that error appears in the above-identified patent and that said Letters Patent is hereby corrected as shown below:

On the Title Page

(73) Assignee:
"Jumplion, Inc."
Should read:
(73) Assignee:
--Jumplion, Inc.
Patrice Pauly--.

Signed and Sealed this
Fifth Day of February, 2019

Andrei Iancu
*Director of the United States Patent and Trademark Office*